United States Patent
Barber

(10) Patent No.: US 10,821,142 B2
(45) Date of Patent: Nov. 3, 2020

(54) CANCER TREATMENT AND DIAGNOSIS

(71) Applicant: University of Miami, Miami, FL (US)

(72) Inventor: Glen N. Barber, Miami, FL (US)

(73) Assignee: STINGINN, LLC, Miami, FL (US)

( * ) Notice: Subject to any disclaimer, the term of this patent is extended or adjusted under 35 U.S.C. 154(b) by 0 days.

(21) Appl. No.: 16/284,975

(22) Filed: Feb. 25, 2019

(65) Prior Publication Data

US 2019/0314429 A1 Oct. 17, 2019

Related U.S. Application Data

(63) Continuation of application No. 15/735,502, filed as application No. PCT/US2016/037288 on Jun. 13, 2016, now abandoned.

(60) Provisional application No. 62/174,374, filed on Jun. 11, 2015.

(51) Int. Cl.
| | | |
|---|---|---|
| *A61K 35/763* | (2015.01) | |
| *C12Q 1/6886* | (2018.01) | |
| *A61P 35/00* | (2006.01) | |
| *G01N 33/574* | (2006.01) | |

(52) U.S. Cl.
CPC .......... *A61K 35/763* (2013.01); *A61P 35/00* (2018.01); *C12Q 1/6886* (2013.01); *G01N 33/57492* (2013.01); *C12N 2710/16633* (2013.01); *C12Q 2600/106* (2013.01); *C12Q 2600/156* (2013.01); *C12Q 2600/158* (2013.01); *G01N 2333/4706* (2013.01)

(58) Field of Classification Search
CPC .......... A61P 37/02; A61P 35/00; A61K 39/39; A61K 9/0019; A61K 39/12; A61K 2039/53; A61K 35/763; A61K 2039/6075; A61K 2039/5254; A61K 35/76; A61K 39/245; A61K 2039/525; A61K 2039/876; A61K 2039/80; A61K 39/285; C12N 7/00; C12N 2710/16632; C12N 2710/16633; C12N 2710/24132; C12N 2330/51

See application file for complete search history.

(56) References Cited

PUBLICATIONS

Xia T, Konno H, Ahn J, Barber GN. Deregulation of STING Signaling in Colorectal Carcinoma Constrains DNA Damage Responses and Correlates With Tumorigenesis. Cell Rep. Jan. 12, 2016;14(2):282-97. Epub Dec. 31, 2015.*
Corrales L, Glickman LH, McWhirter SM, Kanne DB, et. al. Direct Activation of STING in the Tumor Microenvironment Leads to Potent and Systemic Tumor Regression and Immunity. Cell Rep. May 19, 2015;11(7):1018-30. Epub May 7, 2015.*
Zhu Q, Man SM, Gurung P, Liu Z, Vogel P, Lannkanfi M, Kanneganti TD. Cutting edge: STING mediates protection against colorectal tumorigenesis by governing the magnitude of intestinal inflammation. J Immunol. Nov. 15, 2014;193(10):4779-82. Epub Oct. 15, 2014.*
Buijs PR, Verhagen JH, van Eijck CH, van den Hoogen BG. Oncolytic viruses: From bench to bedside with a focus on safety. Hum Vaccin Immunother. 2015;11(7):1573-84.*
Holm CK, et. al. Influenza A virus targets a cGAS-independent STING pathway that controls enveloped RNA viruses. Nat Commun. Feb. 19, 2016;7:10680. doi: 10.1038/ncomms10680.*
Ma Z, Damania B. The cGAS-STING Defense Pathway and Its Counteraction by Viruses. Cell Host Microbe. Feb. 10, 2016;19(2):150-8.*
Li Y, Wilson HL, Kiss-Toth E. Regulating STING in health and disease. J Inflamm (Lond). Jun. 7, 2017;14:11. doi: 10.1186/s12950-017-0159-2. eCollection 2017.*
Dai P, Wang W, Cao H, Avogadri F, Dai L, Drexler I, Joyce JA, Li XD, Chen Z, Merghoub T, Shuman S, Deng L. Modified vaccinia virus Ankara triggers type I IFN production in murine conventional dendritic cells via a cGAS/STING-mediated cytosolic DNA-sensing pathway. PLoS Pathog. Apr. 17, 2014;10(4):e1003989.*
Ishikawa H, Ma Z, Barber GN. STING regulates intracellular DNA-mediated, type I interferon-dependent innate immunity. Nature. Oct. 8, 2009;461(7265):788-92. Epub Sep. 23, 2009.*

* cited by examiner

*Primary Examiner* — Rachel B Gill
(74) *Attorney, Agent, or Firm* — Sci-Law Strategies, PC

(57) ABSTRACT

The present disclosure provides, in general, a method for selecting a therapy for treating cancer in a human subject and subsequently treating cancer in a subject, which includes isolating a cancer cell from a human subject having cancer, determining the functional activity of the innate immune regulator STimulator of INterferon Genes (STING) or the cellular nucleotidyltransferase, cyclic Guanosine Monophosphate (cGMP)-Adenosine Monophosphate (AMP) Synthase (cyclicGMP-AMP Synthase or cGAS) in the cell, and selecting a therapy for the cancer based on the functional activity of the STING or cGAS in the cell. Also provided, if the functional activity of STING and/or cGAS is determined to be defective in the cell, the therapy selected is one that is effective at killing STING-deficient and/or cGAS-deficient cancer cells, for example a therapy including administering to the subject an oncolytic virus.

20 Claims, 60 Drawing Sheets

Specification includes a Sequence Listing.

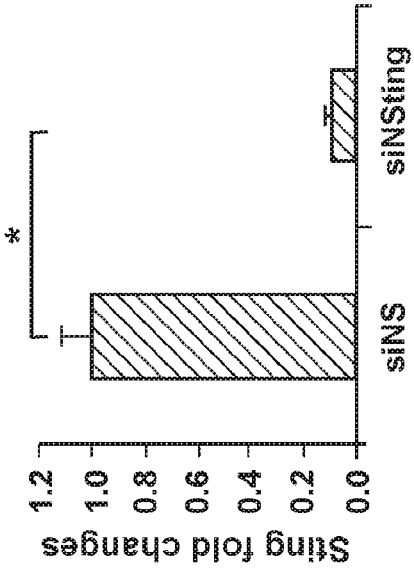
FIG. 1C
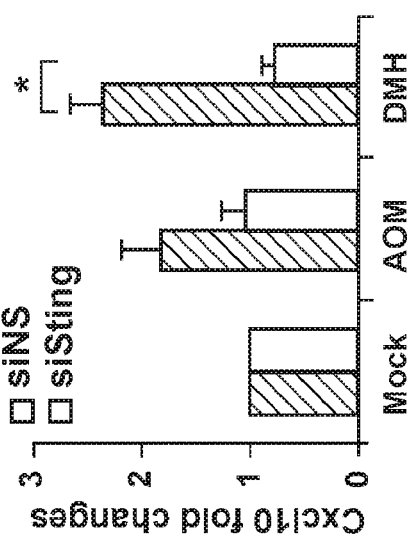
FIG. 1D
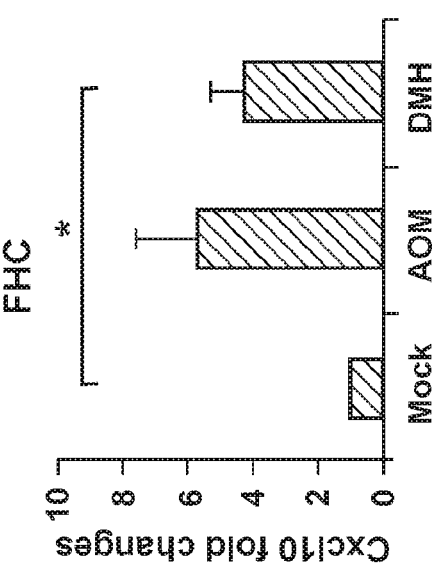
FIG. 1E
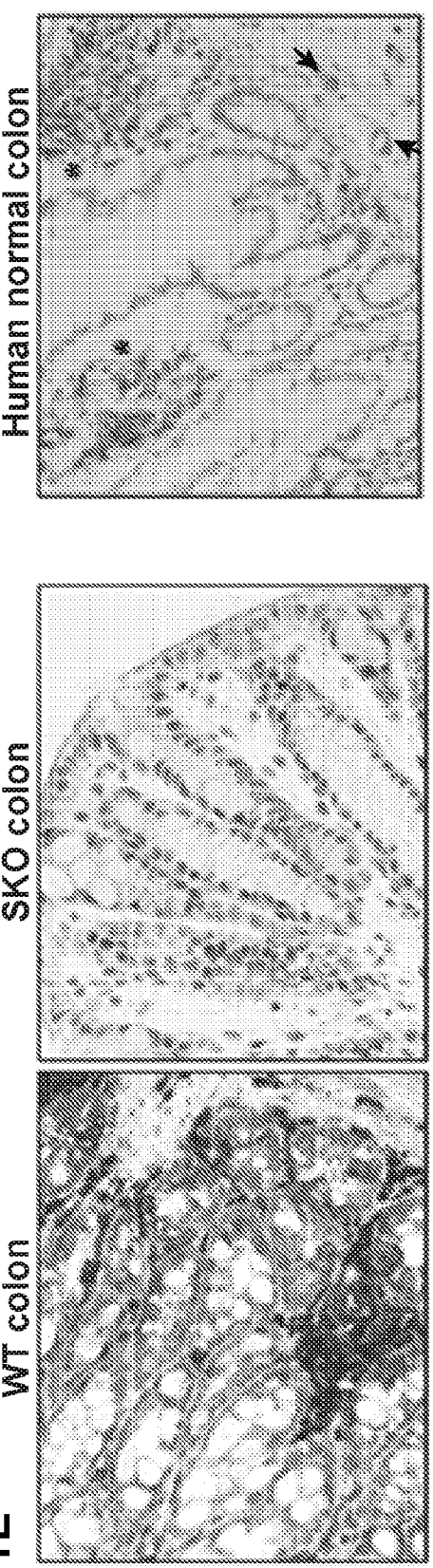

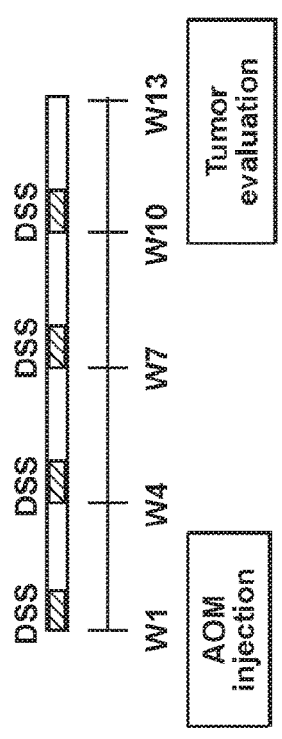
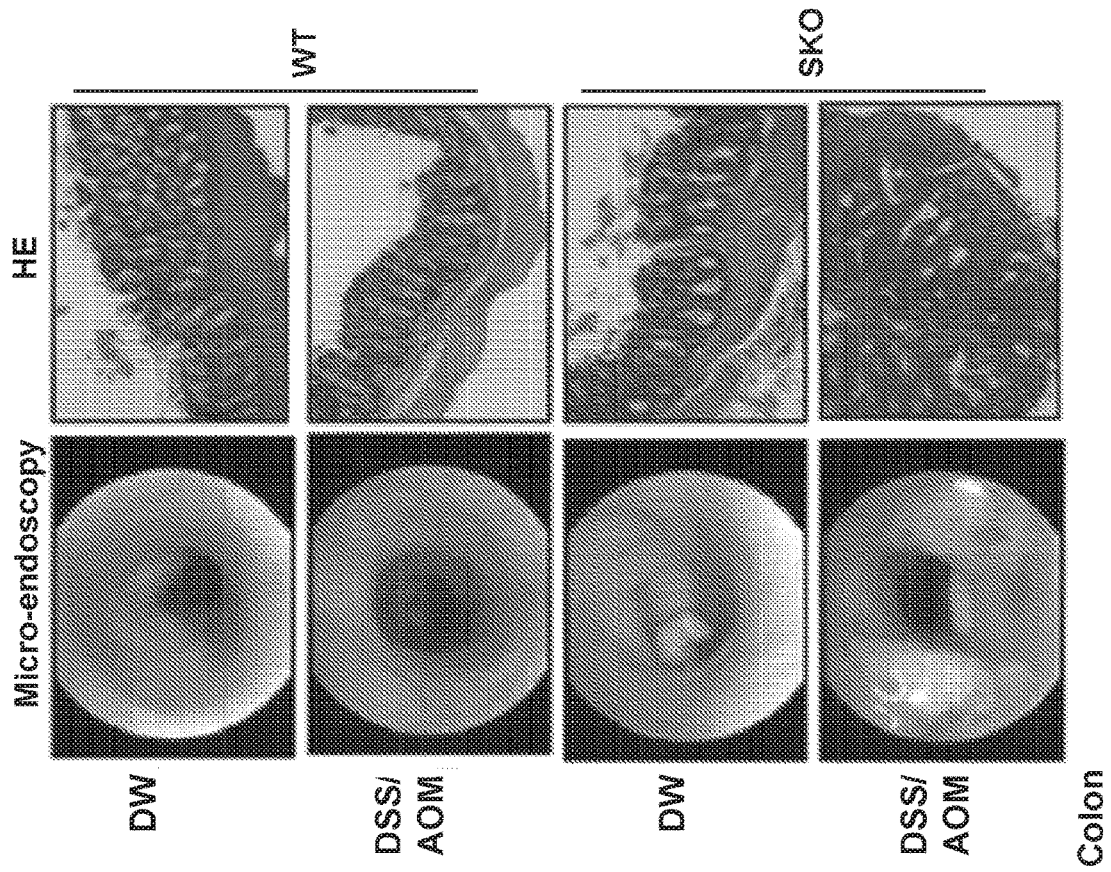
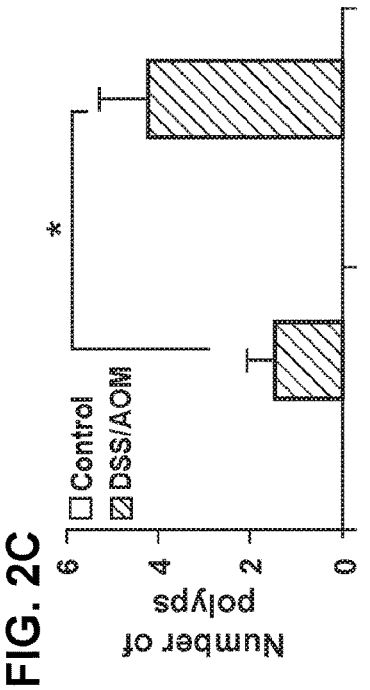
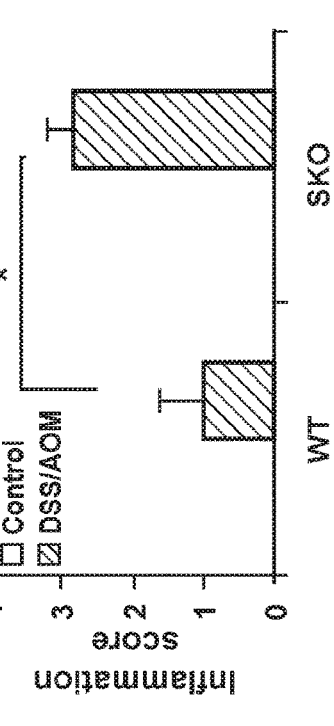
FIG. 2A
FIG. 2B
FIG. 2C
FIG. 2D

| Symbol | WT - DSS/AOM | SKO-DW | SKO - DSS/AOM |
|---|---|---|---|
| 1810030J14Rik | 148.69 | 31.43 | 5.59 |
| 1810030J14Rik | 58.01 | 12.10 | 3.17 |
| Atp12a | 28.63 | 9.28 | 18.66 |
| LOC673501 | 28.13 | 5.32 | 5.11 |
| Falm3 | 24.57 | 1.19 | 2.42 |
| LOC100047788 | 17.66 | -1.19 | 1.09 |
| Cd79b | 16.98 | 1.09 | 1.56 |
| Fcrla | 16.82 | 1.04 | 1.64 |
| Ighg | 16.59 | -1.30 | 1.31 |
| Insl5 | 15.42 | 3.84 | 1.79 |
| Cxcl13 | 14.57 | 1.14 | 1.40 |
| AI324046 | 14.06 | 1.06 | 1.00 |
| H2-Ab1 | 13.72 | 1.01 | 5.73 |
| Dlk1 | 13.20 | 1.92 | 1.08 |
| LOC100046120 | 13.03 | 1.77 | 10.49 |
| LOC100047815 | 12.86 | 1.35 | 1.59 |
| Slpi | 12.44 | 1.64 | 18.37 |
| Cd52 | 12.37 | -1.06 | 3.56 |
| Cd52 | 11.53 | -1.41 | 2.69 |
| Cd74 | 11.17 | -1.19 | 6.07 |
| AI354703 | 11.16 | 5.50 | 4.12 |
| Cd79b | 11.13 | -1.00 | 1.42 |
| Ela1 | 10.91 | 4.65 | 4.55 |
| D930028F11Rik | 10.88 | -1.44 | 1.16 |
| Klhl6 | 10.86 | -1.05 | 2.16 |
| Klhl6 | 10.75 | -1.04 | 1.71 |
| Cd74 | 10.44 | -1.16 | 5.37 |
| H2-Oa | 10.41 | 1.11 | 1.85 |
| Lyz2 | 10.16 | -1.25 | 6.49 |
| Tbr | 10.15 | 3.69 | 3.02 |
| Fcrla | 10.11 | -1.06 | 1.35 |
| B3gnt7 | 9.54 | 3.77 | 5.13 |
| Adh1 | 9.51 | 2.01 | 1.41 |
| Tnfrsf13c | 9.50 | 1.05 | 1.39 |
| B3gnt7 | 9.48 | 2.88 | 10.19 |
| Ctse | 9.42 | 3.35 | 10.23 |
| Coroia | 9.21 | -1.13 | 2.84 |
| AI324046 | 9.19 | -1.09 | -1.08 |
| Igh-6 | 9.19 | -1.22 | 1.51 |
| Fcrla | 9.17 | 1.05 | 1.42 |
| Ccr6 | 9.10 | 1.14 | 1.79 |
| Dok3 | 9.06 | 1.19 | 2.40 |
| H2-Cb | 8.95 | 1.11 | 1.23 |
| MfgeB | 8.82 | 1.16 | 4.50 |
| Igh-6 | 8.42 | -1.29 | 1.38 |
| Arhgdb | 8.39 | -1.22 | 2.89 |
| Coroia | 8.08 | -1.35 | 2.70 |
| H2-DMb2 | 7.93 | -1.12 | 2.99 |
| Hvcn1 | 7.91 | 1.12 | 1.95 |
| NtSe | 7.89 | 3.49 | 12.67 |
| MfgeB | 7.85 | 1.11 | 4.29 |

FIG. 2E-2 dsDNA90 Induced Gene Fold Changes

| Symbol | FHC | SW480 | LoVo | HT116 | COLO205 |
|---|---|---|---|---|---|
| IFIT2 | 148.10 | 6.80 | 15.94 | -1.03 | 17.08 |
| CXCL10 | 99.14 | -1.01 | 1.01 | -1.10 | 1.02 |
| OASL | 78.66 | 4.65 | 13.68 | -1.07 | 2.33 |
| CXCL11 | 45.82 | -1.10 | 1.03 | 1.01 | -1.07 |
| CH25H | 43.24 | 1.25 | -1.09 | -1.03 | -1.10 |
| IFIT3 | 40.96 | 4.96 | 14.54 | -1.12 | 9.86 |
| RSAD2 | 40.27 | 1.26 | 2.00 | -1.04 | 1.31 |
| HERC5 | 38.37 | 2.11 | 4.80 | -1.08 | 1.22 |
| CCL5 | 35.06 | 2.13 | 1.70 | -1.12 | 1.17 |
| IFIT3 | 33.88 | 3.81 | 13.04 | 1.06 | 5.85 |
| OASL | 27.57 | 1.85 | 9.14 | -1.06 | 1.68 |
| CEACAM1 | 25.25 | 1.98 | 5.28 | -1.22 | 1.33 |
| CCL6 | 17.03 | 1.36 | 1.38 | -1.09 | 1.13 |
| CEACAM1 | 16.23 | 1.55 | 3.91 | -1.04 | 1.28 |
| IFIT1 | 14.75 | 6.73 | 21.02 | -1.06 | 12.99 |
| FAM48A | 13.79 | 1.46 | 1.32 | -1.03 | 1.17 |
| PMAIP1 | 13.45 | 1.83 | 3.91 | -1.04 | 2.04 |
| IFIT3 | 13.40 | 1.94 | 7.24 | 1.02 | 3.18 |
| IFIT1 | 13.10 | 1.38 | 2.60 | -1.06 | 1.46 |
| IFNB1 | 11.39 | 1.07 | -1.16 | -1.03 | 1.04 |
| IFIH1 | 10.75 | 1.58 | 3.16 | -1.12 | 1.57 |
| PMAIP1 | 9.64 | 1.59 | 2.50 | 1.02 | 1.44 |
| OTUD1 | 9.57 | 1.18 | 1.57 | 1.08 | 1.18 |
| OTUD1 | 9.56 | 1.07 | 1.39 | -1.04 | -1.03 |
| CX3CL1 | 9.16 | -1.04 | 1.03 | 1.05 | 1.01 |
| I8G20 | 9.00 | 1.13 | 2.84 | -1.05 | 1.12 |
| PLAUR | 8.45 | 1.33 | 2.61 | 1.15 | 1.63 |
| ATF3 | 8.29 | 2.74 | 2.63 | 1.20 | 1.19 |
| RARRE83 | 7.76 | 1.54 | 2.51 | 1.03 | 1.37 |
| OAS1 | 7.76 | 1.25 | 2.22 | 1.06 | 1.32 |
| ZC3HAV1 | 7.36 | 1.70 | 5.48 | -1.07 | 1.32 |
| I8G15 | 6.83 | 2.03 | 4.24 | 1.04 | 1.60 |
| TNFSF10 | 6.73 | -1.06 | 1.20 | -1.09 | 1.29 |
| PLAUR | 6.70 | 1.18 | 2.24 | -1.04 | 1.38 |
| OAS1 | 6.57 | 1.15 | 1.99 | -1.05 | 1.28 |
| EGR1 | 6.27 | 1.70 | 1.34 | 1.04 | -1.07 |
| ZC3HAV1 | 5.94 | 1.60 | 5.13 | -1.02 | 1.30 |
| CXCL8 | 5.82 | 1.04 | 1.04 | 1.01 | -1.02 |
| IFI44 | 5.82 | 1.29 | 3.06 | -1.04 | 1.11 |
| GPR108A | 5.61 | -1.03 | -1.06 | -1.07 | 1.00 |
| DOX68 | 5.56 | 1.24 | 2.84 | 1.08 | -1.07 |
| SAMD9 | 5.34 | 1.45 | 2.69 | 1.01 | 1.06 |
| GPR108B | 5.22 | -1.11 | 1.08 | -1.08 | -1.19 |
| RAET1L | 5.19 | 1.17 | 1.60 | 1.07 | -1.01 |
| DHX68 | 5.17 | 1.15 | 2.43 | -1.05 | 1.49 |
| GCH1 | 5.05 | 1.11 | 1.16 | 1.09 | -1.24 |
| IL16 | 4.95 | 1.10 | 1.21 | -1.18 | -1.15 |
| FGF2 | 4.74 | 1.63 | 2.56 | 1.02 | 1.07 |
| CCRN4L | 4.30 | 1.19 | 1.91 | -1.01 | 1.01 |
| HERC8 | 4.29 | 1.25 | 2.22 | -1.07 | 1.11 |

FIG. 4F

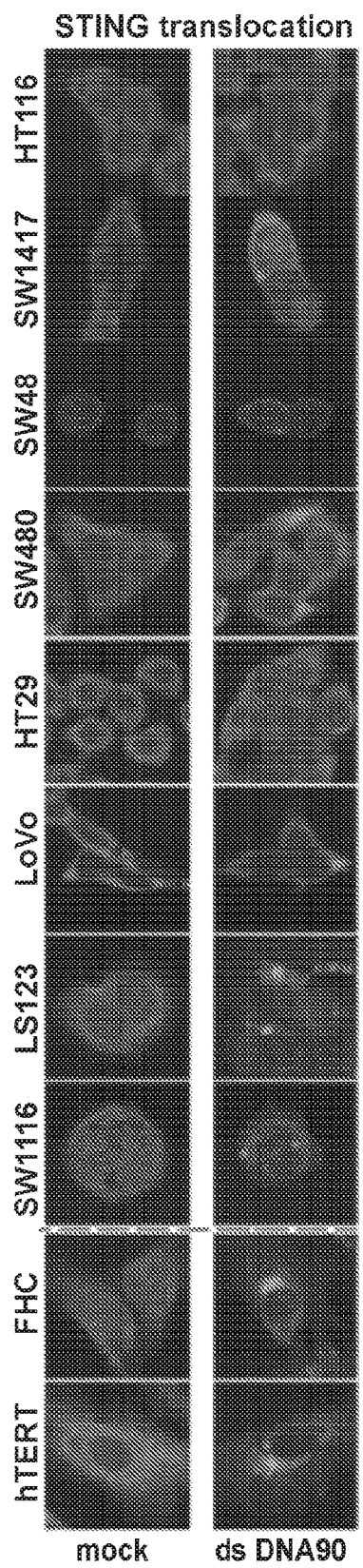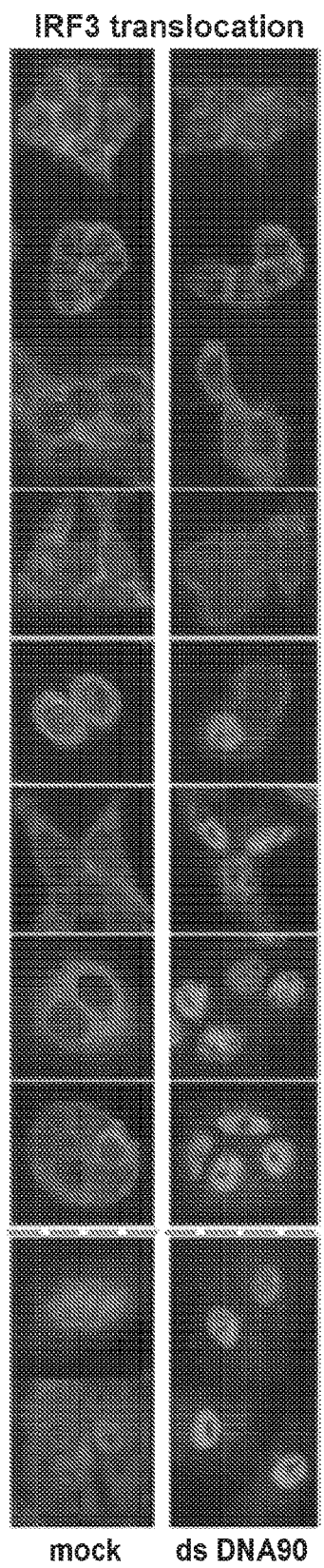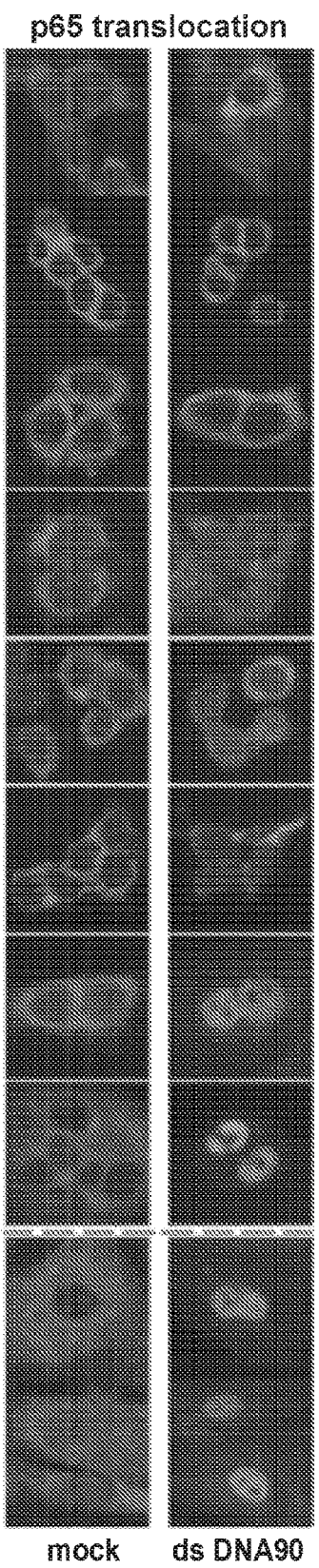

|  | | MEF-AOM | |
| --- | --- | --- | --- |
| Symbol | WT-AOM | SKO-Mock | SKO-AOM |
| EG546166 | 2.097 | 2.571 | 2.850 |
| Ifit3 | 2.064 | -2.984 | -3.111 |
| Usp18 | 1.898 | -2.500 | -2.251 |
| Rnf2 | 1.896 | 1.656 | 1.565 |
| LOC667370 | 1.871 | -1.682 | -1.741 |
| Ifit3 | 1.866 | -1.620 | -1.722 |
| Usp18 | 1.860 | -8.756 | -6.861 |
| LOC100048346 | 1.856 | -5.315 | -4.705 |
| 9930013L23RiK | 1.817 | -1.050 | -1.020 |
| Gm166 | 1.814 | 1.386 | 1.451 |
| 9530096D07RiK | 1.774 | -1.014 | 1.100 |
| C530043K16RiK | 1.745 | 1.708 | 1.555 |
| LOC674960 | 1.727 | 1.527 | -1.011 |
| LOC100038882 | 1.716 | -4.329 | -2.803 |
| V1rh12 | 1.712 | 1.288 | 1.181 |
| 5730455P16RiK | 1.703 | 1.435 | 1.470 |
| Chst5 | 1.689 | 1.202 | 1.273 |
| Fn1 | 1.685 | 1.365 | 1.520 |
| 9630025C19RiK | 1.675 | 1.220 | 1.219 |
| A530082L16RiK | 1.672 | 1.327 | 1.134 |
| S100a16 | 1.668 | -1.549 | -1.672 |
| Ndufb6 | 1.660 | 1.427 | 1.117 |
| Cd83 | 1.651 | 1.010 | 1.183 |
| 4732474K08RiK | 1.650 | 1.466 | 1.416 |
| Calm2 | 1.650 | 1.619 | 1.225 |
| AU19823 | 1.649 | 1.410 | 1.263 |
| 9130230L23RiK | 1.647 | 1.523 | 1.372 |
| 2200002D01RiK | 1.644 | 1.230 | 1.526 |
| Ogfod2 | 1.644 | 1.052 | 1.253 |
| Rnf213 | 1.642 | -2.200 | -1.438 |
| Rsad2 | 1.637 | -1.236 | -1.528 |
| Igf2bp1 | 1.636 | 1.453 | 1.325 |
| Gm50 | 1.636 | -1.189 | 1.018 |
| LOC100039693 | 1.635 | 1.396 | 1.687 |
| Peg13 | 1.623 | 1.383 | 1.348 |
| Olfr67 | 1.622 | 1.037 | -1.024 |
| Gm1381 | 1.619 | 1.222 | 1.274 |
| Igtp | 1.618 | -2.264 | -2.454 |
| Myo18b | 1.616 | 1.221 | 1.032 |
| 2700078K21RiK | 1.615 | 1.223 | 1.192 |
| 2900097C17RiK | 1.612 | 1.332 | 1.528 |
| Zc3h10 | 1.608 | 1.521 | 1.430 |
| Eif2c3 | 1.606 | 1.009 | 1.051 |
| Ensa | 1.604 | 1.106 | 1.243 |
| Ell2 | 1.603 | 1.360 | 1.070 |
| Efna5 | 1.602 | -1.058 | 1.078 |
| Chrna2 | 1.595 | 1.036 | -1.023 |
| Kctd12b | 1.595 | 1.178 | -1.111 |
| Catnb | 1.594 | 1.196 | 1.237 |
| 2410002F23RiK | 1.593 | 1.682 | 1.726 |

FIG. 7A

| Symbol | WT-DMH | MEF-DMH SKO-Mock | SKO-DMH |
|---|---|---|---|
| Rgs1 | 3.407 | -1.682 | 1.216 |
| Ccl3 | 3.038 | -1.001 | 1.470 |
| Cxcl2 | 2.822 | -1.003 | 1.769 |
| EG546166 | 2.502 | 2.571 | 1.944 |
| Rgs1 | 2.433 | -1.138 | -1.118 |
| Atf3 | 2.157 | 1.047 | 1.309 |
| Rgs1 | 2.132 | -1.399 | 1.000 |
| Gdf15 | 2.070 | -1.771 | 1.005 |
| Ccl4 | 2.069 | -1.712 | -1.098 |
| EG434760 | 1.892 | 1.282 | 1.261 |
| Aifm2 | 1.871 | 1.147 | 1.148 |
| Igtp | 1.847 | -2.264 | -2.409 |
| Sprr2a | 1.783 | -1.051 | 1.250 |
| Rab10 | 1.781 | 1.603 | 1.184 |
| Scyl1 | 1.779 | 1.938 | 1.717 |
| Zfp566 | 1.777 | 1.524 | 1.481 |
| Mcm7 | 1.758 | 1.004 | 1.015 |
| 4930476L21Rik | 1.736 | 1.353 | 1.385 |
| Sec11c | 1.715 | 1.061 | -1.130 |
| Usp18 | 1.705 | -2.500 | -2.357 |
| Ube2t | 1.703 | 1.207 | 1.992 |
| Cxcl2 | 1.694 | 1.025 | 1.496 |
| Klhdc4 | 1.691 | 1.301 | 1.071 |
| Slfn2 | 1.690 | 1.372 | 1.296 |
| Pdhb | 1.689 | -1.083 | 1.077 |
| Serhl | 1.680 | 1.474 | 1.332 |
| LOC280205 | 1.663 | 1.016 | 1.559 |
| Rdh1 | 1.659 | 1.289 | 1.050 |
| Cyp11b1 | 1.652 | -1.234 | -1.085 |
| Frag1 | 1.647 | 1.638 | 2.196 |
| Josd3 | 1.647 | 1.106 | 1.138 |
| Nkain2 | 1.643 | 1.034 | 1.008 |
| 1110059G10Rik | 1.642 | 1.063 | 1.220 |
| 1810034K20Rik | 1.639 | 1.755 | 1.375 |
| Afg3l2 | 1.638 | 1.272 | 1.149 |
| Coro1b | 1.633 | -1.090 | 1.259 |
| Rnf121 | 1.630 | 1.430 | 1.554 |
| Snx16 | 1.627 | 1.135 | 1.332 |
| Cyr61 | 1.625 | 1.472 | 1.794 |
| Gbp3 | 1.613 | -3.926 | -4.177 |
| Ngfb | 1.609 | 1.442 | 1.555 |
| LOC100038882 | 1.607 | -4.329 | -3.804 |
| Myocd | 1.605 | 1.216 | 1.396 |
| Cdkn1a | 1.603 | 1.498 | 1.608 |
| Bet1 | 1.601 | 1.572 | 1.219 |
| Asb16 | 1.599 | 1.393 | 1.365 |
| Ppm1f | 1.598 | -1.085 | 1.075 |
| 2510040D07Rik | 1.592 | 1.794 | 1.270 |
| Tapbpl | 1.587 | 1.066 | 1.255 |
| Rps6kb1 | 1.587 | 1.215 | 1.005 |

FIG. 7B

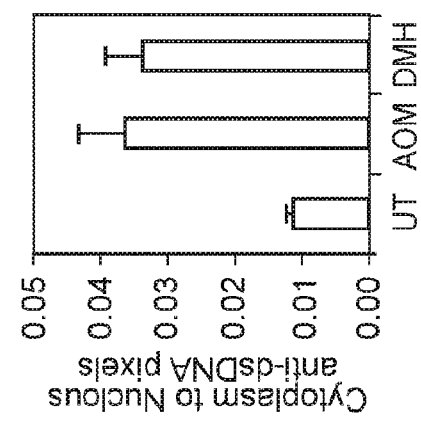
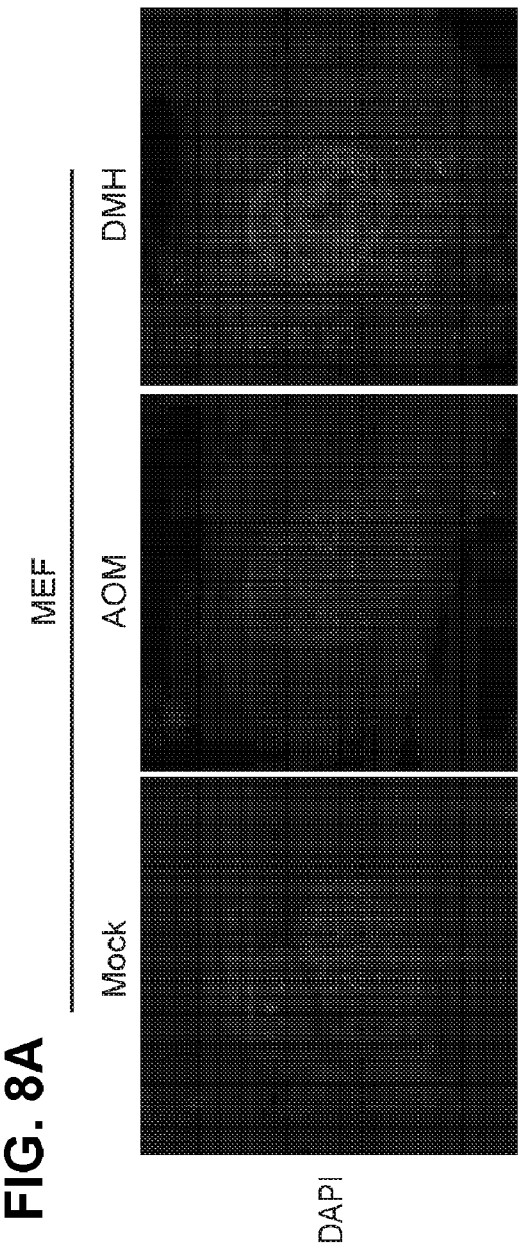
FIG. 8A
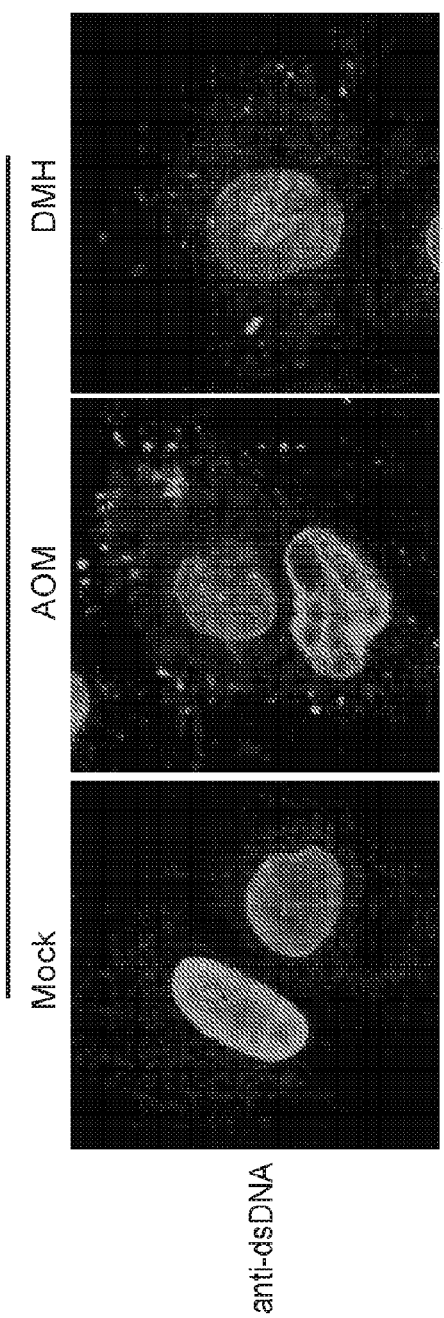
FIG. 8B

|     |         | #mouse | #polyps |
|-----|---------|--------|---------|
| WT  | Control | 1<br>2 | 0<br>0 |
|     | AOM/DDS | 1<br>2<br>3<br>4<br>5<br>6<br>7 | 2<br>0<br>0<br>1<br>0<br>1<br>2 |
| SKO | Control | 1<br>2 | 0<br>0 |
|     | AOM/DDS | 1<br>2<br>3<br>4<br>5<br>6<br>7 | 5<br>5<br>4<br>5<br>5<br>3<br>2 |

|     |         | #mouse | Inflammation Score |
|-----|---------|--------|--------------------|
| WT  | Control | 1<br>2 | 0<br>0 |
|     | AOM/DSS | 1<br>2<br>3<br>4<br>5<br>6<br>7 | ND<br>ND<br>1<br>1<br>0<br>1<br>2 |
| SKO | Control | 1<br>2 | 0<br>0 |
|     | AOM/DSS | 1<br>2<br>3<br>4<br>5<br>6<br>7 | ND<br>ND<br>3<br>2<br>3<br>3<br>3 |

Transcription Factor Binding Sites in IL 18 Promoter

| TF | Position | Binding Sequence | |
|---|---|---|---|
| IRF-1 | 112025721 | TAAAGTAAAGCGTATTGTCAATAAATTTCATTGCCACAAAG | SEQ ID NO: 1 |
| | 112030068 | GAAACTCTGTCAACACCACCACCACCAAGAACAAAAGA | SEQ ID NO: 2 |
| | 112034210 | GAGGCTACATTCTGTGCAATATTGCAATAGTCTGAATGCAA | SEQ ID NO: 3 |
| NF-KB | 112038354 | CGCGTTGAGAAGAGAGGAGAAGACTAGAAGGAGACAGCTGCA | SEQ ID NO: 4 |
| | 112039068 | CCGAATTTATGGAAAAGTAAAAGTAAAATTTGAAGCTACTT | SEQ ID NO: 5 |
| STAT1 | 112046243 | GAGGGACAGTCCAGGCAGTTCTGTTGCGTTTCACTGTTTAG | SEQ ID NO: 6 |
| IRF-7 | 112027291 | TCTCCCATCTTAGCCTGGGACTCCCATCTGGGACCACAGAT | SEQ ID NO: 7 |
| | 112036090 | GATTAAGAATACATACGTGACTCAAGTTGAAATAGTAAGTTT | SEQ ID NO: 8 |

FIG. 12

| Cell | Type | Response to dsDNA90 | | | | | TF Activation | | |
|---|---|---|---|---|---|---|---|---|---|
| | | STING | cGas | Gene Up Regulation | | | IRF3 | TBK1 | p65 |
| | | | | IFNB | CXCL10 | | | | |
| FHC | normal colon epithelial | + | + | + | + | | + | + | + |
| SW116 | colorectal adenocarcinoma Dukes' type A, grade III | + | + | + | + | | + | + | + |
| LS123 | Dukes' type B | + | - | - | - | | + | + | + |
| LS 174T | Dukes' type B | + | - | - | - | | - | - | - |
| SW480 | Dukes' type B | + | + | - | - | | - | - | - |
| SW948 | Dukes' type C, grade III | + | + | - | - | | ND | ND | - |
| SW1417 | Dukes' type C, grade III | - | - | - | - | | - | - | - |
| LoVo | Dukes' type C, grade IV | + | + | Weakly | Weakly | | - | + | + |
| SW48 | Dukes' type C, grade IV | - | - | - | - | | - | - | - |
| HT29 | | + | + | Weakly | + | | + | + | + |
| HT116 | | - | - | Weakly | Weakly | | ND | ND | - |
| COLO205 | Dukes' type D | + | + | - | - | | - | - | - |

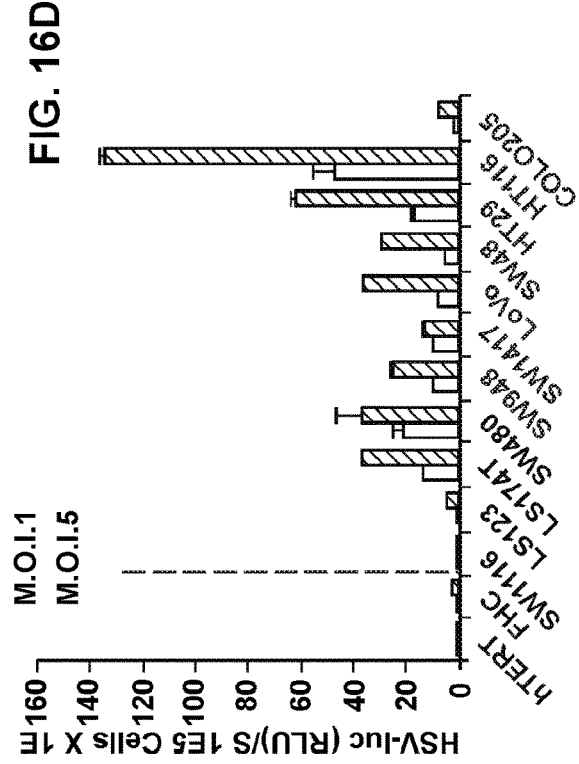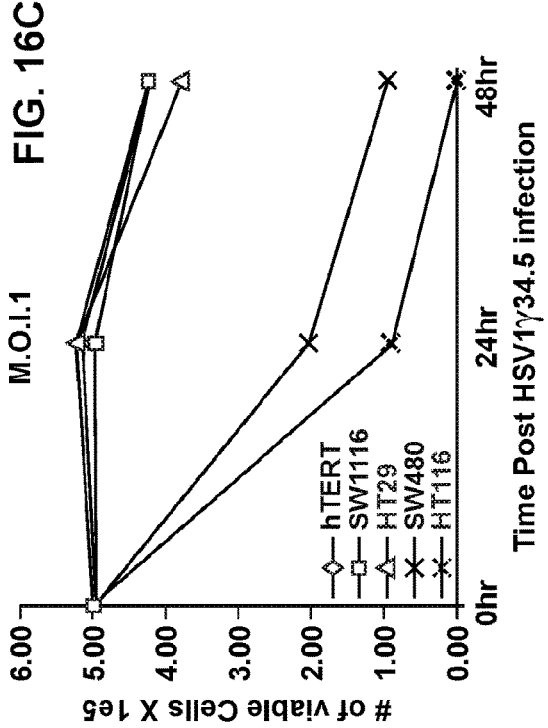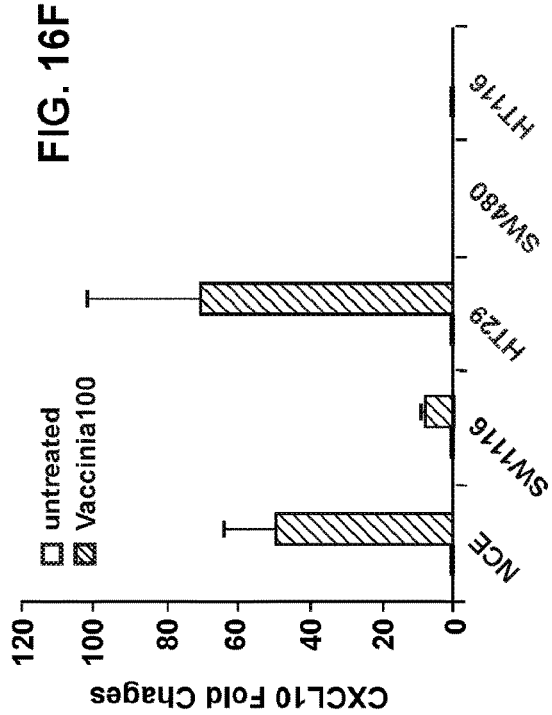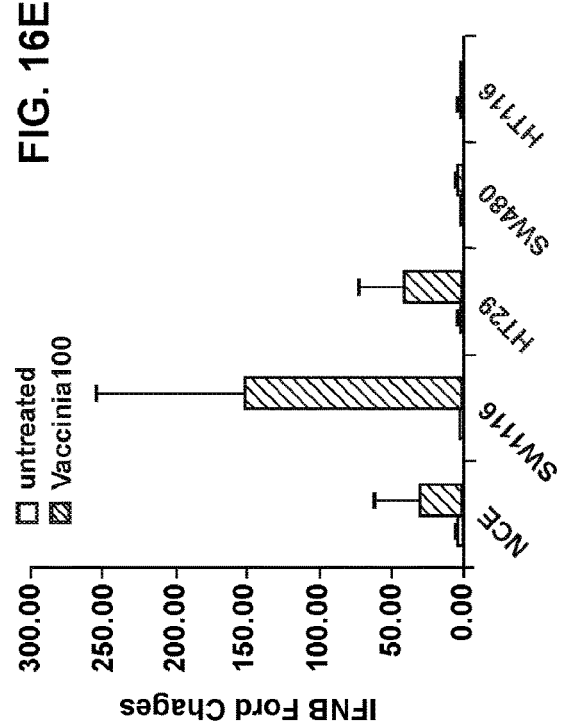

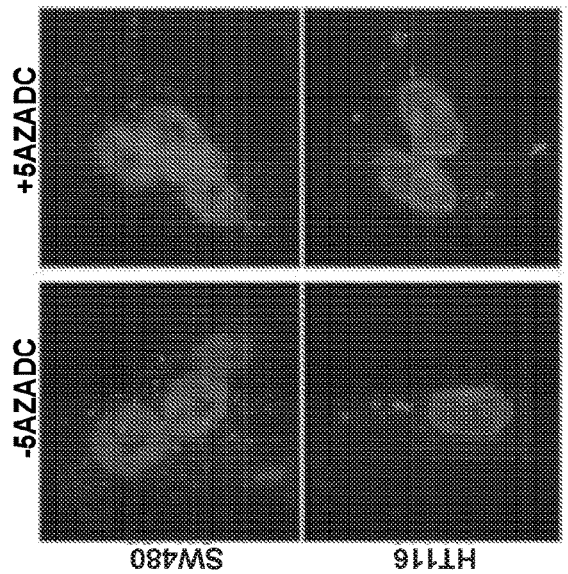
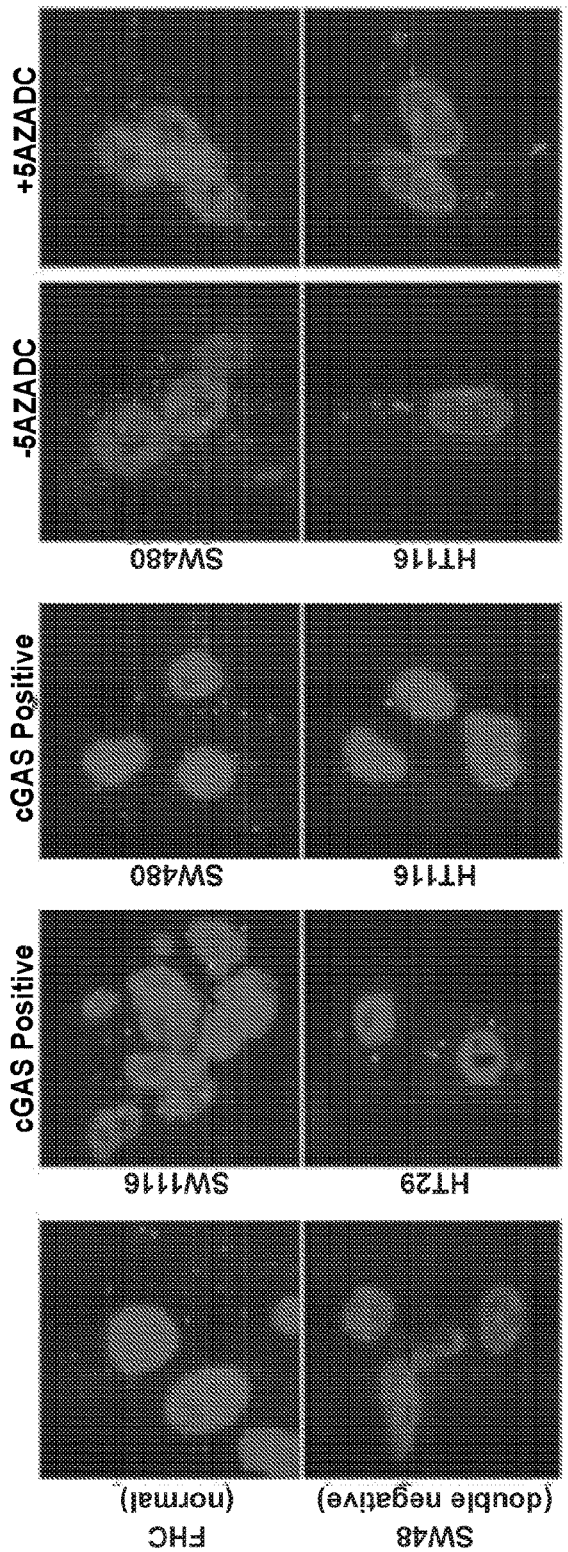
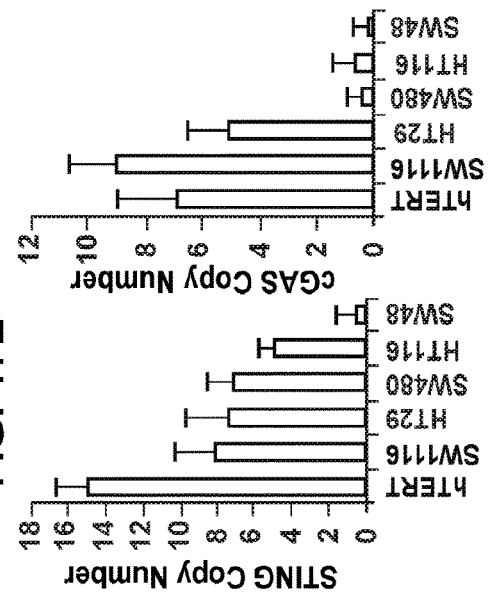
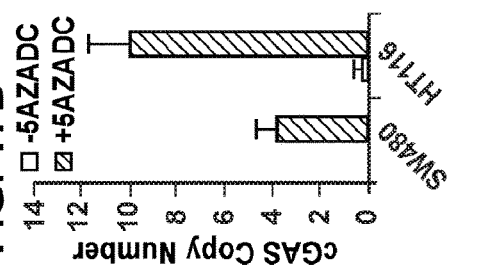
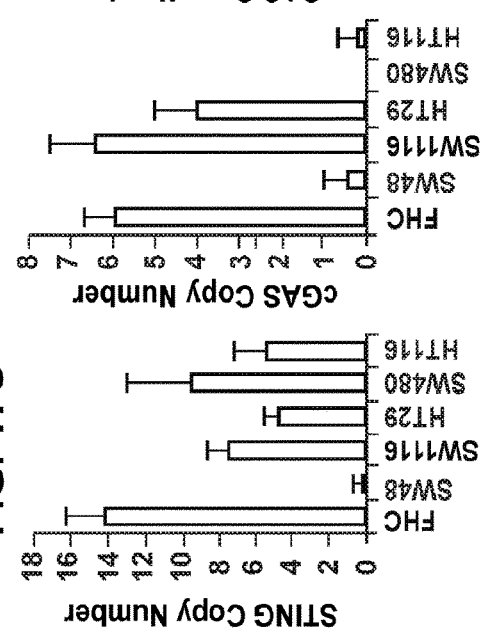
FIG. 17A
FIG. 17B
FIG. 17C
FIG. 17D
FIG. 17E

2-Plex RNAscope analysis of STING and cGAS in Colon Cancer TMA

| tissue type | Normal | | Colon Adenocarcinoma | |
|---|---|---|---|---|
| | # of tissues | Percentage | # of tissues | Percentage |
| STING+cGAS+ | 12 | 100% | 50 | 63% |
| STING+cGAS- | 0 | | 12 | 15% |
| STING-cGAS+ | 0 | | 11 | 14% |
| STING-cGAS- | 0 | | 7 | 9% | cGAS Positive cGAS Negative

FIG. 24

| Sample Name | Age | Gender | Ethnicity | Colon Cancer Grade | Target Region | Position in Target | Ref. Base | Variant Found | Variant Name | Variant Class | Variant Function | Reference Codon | Variant Codon |
|---|---|---|---|---|---|---|---|---|---|---|---|---|---|
| FHC | | | normal | | TMEM173_Exon3 | 144 | G | S | rs7447927 | SNP | Coding, Synon. | GTG-Val | GTC-Val |
| | | | | | TMEM173_Exon6 | 175 | A | G | rs1131769 | SNP | Coding, Non-Synon. | CAT-His | CGT-Arg |
| SW1116 | 73 | Male | Caucasian | Dukes' type A, grade III | TMEM173_Exon3 | 144 | G | C | rs7447927 | SNP | Coding, Synon. | GTG-Val | GTC-Val |
| | | | | | TMEM173_Exon6 | 175 | A | G | rs1131769 | SNP | Coding, Non-Synon. | CAT-His | CGT-Arg |
| LS123 | 65 | Female | Caucasian | Dukes' type B | TMEM173_Exon3 | 144 | G | C | rs7447927 | SNP | Coding, Synon. | GTG-Val | GTC-Val |
| | | | | | TMEM173_Exon6 | 175 | A | G | rs1131769 | SNP | Coding, Non-Synon. | CAT-His | CGT-Arg |
| LS174T | 58 | Female | Caucasian | Dukes' type B | TMEM173_Intron1 | 16 | C | T | rs80059114 | SNP | UTR | | |
| | | | | | TMEM173_Exon3 | 144 | G | C | rs7447927 | SNP | Coding, Synon. | GTG-Val | GTC-Val |
| | | | | | TMEM173_Exon6 | 175 | A | G | rs1131769 | SNP | Coding, Non-Synon. | CAT-His | CGT-Arg |
| SW480 | 50 | Male | Caucasian | Dukes' type B | TMEM173_Exon3 | 144 | G | S | rs7447927 | SNP | Coding, Synon. | GTG-Val | GTC-Val |
| | | | | | TMEM173_Intron4 | 212 | G | R | rs11554776 | SNP | Coding, Non-Synon. | CGC-Arg | CAC-His |
| | | | | | TMEM173_Exon6 | 140 | G | R | rs7390272 | SNP | Intronic | | |
| | | | | | TMEM173_Exon6 | 169 | G | S | rs78233829 | SNP | Coding, Non-Synon. | CGC-Arg | GCT-Ala |
| | | | | | TMEM173_Exon6 | 175 | A | G | rs1131769 | SNP | Coding, Non-Synon. | CAT-His | CGT-Arg |
| | | | | | TMEM173_Intron6 | 3 | A | R | rs75746446 | SNP | Intronic | | |
| | | | | | TMEM173_Exon7 | 119 | G | R | rs7390824 | SNP | Coding, Non-Synon. | CGG-Arg | CAG-Gln |
| | | | | | TMEM173_Intron7 | 52 | G | S | rs73257329 | SNP | Intronic | | |
| SW948 | 81 | Female | Caucasian | Dukes' type C, grade III | TMEM173_Intron1 | 16 | C | Y | rs80059114 | SNP | UTR | | |
| | | | | | TMEM173_Exon3 | 144 | G | S | rs7447927 | SNP | Coding, Synon. | GTG-Val | GTC-Val |
| | | | | | TMEM173_Exon6 | 175 | A | R | rs1131769 | SNP | Coding, Non-Synon. | CAT-His | CGT-Arg |
| SW1417 | 53 | Female | Caucasian | Dukes' type C, grade III | TMEM173_Exon3 | 144 | G | S | rs7447927 | SNP | Coding, Synon. | GTG-Val | GTC-Val |
| | | | | | TMEM173_Exon6 | 175 | A | R | rs1131769 | SNP | Coding, Non-Synon. | CAT-His | CGT-Arg |
| LOVO | 56 | Male | | Dukes' type C, grade IV | TMEM173_Exon3 | 144 | G | S | rs7447927 | SNP | Coding, Synon. | GTG-Val | GTC-Val |
| | | | | | TMEM173_Intron4 | 212 | G | R | rs11554776 | SNP | Coding, Non-Synon. | CGC-Arg | CAC-His |
| | | | | | TMEM173_Exon6 | 140 | A | R | rs7390272 | SNP | Intronic | | |
| | | | | | TMEM173_Exon6 | 169 | G | S | rs78233829 | SNP | Coding, Non-Synon. | CGC-Arg | GCT-Ala |
| | | | | | TMEM173_Exon6 | 175 | A | G | rs1131769 | SNP | Coding, Non-Synon. | CAT-His | CGT-Arg |
| | | | | | TMEM173_Intron6 | 3 | A | R | rs75746446 | SNP | Intronic | | |
| | | | | | TMEM173_Exon7 | 119 | G | R | rs7360824 | SNP | Coding, Non-Synon. | CGG-Arg | CAG-Gln |
| | | | | | TMEM173_Intron7 | 52 | G | S | rs73257329 | SNP | Intronic | | |
| SW48 | 82 | Female | Caucasian | Dukes' type C, grade IV | TMEM173_Intron1 | 16 | C | Y | rs80059114 | SNP | UTR | | |
| | | | | | TMEM173_Exon3 | 144 | G | C | rs7447927 | SNP | Coding, Synon. | GTG-Val | GTC-Val |
| | | | | | TMEM173_Exon3 | 226 | A | R | Novel | SNP | Coding, Non-Synon. | AG-Arg | GG-His |
| | | | | | TMEM173_Exon6 | 175 | A | G | rs1131769 | SNP | Coding, Non-Synon. | CAT-His | CGT-Arg |
| HT29 | 44 | Female | | colorectal adenocarcinoma | TMEM173_Exon3 | 144 | G | C | rs7447927 | SNP | Coding, Synon. | GTG-Val | GTC-Val |
| | | | | | TMEM173_Exon6 | 175 | A | C | rs1131769 | SNP | Coding, Non-Synon. | CAT-His | CGT-Arg |
| HT116 | adult | Male | Caucasian | colorectal carcinoma | TMEM173_Exon3 | 144 | G | C | rs7447927 | SNP | Coding, Synon. | GTG-Val | GTC-Val |
| | | | | | TMEM173_Exon6 | 175 | A | G | rs1131769 | SNP | Coding, Non-Synon. | CAT-His | CGT-Arg |
| Colo205 | 70 | Male | Caucasian | Dukes' type D | TMEM173_Exon3 | 144 | G | S | rs7447927 | SNP | Coding, Synon. | GTG-Val | GTC-Val |
| | | | | | TMEM173_Exon6 | 175 | A | R | rs1131769 | SNP | Coding, Non-Synon. | CAT-His | CGT-Arg |

| Sample Name | Age | Gender | Ethnicity | Colon Cancer Grade | Target Region | Position in Target | Ref. Base | Variant Found | Variant Name | Variant Class | Variant Function | Reference Codon | Variant Codon |
|---|---|---|---|---|---|---|---|---|---|---|---|---|---|
| FHC | | | | normal | ME21D1_Exon5_2 | 70 | G | A | rs311678 | SNP | Coding, Synon. | AAG=Lys | AAA=Lys |
| | | | | | ME21D1_Exon1_1 | 243 | C | A | rs9352000 | SNP | Coding, Non-Synon. | ACC=Thr | AAC=Asn |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | M | rs610913 | SNP | Coding, Non-Synon. | CCT=Pro | CAT=His |
| | | | | | ME21D1_Exon4 | 32 | C | Y | rs73754628 | SNP | Coding, Synon. | ATC=Ile | ATT=Ile |
| SW1116 | 73 | Male | Caucasian | Dukes'type A, grade III | ME21D1_Exon1_1 | 243 | C | A | rs9352000 | SNP | Coding, Non-Synon. | ACC=Thr | AAC=Asn |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | A | rs610913 | SNP | Coding, Non-Synon. | CCT=Pro | CAT=His |
| | | | | | ME21D1_Exon5_2 | 70 | G | A | rs311678 | SNP | Coding, Synon. | AAG=Lys | AAA=Lys |
| LS123 | 65 | Female | Caucasian | Dukes'type B | ME21D1_Exon1_1 | 243 | C | A | rs9352000 | SNP | Coding, Non-Synon. | ACC=Thr | AAC=Asn |
| | | | | | ME21D1_Exon1_2 | 11 | C | M | rs35629782 | SNP | Coding, Non-Synon. | GCG=Ala | GAG=Glu |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | A | rs610913 | SNP | Coding, Non-Synon. | CCT=Pro | CAT=His |
| | | | | | ME21D1_Exon5_2 | 70 | G | R | rs311678 | SNP | Coding, Synon. | AAG=Lys | AAA=Lys |
| LS174T | 58 | Female | Caucasian | Dukes'type B | ME21D1_Exon1_1 | 243 | C | A | rs9352000 | SNP | Coding, Non-Synon. | ACC=Thr | AAC=Asn |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | A | rs610913 | SNP | Coding, Non-Synon. | CCT=Pro | CAT=His |
| | | | | | ME21D1_Exon5_2 | 70 | G | A | rs311678 | SNP | Coding, Synon. | AAG=Lys | AAA=Lys |
| SW480 | 50 | Male | Caucasian | Dukes'type B | ME21D1_Exon1_1 | 33 | T | - | rs34413328 | Deletion | UTR | | |
| | | | | | ME21D1_Exon1_1 | 243 | C | M | rs9352000 | SNP | Coding, Non-Synon. | ACC=Thr | AAC=Asn |
| | | | | | ME21D1_Exon1_3 | 11 | T | Y | rs9446904 | SNP | Coding, Synon. | CCT=Pro | CCC=Pro |
| | | | | | ME21D1_Exon5_2 | 70 | G | R | rs311678 | SNP | Coding, Synon. | AAG=Lys | AAA=Lys |
| SW948 | 81 | Female | Caucasian | Dukes'type C, grade III | ME21D1_Exon1_1 | 243 | C | M | rs9352000 | SNP | Coding, Non-Synon. | ACC=Thr | AAC=Asn |
| | | | | | ME21D1_Exon1_3 | 11 | T | Y | rs9446904 | SNP | Coding, Synon. | CCT=Pro | CCC=Pro |
| | | | | | ME21D1_Exon2 | 125 | C | M | rs610913 | SNP | Coding, Non-Synon. | CCT=Pro | CAT=His |
| | | | | | ME21D1_Exon5_2 | 70 | G | A | rs311678 | SNP | Coding, Synon. | AAG=Lys | AAA=Lys |
| SW1417 | 53 | Female | Caucasian | Dukes'type C, grade III | ME21D1_Exon1_1 | 243 | C | A | rs9352000 | SNP | Coding, Non-Synon. | ACC=Thr | AAC=Asn |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | A | rs610913 | SNP | Coding, Non-Synon. | CCT=Pro | CAT=His |
| | | | | | ME21D1_Exon5_2 | 70 | G | A | rs311678 | SNP | Coding, Synon. | AAG=Lys | AAA=Lys |
| LOVO | 56 | Male | | Dukes'type C, grade IV | ME21D1_Exon1_1 | 33 | T | HD | rs34413328 | Deletion | UTR | | |
| | | | | | ME21D1_Exon1_1 | 243 | C | M | rs9352000 | SNP | Coding, Non-Synon. | ACC=Thr | AAC=Asn |
| | | | | | ME21D1_Exon1_3 | 11 | T | Y | rs9446904 | SNP | Coding, Synon. | CCT=Pro | CCC=Pro |
| | | | | | ME21D1_Exon5_2 | 70 | G | R | rs311678 | SNP | Coding, Synon. | AAG=Lys | AAA=Lys |
| SW48 | 82 | Female | Caucasian | Dukes'type C, grade IV | ME21D1_Exon1_1 | 33 | T | HD | rs34413328 | Deletion | UTR | | |
| | | | | | ME21D1_Exon1_1 | 243 | C | M | rs9352000 | SNP | Coding, Non-Synon. | ACC=Thr | AAC=Asn |
| | | | | | ME21D1_Exon5_2 | 70 | G | R | rs311678 | SNP | Coding, Synon. | AAG=Lys | AAA=Lys |
| HT29 | 44 | Female | Caucasian | colorectal adenocarcinoma | ME21D1_Exon1_1 | 243 | C | M | rs9352000 | SNP | Coding, Non-Synon. | ACC=Thr | AAC=Asn |
| HT116 | adult | Male | | colorectal carcinoma | ME21D1_Exon1_1 | 33 | T | HD | rs34413328 | Deletion | UTR | | |
| | | | | | ME21D1_Exon1_1 | 243 | C | A | rs9352000 | SNP | Coding, Non-Synon. | ACC=Thr | AAC=Asn |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | M | rs610913 | SNP | Coding, Non-Synon. | CCT=Pro | CAT=His |
| | | | | | ME21D1_Exon4 | 15 | C | S | Novel | SNP | Coding, Non-Synon. | CTA=Leu | GTA=Val |
| | | | | | ME21D1_Exon5_2 | 70 | G | R | rs311678 | SNP | Coding, Synon. | AAG=Lys | AAA=Lys |
| Colo205 | 70 | Male | Caucasian | Dukes'type D | ME21D1_Exon1_1 | 243 | C | A | rs9352000 | SNP | Coding, Non-Synon. | ACC=Thr | AAC=Asn |
| | | | | | ME21D1_Exon1_3 | 11 | T | C | rs9446904 | SNP | Coding, Synon. | CCT=Pro | CCC=Pro |
| | | | | | ME21D1_Exon2 | 125 | C | A | rs610913 | SNP | Coding, Non-Synon. | CCT=Pro | CAT=His |
| | | | | | ME21D1_Exon5_2 | 70 | G | A | rs311678 | SNP | Coding, Synon. | AAG=Lys | AAA=Lys |

Fig. 25

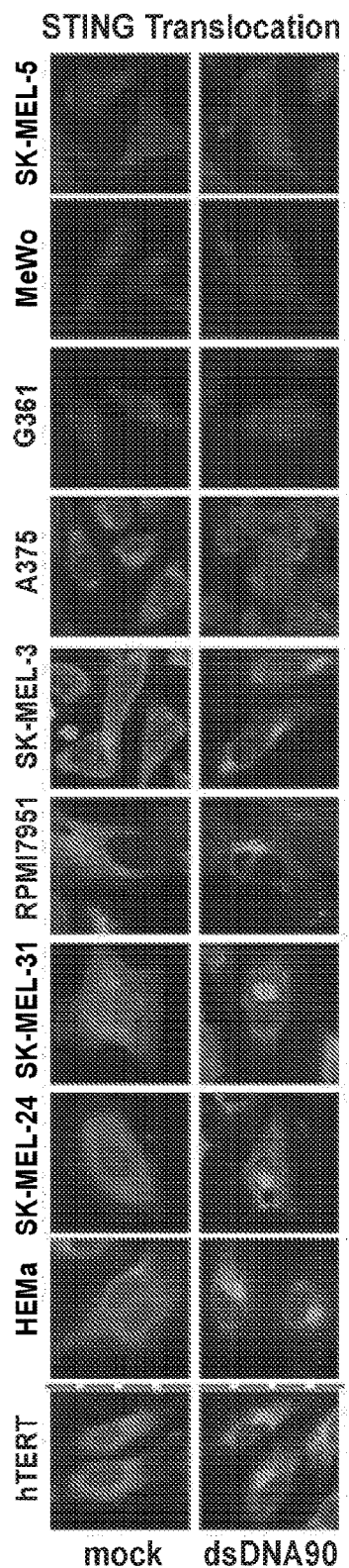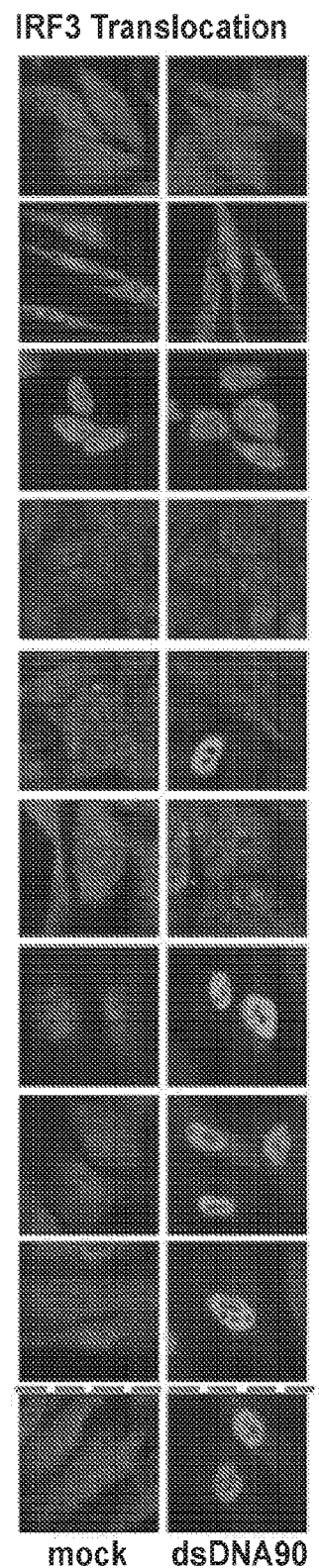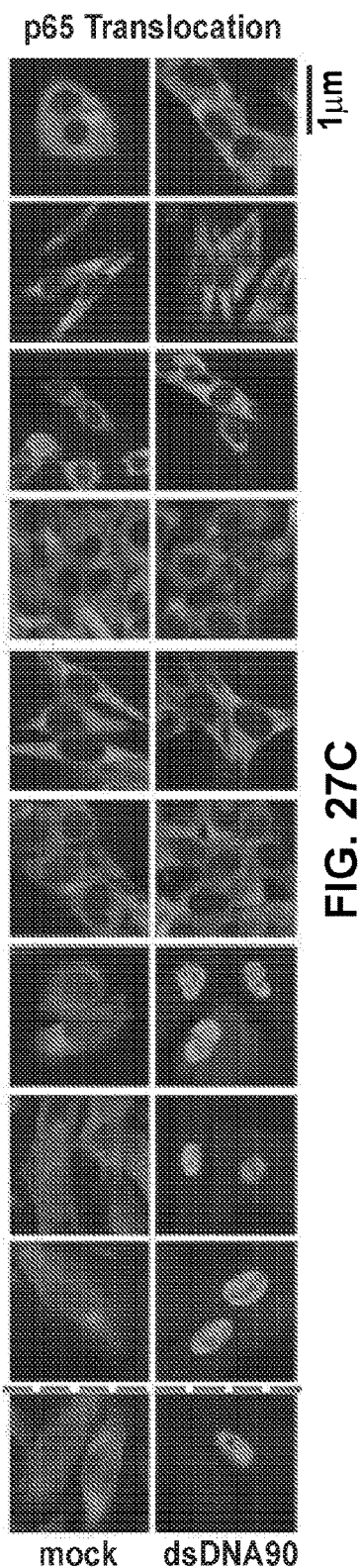

SEQUENCE LISTING

```
<160> NUMBER OF SEQ ID NOS: 8

<210> SEQ ID NO 1
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IRF-1 Position 112025721

<400> SEQUENCE: 1
taaagtaaag cgtattgtca ataaatttca ttgccacaaa g         41

<210> SEQ ID NO 2
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IRF-1 Position 112030068

<400> SEQUENCE: 2
gaaactctgt caacaccacc accaccacca agaacaaaag a         41

<210> SEQ ID NO 3
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IRF-1 Position 112034210

<400> SEQUENCE: 3
gaggctacat tctgtgcaat attgcaatag tctgaatgca a         41

<210> SEQ ID NO 4
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: NF-KB Position 112038354

<400> SEQUENCE: 4
cgcgttgaga agagggagaa gactagaagg agacagctgc a         41

<210> SEQ ID NO 5
```

```
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: NF-KB Position 112039068

<400> SEQUENCE: 5
ccgaatttat ggaaaagtaa aagtaaaatt tgaagctact t                              41

<210> SEQ ID NO 6
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: STAT1 Position 112046243

<400> SEQUENCE: 6
gagggacagt ccaggcagtt ctgtgcgtgt tcactgttta g                              41

<210> SEQ ID NO 7
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IRF-7 Position 112027291

<400> SEQUENCE: 7
tctcccatct tagcctggga ctcccatctg ggaccacaga t                              41

<210> SEQ ID NO 8
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: IRF-7 Position 112036090

<400> SEQUENCE: 8
gataagaata catacgtgac tcaagttgaa atagtaagtt t                              41
```

CANCER TREATMENT AND DIAGNOSIS

CROSS-REFERENCE TO RELATED APPLICATIONS

This application is a Continuation Application of U.S. patent application Ser. No. 15/735,502, filed Dec. 11, 2017, now Abandoned, which is a U.S. National Phase Application of PCT/US2016/037288, filed Jun. 13, 2016, which claims the priority benefit of U.S. Provisional Patent Application No. 62/174,374, filed Jun. 11, 2015, herein incorporated by reference in its entirety.

STATEMENT AS TO FEDERALLY SPONSORED RESEARCH

This invention was made with government support under Grant Number R01 AI079336-05 awarded by the National Institute of Allergy and Infection Diseases (NIAID). The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 49720_Seqlisting.txt; Size: 2,313 bytes, created: Jun. 13, 2016.

FIELD OF THE INVENTION

The present disclosure relates generally to the fields of molecular biology, immunology, biochemistry, cancer, and medicine. More particularly, the disclosure relates to methods for diagnosis and treatment of cancer through the use of a cellular protein.

BACKGROUND

Cancer is a leading cause of death in the United States of America and elsewhere. New treatments and diagnostics are needed to improve outcomes.

Colorectal cancer (CRC) affects about 1.2 million people in the United States with approximately 150,000 new cases being diagnosed every year. Indeed, CRC is the third most common cause of cancer worldwide, after lung and breast cancer, and the second leading cause of cancer death in adults (DeSantis et al., 2014). Intestine-associated malignant disease frequently develops from colonic epithelial cells that accumulate genetic alterations in key genes involved in the control of cell growth. Multistep genomic damage aggravated alterations can be acquired from environmental factors comprising carcinogens or from genotoxic microbial pathogens including *Helicobacter pylori* (Arthur et al., 2014; Kim and Chang, 2014; Louis et al., 2014). Such genetic amendments frequently involve activation of cell growth signaling through mutation of k-ras as well as through mutation or epigenetic silencing of critical tumor suppressor genes (TSGs) such as p53 and adenomatous polyposis coli (APC). Mutated TSGs such as APC can also be inherited, thus increasing the risk of CRC significantly (Fearon, 2011).

Orally administered carcinogens such as the DNA-adduct forming azoxymethane (AOM) induce genomic changes in gastrointestinal epithelial cells, an event which can trigger the activation of DNA damage response (DDR) pathways. While these responses involve repairing DNA breaks and eliminating base mismatches, they can also include activating the production of pro-inflammatory cytokines which alerts the immune surveillance system to the damaged area and facilitates wound repair. For example, using murine models, it has been demonstrated that the administration of AOM followed by inflammatory drug dextran sulphate sodium (DSS) can cause epithelial cells to produce IL-1β and IL-18 which becomes processed by the inflammasome, a multiprotein complex comprising nucleotide-binding oligomerization-domain protein like receptors (NLRs) such as NLRP3 and NLRP6 as well as apoptotic speck protein containing a CARD (ASC/PYCARD) and caspase-1, for secretion (Arthur et al., 2012; Elinav et al., 2011). IL-18, for example, can bind to colonic dendritic cells and signal through MyD88 to prevent the production of growth inhibitory IL-22 binding protein (IL-22BP), which enables unrestricted IL-22 to stimulate tissue repair (Huber et al., 2012; Salcedo et al., 2010). Thus, mice defective in key inflammasome-associated molecules such as ASC or caspase-1 are susceptible to carcinogen induced colitis-associated cancer (CAC). Similarly, loss of key adaptor molecules such as MyD88, required for IL1-R signaling are susceptible to AOM/DSS induced CAC. Plausibly, unrepaired lesions enable the infiltration of microbes with heightened genotoxic aptitude that can chronically aggravate inflammatory processes and the production of DNA damaging radical oxygen species (ROS).

While the inflammasome has been shown to be important for processing proinflammatory cytokines such as IL1β and IL-18, it remained to be fully clarified how such wound repair proteins become transcriptionally activated in response to actual genomic damage. However, it has recently been shown that mice lacking the innate immune regulator STING (stimulator of interferon genes) are also sensitive to AOM/DSS-induced CAC (Ahn et al., 2015). STING resides in the endoplasmic reticulum (ER) of hematopoietic cells as well as endothelial and epithelial cells and controls the induction of numerous host defense genes, such as type I IFN as well as pro-inflammatory genes including IL1-β in response to the detection of cyclic dinucleotides (CDNs) such as cyclic-di-AMP (c-di-AMP) generated from intracellular bacteria (Ishikawa and Barber, 2008; Woodward et al., 2010). STING is also the sensor for CDNs produced from a cellular nucleotidyltransferase referred to as cGAS (cyclic GMP-AMP synthase, also referred to as Mab-21 Domain-Containing Protein and C6orf150) (Sun et al., 2013). Cytosolic DNA species which can constitute the genome of invading pathogens such as HSV-1, or plausibly self-DNA leaked from the nucleus can bind to cGAS to generate non-canonical cGAMP containing one 2'-5' phosphodiester linkage and a canonical 3-5' linkage (c[G(2',5')pA(3',5')p]). The STING pathway may recognize damaged DNA during early response to intestinal damage and may be essential for invigorating tissue repair pathways involving IL1β and IL-18 (Ahn et al., 2015). STING has also been recently reported to play an essential role in dendritic cell recognition of dying tumor cells and the priming of anti-tumor cytotoxic T-cell (CTL) responses (Corrales et al., 2015; Woo et al., 2014). Thus, while loss of STING may facilitate tumorigenesis through preventing wound repair and by preventing the production of tumor specific CTLs, the effectiveness of STING signaling in human tumors remains unknown.

SUMMARY

It is reported herein that STING mediated innate immune signaling is largely impaired in human colon cancers as well as many other types of human cancers. In many instances, this was achieved through silencing STING and/or synthase cGAS expression through epigenetic hypermethylation processes. The findings suggest that STING pathway may have a major function in suppressing colon tumorigenesis and that the inhibition of STING function in this pathway may be selectively suppressed during cancer development. Additionally, it is discovered that defects in STING signaling renders cancer cells more susceptible to oncolytic viral infection. Therefore, the examination of STING activity in cancers may lead to development of assays that will shed light into the outcome of select cancer therapies.

It was discovered that the cellular protein STING, which controls innate immune responses to cytoplasmic DNA produced by DNA damaging agents or DNA viruses, is defective in a wide variety of cancer cells. Defects in STING signaling may help tumor cells evade purging by the immune system and constitute a common mechanism of tumorigenesis. Examining STING expression in tumors allows predicting disease outcome and provides a crucial prognostic marker in predicting responses to select anti-tumor therapies. Disclosed herein are experiments showing that mice-deficient in STING (STING knockout or SKO) are prone to colitis associated cancer (CAC) induced by DNA-damaging and inflammatory agents. SKO mice harboring tumors exhibited low levels of tumor suppressive IL22 binding protein (IL22-BP) compared to normal mice, a cytokine important for preventing colon-related tumorigenesis. Analysis of human colon cancer cells and a variety of other cancer cells such as melanoma indicated widespread defects in STING signaling which frequently involved complete loss of STING and/or cyclic GMP-AMP synthase (cGAS), a synthase that generates STING-activating cyclic dinucleotides (CDN's). Such tumor cells were highly susceptible to viral oncolytic therapy.

Disclosed herein are methods for selecting a therapy for treating cancer in a mammalian (e.g., human) subject, and treating a subject with the selected therapy. One such method includes the steps of: isolating a sample from a human subject having cancer; determining the functional activity of STING and/or cGAS in the sample; selecting a therapy for the cancer based on the functional activity of the STING and/or cGAS in the sample, and treating a subject with the selected therapy. Also contemplated is the measurement of levels of IL-22BP's suppression of IL-22, as well as cellular levels of IL-1β, IL-18 and IL-22. A decrease in levels of IL-1β, IL-18, IL-22 and IL-22BP may be indicative of defective STING or cGAS signaling.

In various embodiments, the sample is a body fluid, cell, tissue sample, biopsy, tissue print, skin, hair, a soluble fraction of a cell preparation, or media in which cells were grown. It is contemplated that the body fluid is blood, urine, plasma, saliva, or cerebrospinal fluid.

If the functional activity of STING and/or cGAS is determined to be defective in the sample, the therapy selected is one that is effective at killing STING-deficient and/or cGAS-deficient cancer cells (e.g., therapy including administering to the subject an oncolytic virus such as one having a dsDNA genome, including herpes simplex virus (HSV), Varicella Zoster virus (VZV), or vaccinia virus (VV)). Exemplary virus families that have dsDNA genomes include, but are not limited to, Alloherpesviridae, Herpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae, Poxviridae, Sphaerolipoviridae, Tectiviridae and Turriviridae.

In various embodiments, the examination of STING-signaling is a useful prognostic marker for whether HSV1 or other viral based anti-cancer therapies will be efficacious for the treatment of malignant disease.

In the methods described herein, the subject can be one that has failed at least one chemotherapy regimen (e.g., one that includes administering to the subject an agent which causes DNA mutations) and the step of determining the functional activity of STING in the cell can include analyzing the amount of cGAS in the cell.

In various embodiments, it is contemplated that the selected therapy, e.g., an oncolytic virus, is administered in conjunction with a second therapeutic agent, such as a chemotherapeutic agent. Exemplary chemotherapeutic agents are described below in the Detailed Description.

Also disclosed herein is a method for treating a cancer in a mammalian (e.g., human) subject that includes the steps of: determining the functional activity of STING in a cell making up the cancer; and if the cell does not have defective STING activity, administering a cancer treatment to the subject that does not cause DNA mutation.

Further disclosed herein is a method for treating cancer in a mammalian (e.g., human) subject which includes the steps of: isolating a sample from a human subject having cancer; determining the susceptibility of the cancer to being killed by an oncolytic virus in vitro; and if the cancer is susceptible to being killed in this manner, administering an oncolytic virus to the subject. In various embodiments, the step of determining the functional activity of STING in the sample comprises analyzing the amount of cGAS in the cell. Also contemplated is the measurement of levels of IL-22BP's suppression of IL-22, as well as cellular levels of IL-1β, IL-18 and IL-22. A decrease in levels of IL-1β, IL-18, IL-22 and IL-22BP may be indicative of defective STING or cGAS signaling.

In various embodiments, the cancer is colorectal cancer, colitis-associated cancer or melanoma. Additional exemplary cancers contemplated for treatment herein are set out in the Detailed Description.

In various embodiments, measurement of the presence or absence of STING/cGAS expression is predictive of the response of patients with certain cancers to viral oncolytic therapy. In various embodiments, measurement of response may be carried out using fluorescence in situ hybridization, and analysis of STING and/or cGAS protein or RNA expression, to predict the outcome to oncolytic viral therapy depending on the presence or absence of cGAS or STING.

Provided herein is a method for treating cancer comprising administering a viral oncolytic therapy to a subject, determining the level of STING or cGAS in the subject, wherein a decrease in STING or cGAS activity is predictive of a positive outcome of oncolytic therapy, and i) if levels of STING or cGAS in the subject are low, continuing oncolytic therapy; or ii) if STING or cGAS levels are normal or partially active, discontinuing viral oncolytic therapy and/or administering a second agent that can increase STING levels in the subject in order to improve the outcome of the viral oncolytic therapy.

In various embodiments, the viral oncolytic therapy comprises herpesvirus, VZV or vaccinia virus.

In various embodiments, the determining comprises obtaining a sample from the subject and measuring levels of STING, cGAS, or other biomarkers contemplated herein (e.g., IL-18, IL-22, IL-22BP, IL-1β, IFNβ, type I IFN) in the sample. It is contemplated that the sample is a body fluid, such as blood, urine, plasma, saliva, or cerebrospinal fluid; a cell; a tissue; a tissue print; a fingerprint, skin or hair; and the like; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate.

In various embodiments, an immune response in the cancer that is lacking STING activity or cGAS activity is enhanced by administration of an oncolytic virus. In one embodiment, the immune response includes modulation of T cell activity, modulation of dendritic cell activity, or modulation of immune cytokines.

In various embodiments, the therapy results in increased tumor cell death and/or retarded tumor growth in a subject.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "certain embodiments", "further embodiment", "specific exemplary embodiments", and/ or "another embodiment", each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DESCRIPTION OF THE DRAWINGS

FIGS. 1A-1E show activation of STING-dependent genes by azoxymethane (AOM) (FIG. 1A) Gene array analysis of Wild type (WT) and STING deficient (SKO) mouse embryonic fibroblasts (MEFs) treated with AOM at 0.14 mM for 8 hours (Left) and 1,2-dimethylhydrazine (DMH) at 1 mM for 8 hours (Right). Highest variable genes are shown. Rows represent individual genes; columns represent individual samples. Grayscale indicates transcript levels below, equal to, or above the mean. Scale represents the intensity of gene expression (log 2 scale ranges between −2.4 and 2.4). (FIG. 1B) qPCR analysis of Cxcl10 and Ifit3 in MEFs treated with AOM and DMH same as FIG. 1A. (FIG. 1C) qPCR analysis of Cxcl10 in Human epithelial cell (FHC) treated with AOM and DMH at 1 mM for 24 hours. (FIG. 1D) FHC cells were transfected with STING or control siRNA for 72 hours followed by AOM and DMH treatment same as FIG. 1C, and were then subjected to Cxcl0 mRNA expression (Left). STING expression level after siRNA treatment was determined by qPCR (Right). Data is representative of at least two independent experiments. Error bars indicate s.d. *; p<0.05, Student's t-test. (FIG. 1E) STING Immunohistochemistry staining of the colon tissue from WT and SKO mice (Left) and Human. All images were shown at original magnification, 200×.

FIGS. 2A-2E show loss of STING renders mice susceptible to CAC: (FIG. 2A) Schematic representation of AOM/DSS induced colitis model. WT (n=7) and SKO (n=7) mice were intravenously injected with AOM on Day 1 followed by 7 d administration of dextran sodium sulfate (DSS) in drinking water for four DSS cycles. Normal drinking water was used for control group. (FIG. 2B) Representative photographs of macro-endoscopic colon tumors (Left) and H&E staining (Right) of WT (n=7) and SKO (n=7) mice either AOM/DSS treated or normal water treated. Number of polyps (FIG. 2C) and inflammation score (FIG. 2D, 0: Normal to 3: most severe) from FIG. 2B. (FIG. 2E) Gene array analysis of colon tissue from WT and SKO mice treated same as FIG. 2A. Highest variable gene lists are shown (Right table). Rows represent individual genes; columns represent individual samples. Grayscale indicate transcript levels below, equal to (black), or above the mean. Scale represents the intensity of gene expression (log 2 scale ranges between −2.4 and 2.4).

(FIG. 3A) Fold changes from gene array analysis of Il18 in WT and SKO MEFs administrated with 4 ug/ml of dsDNA90 and IFNβ for 8 hours (Left). qPCR analysis of Il18 in WT and SKO MEFs transfected with 4 µg/ml of dsDNA90 and cyclic-di-GMP-AMP (cGAMP) for 8 hours (Middle). qPCR analysis of Il18 in bone marrow derived dendritic cells (BMDCs) from WT and SKO mice. BMDCs were treated with 1 mM of AOM and 1 mM of DMH for 8 hours (Right). (FIG. 3B) Schematic representation, body weight, and qPCR analysis of IL18, IL22 bp and IL22 from WT and SKO colon during one cycle of DSS administration for 5 days followed by 2 days of normal water. (FIG. 3C) qPCR analysis of IL18, IL22 bp and IL22 in WT and SKO colon tissue from FIG. 2. Data is representative of at least two independent experiments. Error bars indicate s.d. *; p<0.05, Student's t-test.

FIGS. 4A-4G show cytosolic DNA induced innate immune signaling was mostly defective in human colon cancer cells: (FIG. 4A) Immunoblot of STING in a series of human colon cancer cell lines of various type. hTERT and normal human colon epithelial cell line, FHC, were included as positive controls. 20 µg of total protein/per lane was loaded and analyzed by rabbit anti STING polyclonal antibody. β-actin was used as loading control. (FIG. 4B) ELISA analysis of human Interferon β production in the media of cells, same as in (FIG. 4A) following polyI:C or dsDNA90 transfection at 3 µg/ml for 16 hours. Lipofectamine 2000 alone was used as mock transfection. (FIG. 4C) Cells, same as in A, were either mock transfected or transfected with polyI:C or dsDNA90 at 3 µg/ml for 3 hours. Total RNA was extracted and analyzed by qPCR for IFNB expression. (FIG. 4D) RNA, same as in FIG. 4C, was analyzed by qPCR for CXCL10 expression. (FIG. 4G) RNA, same as in FIG. 4C, was analyzed by qPCR for IL1B expression. (FIG. 4E) Gene array analysis of normal or colon cancer cells mock transfected or transfected with 3 µg/ml dsDNA90 for 3 hours. Highest variable genes are shown. Rows represent individual genes; columns represent individual samples. Grayscale legend indicates transcript levels below, equal to, or above the mean. Scale represents the intensity of gene expression (log 10 scale ranges between −3 and 3). (FIG. 4F) List of highest variable genes shown in FIG. 4E as well as their fold induction value following dsDNA90 stimulation. Data is representative of at least two independent experiments. Error bars indicate s.d.

FIGS. 5A-5F show STING activation and cytosolic DNA pathway in colon cancer cells were mostly defective: A series of colon cancer cells as well as normal cell controls were either mock transfected or transfected with dsDNA90 at 3 µg/ml for 3 hours, and were analyzed by Immunofluorescence Microscopy for STING translocation (FIG. 5A), IRF3 translocation (FIG. 5B), and p65 translocation (FIG. 5C). (FIG. 5D) Cells, same as above, were either mock transfected or transfected with dsDNA90 at 3 µg/ml for indicated time periods followed by immunoblot analysis for STING phosphorylation as well as phosphorylation of TBK1, IRF3 and p65. β-actin was used as loading control. (FIG. 5E) Cells, same as above, were analyzed by qPCR for cGAS expression. (FIG. 5F) Cells that have undetectable level of cGAS in E were treated with 1 µM 5-azacytidine for 7 days, followed by qPCR analysis for cGAS expression. Data is representative of at least two independent experiments. Error bars indicate s.d.

(FIG. 6A) A series of colon cancer cells as well as normal cell controls were infected with HSV-luc at M.O.I. 1 or 5 for 24 hours. Cells were then lysed and analyzed for luciferase activity. Data is representative of at least two independent experiments. Error bars indicate s.d. (FIG. 6B) Cells, same as in FIG. 6A, were infected with HSV-luc at M.O.I. 10 for 6 hours. Total RNA was then extracted, followed by qPCR analysis of IFNB production. (FIG. 6C) Same RNA from FIG. 6B was analyzed by qPCR analysis for CXCL10 production. (FIG. 6D) Cells, same as in FIG. 6A, were infected with HSV1γ34.5 deletion mutant at M.O.I. 1 for 6 hours followed by qPCR analysis of IFNB production. Data is representative of at least two independent experiments. Error bars indicate s.d.

FIGS. 7A-7B show gene expression fold changes of Illumina array shown in FIG. 1A.

FIGS. 8A-8C show fluorescence microscopy analysis (related to FIG. 1) of DAPI staining in WT and SKO MEFs treated with 3 mM of AOM of 3 mM of DMH (FIG. 8A) and anti-dsDNA staining and the ration of cytoplasm to nucleus (FIG. 8B) in Human normal colon epithelial cells (FHC) treated with 3 mM of AOM or 3 mM of DMH for 48 hours. (FIG. 8C) Immunofluorescence microscopy analysis of FHC treated with AOM and DMH sane as FIG. 8A for 48 hours using p65 or IRF3 antibody. Images shown at original magnification, 160×.

FIGS. 9A-9B show (FIG. 9A) the number of polyps and (FIG. 9B) shows the inflammation score from FIG. 2A-2E.

FIG. 11. IL18 promoter region contains binding sites for multiple innate immune gene transcription factors. Putative transcription factor binding sites in the IL18 gene promoter is listed and highlighted.

FIG. 12. Shown is a summary of STING signaling pathway in colon cancer cell lines.

(FIG. 13C) cGAS production is deregulated in many colon cancers. cDNA from 5 normal human colon tissues and 43 human colon cancers of various stages were analyzed by qPCR for cGAS expression. (FIG. 13D) Immunoblot (upper) and qPCR analysis (lower) of cGAS expression in normal and human colon cancer cells same as above.

FIG. 14B, Northern blot analysis of STING mRNA expression in cell lines as in FIG. 14A. HUVEC was a positive control. FIG. 14C, ELISA analysis of IFNB production in the media of cells transfected with 3 µg/ml polyI:C or dsDNA90 or mock transfected for 16 hours. PASMC, NHDF-ad and hTERT were included as positive controls.

FIG. 15A, Immunoblot (upper) and qPCR analysis (lower) of cGAS expression in normal and human colon cancer cells same as above. FIG. 15B, qPCR analysis of cGAS expression in cGAS negative colon cell lines mock treated or treated with 1 µM 5-Azacytidine (5AZADC) for 5 days. FIG. 15C, Immunoblot analysis of STING signal activation in cells (selected from FIG. 15B) mock treated or treated with 1 µM 5-Azacytidine (5AZADC) for 5 days, followed by dsDNA90 transfection at 3 µg/ml for indicated time periods. FIG. 15D, Immunofluorescence Microscopy analysis of IRF3 translocation in SW480 and HT116 cells treated with 5AZADC same as above followed by dsDNA transfection at 3 µg/ml dsDNA90 for 3 hours. Original magnification, 1260×. FIG. 15E, IFNB qPCR analysis of cells (same as in FIG. 15C) treated with 5AZADC same as above followed by dsDNA transfection at 3 µg/ml dsDNA90 for 3 hours. Error bars indicate s.d. *, $p<0.05$; , $p<0.01$; *, $p<0.001$; Student's t-test.

FIGS. 16A-16F show STING signal defect leads colon cancer cells more susceptible to DNA virus infection. (FIG. 16A), Cells (same as in FIG. 4A-4F) were infected with HSV1γ34.5 at M.O.I. 5 for 1 hour and human IFNB induction was analyzed by qPCR 3 hours post infection. FIG. 16B, normal human hTERT cells and selected human colon cancer cell lines (cGAS positive: SW1116, HT29; cGAS negative: SW480, HT116) were infected with HSV1γ34.5 at indicated M.O.I. for 1 hour, and titration of HSV1γ34.5 was analyzed by standard plaque assay in Vero cells 24 hours later. FIG. 16C, Cells (same as in FIG. 16B) were infected with HSV1γ34.5 at M.O.I. 1 for 1 hour, and cell viability was analyzed by trypan blue staining 24 hours and 48 hours later. FIG. 16D, Cells (same as in FIG. 16A) were infected with HSV1-Luc at indicated M.O.I. for 1 hour, and luciferase activity was analyzed 24 hours later. FIG. 16E, Colon Cancer cells were infected with Vaccinia Virus at M.O.I. 100 and analyzed by qPCR for IFNB expression 3 hours post infection. FIG. 16F, Cells same as FIG. 16E were analyzed by qPCR for CXCL10 expression. Error bars indicate s.d.

FIGS. 17A-17H show RNA in situ hybridization analysis of STING and cGAS in human colon cancer cell lines and colon cancer tissue microarray. FIG. 17A, RNA fluorescence in situ hybridization (RNA FISH) analysis of STING and cGAS expression in normal and human colon cancer cell lines. Images are shown at 1260×. FIG. 17B, RNA FISH analysis of STING and cGAS expression in SW480 and HT116 mock treated or treated with 1 µM 5 AZADC for 5 days. Images are shown at 1260×. FIG. 17C, Quantitation of STING and cGAS RNA copy number in FIG. 17A. FIG. 17D, Quantitation of cGAS RNA copy number in FIG. 17B. FIG. 17E, STING and cGAS expression in formalin-fixed paraffin-embedded (FFPE) normal and human colon cancer cell lines were analyzed by Chromogenic RNA in situ hybridization (RNA CISH). Quantitation of STING and cGAS RNA copy number are shown in bar graph. Error bars indicate s.d. FIG. 17F, representative images of STING and cGAS RNA CISH analysis are shown at 600×. FIG. 17G, RNA CISH analysis of STING and cGAS expression in a FFPE human colon cancer tissue microarray. A total of 12 normal and 80 cancer tissues were analyzed and number of tissue that are detected with STING and/or cGAS are summarized in the table. FIG. 17H, Representative images of RNA CISH in FIG. 17G are shown at 400×.

FIG. 18A, Scheme of HSV1γ34.5 treatment on xenograft tumor in nude mice. The indicated xenograft tumors (SW116, FIG. 18B; HT29, FIG. 18C; SW480, FIG. 18D; HT116, FIG. 18E) were generated in the right flank of nude Balb/c mice. When tumors had reached approximately 0.5 cm in diameter, tumors were injected every other day a total of three times (arrows) with 1E7 PFU HSV1γ34.5 in 50 µl PBS (N=7) or 50 µl PBS only (N=3) and tumor growth measured every other day. Statistical analysis was carried out comparing the two treatment groups at the last time point using the unpaired Student's t-test. P values are as indicated.

FIG. 20D, cells were similarly treated with siRNA as above followed by HSVγ34.5 infection at MOI 5 for 3 hours. Cells were then analyzed by qPCR for IFNB expression.

FIG. 21B, Bisulfite sequencing analysis of cGAS promoter region. Each box represents one CpG dinucleotide located within the promoter region indicated by the position marker at the bottom. Grayscale compares methylated, unmethylated and not sequenced. FIG. 21C, colon cancer cells were treated with 5AZADC (DNA methyltransferase inhibitor), SAHA (histone deacetylase inhibitor) and BIX01294 (histone-lysine methyltransferase inhibitor) at 1 µM for 5 days. cGAS expression was then examined by qPCR. Error bars indicate s.d.

(FIG. 23A), immunoblot of STING in various transformed or cancer derived human cell lines. HUVEC was used as positive control. FIG. 23B, Northern blot analysis of STING mRNA expression in cell lines. FIG. 23C, ELISA analysis of IFNB production in the media of cells transfected with 3 µg/ml polyI:C or dsDNA90 or mock transfected for 16 hours. PASMC, NHDF-ad and hTERT used as positive control.

FIG. 24 shows sequencing of STING in colon cancer cell lines.

FIG. 25 shows sequencing of cGAS in colon cancer cell lines.

FIG. 26A, hTERT fibroblasts, normal human epidermal melanocytes (HEMa) and a series of human melanoma cell lines were analyzed for STING expression by immunoblot (top) and cGAS expression by qPCR (bottom). FIG. 26B, ELISA analysis of human Interferon β production in the media of cells (same as A) transfected with 3 µg/ml polyIC or dsDNA90 or mock transfected for 16 hours. qPCR analysis of human CXCL10 (FIG. 26C) and IFNB (FIG. 26D) induction in cells (same as FIG. 26A) transfected with 3 µg/ml dsDNA90 or mock transfected for 3 hours.

FIGS. 27A-27D show dsDNA induced STING signaling pathway is defective in majority of human melanoma cell lines. Immunofluorescence Microscopy analysis of STING translocation (FIG. 27A), IRF3 translocation (FIG. 27B) and p65 translocation (FIG. 27C) in normal and human melanoma cell lines transfected with 3 µg/ml dsDNA90 or mock transfected for 3 hours. Original magnification, 1260×. Bar size, 1 µm. FIG. 27D, Immunoblot analysis of STING signal activation in cells (same as above) transfected with 3 µg/ml dsDNA90 for indicated time periods.

FIG. 28A, RNA fluorescence in situ hybridization (RNA FISH) analysis of STING and cGAS expression in normal and human melanoma cell lines. Representative images are shown at 1260×. Bar size, 500 nm. Quantitation of STING and cGAS RNA copy number are shown in bar graph. FIG. 28B, Chromogenic RNA in situ hybridization (RNA CISH) analysis of STING and cGAS expression in formalin-fixed paraffin-embedded (FFPE) normal and human melanoma cell lines. Representative images are shown at 600×. Bar size, 1 µm. Quantitation of STING and cGAS RNA copy number are shown in bar graph. FIG. 28C, Immunohistochemistry analysis of STING and cGAS expression in melanoma cells. Images were shown at 400×. Bar size, 20 µm.

FIG. 30A, qPCR analysis of cGAS expression in indicated human melanoma cells mock treated or treated with 1 µM 5-Azacytidine (5AZADC) for 5 days. FIG. 30B, Immunoblot analysis of STING in indicated human melanoma cells treated same as above. FIG. 30C, RNA FISH analysis of STING and cGAS in cells (same as above) treated with 5AZADC same as above. Representative images are shown at 1260×. Bar size, 400 nm. qPCR analysis of IFNB (FIG. 30D) and CXCL10 (FIG. 30E) in cells (same as above) treated with 5AZADC followed by dsDNA transfection at 3 µg/ml dsDNA90 for 3 hours. Immunofluorescence Microscopy analysis of IRF3 translocation (FIG. 30F) and STING translocation (FIG. 30G) in indicated cells treated same as in FIG. 30D. Representative images are shown at 1260×. Bar size, 500 nm.

FIG. 31C, normal human hTERT cells and selected human melanoma cell lines were infected with HSV1γ34.5 at indicated M.O.I. or M.O.I. 10 for 1 hour, and titration of HSV1γ34.5 was analyzed by standard plaque assay in vero cells 24 hours later. FIG. 31D, Cells (same as in FIG. 31C) were infected with HSV1γ34.5 at M.O.I. 10 for 1 hour, and cell viability was analyzed by trypan blue staining 24 hours and 48 hours later.

FIG. 32A, A375; FIG. 32B, SK-MEL-5; FIG. 32C, RPMI7951; and FIG. 32D, SK-MEL-3 melanoma xenografts were generated in the right flank of nude Balb/c mice. When tumors had reached approximately 0.5 cm in diameter, tumors were injected every other day a total of three times (arrows) with 1E7 PFU HSV1γ34.5 in 50 µl PBS or 50 µl PBS only and tumor growth measured every other day. Statistical analysis was carried out comparing the two treatment groups at the last time point using the unpaired Student's t-test. P values are as indicated.

DETAILED DESCRIPTION

Figure 1A:
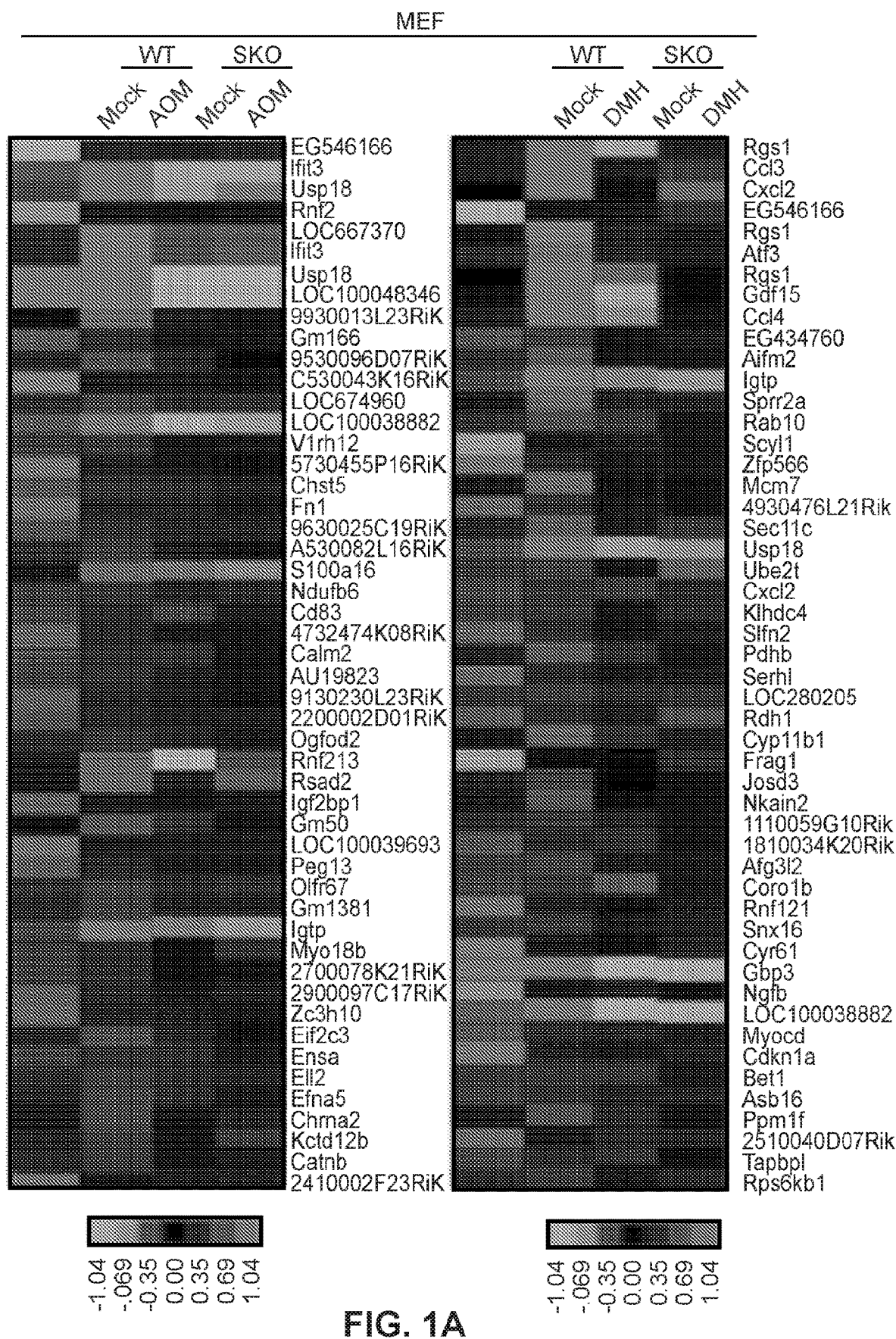

The present disclosure provides methods for selecting a cancer treatment therapy which involves assessing a cell of the cancer for STING activity and treating cancer with an indicated therapy. The below described embodiments illustrate representative examples of these methods. Nonetheless, from the description of these embodiments, other aspects of the invention can be made and/or practiced based on the description provided below.

General Methods

Methods involving conventional immunological and molecular biological techniques are described herein. Immunological methods are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49$^{th}$ Edition, McGraw-Hill Medical, 2010; and Fauci et al., Harrison's Principles of Internal Medicine, 17$^{th}$ Edition, McGraw-Hill Professional, 2008.

An analysis of the function of STING in colon cancer cells was conducted and found that STING was frequently expressed but STING function was ablated in approximately 86% of cells analyzed (n=12). However, the cGAS was not detectable in 30-50% of cells analyzed. In colon cancer cells lacking cGAS, STING function was completely ablated. In cancer colon cells with detectable cGAS, STING function was dramatically reduced. It was also noted that STING and cGAS were gone in a variety of other cancers including melanoma.

The innate immune system provides the first line of defense against pathogen infection though can also influence pathways that can control tumorigenesis. For example, it is known that the cellular adaptor MyD88 (Myeloid differentiation primary response gene 88) that facilitates Toll-like receptor (TLR) and IL-1 receptor (IL-1R) signaling pathway in the innate immune response can regulate tumorigenesis through control of NF-κB activation, cytokine secretion and inflammatory responses. Mice lacking MyD88 are susceptible to colitis-associated carcinogenesis (CAC) induced by the drugs azoxymethane (AOM) and dextran sulfate sodium (DSS). In this situation, MyD88 exerts a protective effect in part by facilitating the production of IL-18, in epithelial cells, which downregulates dendritic cell production of the IL-22 binding protein (IL-22-BP). IL-22-BP suppresses the function of IL-22 which is produced from innate lymphoid cells in response to cellular/tissue damage and which potently stimulates the proliferation of intestinal epithelial cells.

Azoxymethane (AOM) is the metabolite of 1,2-dimethylhydrazine (DMH) and is converted to methylazoxymethanol (MAM) which mediates O-methyl-guanine formation to trigger DNA damage responses. A single injection of AOM into mice, followed by administration of the inflammatory agent dextran sulfate sodium (DSS) via drinking water induces almost 100% colon cancer. It was previously demonstrated that the cellular protein STING (stimulator of cellular genes) facilitates cytosolic DNA-triggered innate immune signaling pathways, independent of Toll-Receptor 9 or the DNA sensor AIM II. In humans, STING is a 348 amino acid endoplasmic reticulum (ER) associated molecule predominantly expressed in epithelial cells as well as cells of the hematopoietic lineage, that has been shown to play a key role in triggering innate immune signaling pathways in response to infection by viruses such as herpes simplex virus 1 (HSV1), and even bacteria. STING has also been shown to be responsible for triggering vascular and pulmonary syndrome, self-DNA-induced inflammatory diseases such as Aicardi Goutieres syndrome (AGS) perhaps forms of severe systemic lupus erythematosus (SLE). STING may be associated with dsDNA-species directly and is highly activated by cyclic dinucleotides (CDN) generated by certain bacteria or by cytosolic dsDNA triggering the activation of a synthase, referred to as cGAS (Cyclic GMP-AMP Synthase, C6orf150, Mab-21 Domain-Containing Protein).

Given that STING appears to play a pivotal role in controlling a variety of inflammation driven events, the methods described herein address the role of STING in inflammation aggravated cancer. Using the AOM/DSS model, observations similar to MyD88, STING-deficient mice (SKO) are sensitive to CAC suggesting a protective role for STING in tumorigenesis. Subsequent analysis indicated that STING signaling and cytokine production was ablated in numerous colon cancer cells analyzed. Data indicates that STING may be a key sensor that promotes the elimination of damaged intestinal epithelial cells. Loss of STING signaling may be a common event in colon-associated cancer, an event that may enable such cells to escape surveillance from the immune system.

Definitions

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "induces or enhances an immune response" is meant causing a statistically measurable induction or increase in an immune response over a control sample to which a therapeutic has not been administered. Preferably the induction or enhancement of the immune response results in a prophylactic or therapeutic response in a subject. Examples of immune responses are increased production of type I IFN, increased resistance to viral and other types of infection by alternate pathogens. The enhancement of immune responses to tumors (anti-tumor responses), or the development of vaccines to prevent tumors or eliminate existing tumors.

The term "STING" is meant to include, without limitation, nucleic acids, polynucleotides, oligonucleotides, sense and antisense polynucleotide strands, complementary sequences, peptides, polypeptides, proteins, homologous and/or orthologous STING molecules, isoforms, precursors, mutants, variants, derivatives, splice variants, alleles, different species, and active fragments thereof. STING polynucleotides and polypeptides are described in U.S. Patent Publications 20130039933 and 20110262485.

The term "lacks a functional STING gene" is meant that a transgenic animal lacks a gene that encodes STING, or lacks other genetic components (e.g. promoters) required for expression of STING.

Unless otherwise indicated, the terms "peptide", "polypeptide" or "protein" are used interchangeably herein, although typically they refer to peptide sequences of varying sizes.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

The term "immunoregulatory" is meant a compound, composition or substance that is immunogenic (i.e. stimulates or increases an immune response) or immunosuppressive (i.e. reduces or suppresses an immune response).

"An antigen presenting cell" (APC) is a cell that is capable of activating T cells, and includes, but is not limited to, monocytes/macrophages, B cells and dendritic cells (DCs). The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

The terms "patient", "subject" or "individual" are used interchangeably herein, and refers to a mammalian subject to be treated, with human patients being preferred. In some cases, the methods of the disclosure find use in experimental animals, in veterinary application, and in the development of animal models for disease, including, but not limited to, rodents including mice, rats, and hamsters; primates, cats and dogs.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "treat", "treated", "treating" and "treatment", as used with respect to methods herein refer to eliminating, reducing, suppressing or ameliorating, either temporarily or permanently, either partially or completely, a clinical symptom, manifestation or progression of an event, disease or condition. Such treating need not be absolute to be useful. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. For example the term "treat" or "treating" with respect to tumor cells refers to stopping the progression of said cells, slowing down growth, inducing regression, or amelioration of symptoms associated with the presence of said cells. Treatment of an individual suffering from an infectious disease organism refers to a decrease and elimination of the disease organism from an individual. For example, a decrease of viral particles as measured by plaque forming units or other automated diagnostic methods such as ELISA etc.

The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Cells of the immune system" or "immune cells", is meant to include any cells of the immune system that may be assayed, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Immune effector cells" refers to cells capable of binding an antigen and which mediate an immune response selective for the antigen. These cells include, but are not limited to, T cells (T lymphocytes), B cells (B lymphocytes), monocytes, macrophages, natural killer (NK) cells and cytotoxic T lymphocytes (CTLs), for example CTL lines, CTL clones, and CTLs from tumor, inflammatory, or other infiltrates.

"Immune related molecules" refers to any molecule identified in any immune cell, whether in a resting ("non-stimulated") or activated state, and includes any receptor, ligand, cell surface molecules, nucleic acid molecules, polypeptides, variants and fragments thereof.

"T cells" or "T lymphocytes" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, activation of other immune cells, such as B-cells) or for the cytokines they produce.

The phrase "T cell response" means an immunological response involving T cells. The T cells that are "activated" divide to produce antigen specific memory T cells or antigen specific cytotoxic T cells. The cytotoxic T cells bind to and destroy cells recognized as containing the antigen. The memory T cells are activated by the antigen and thus provide a response to an antigen already encountered. This overall response to the antigen is the antigen specific T cell response, e.g. tumor specific.

A "secondary immune response" or "adaptive immune response" may be active or passive, and may be humoral (antibody based) or cellular that is established during the life of an animal, is specific for an inducing antigen, and is marked by an enhanced immune response on repeated encounters with said antigen. A key feature of the T lymphocytes of the adaptive immune system is their ability to detect minute concentrations of pathogen-derived peptides presented by MHC molecules on the cell surface.

As used herein, "pharmaceutical composition" refers to a composition suitable for administration to a subject animal, including humans and mammals. A pharmaceutical composition comprises a pharmacologically effective amount of a virus or antigenic composition of the invention and also comprises a pharmaceutically acceptable carrier. A pharmaceutical composition encompasses a composition comprising the active ingredient(s), and the inert ingredient(s) that make up the pharmaceutically acceptable carrier, as well as any product which results, directly or indirectly, from combination, complexation or aggregation of any two or more of the ingredients. Accordingly, the pharmaceutical compositions of the present invention encompass any composition made by admixing a compound or conjugate of the present invention and a pharmaceutically acceptable carrier.

As used herein, "pharmaceutically acceptable carrier" include any and all clinically useful solvents, dispersion media, coatings, antibacterial and antifungal agents, isotonic and absorption delaying agents, buffers, and excipients, such as a phosphate buffered saline solution, 5% aqueous solution of dextrose or mannitol, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Pharmaceutical carriers useful for the composition depend upon the intended mode of administration of the active agent. Typical modes of administration include, but are not limited to, enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound or conjugate for pharmaceutical use including, e.g., metal salts (sodium, potassium, magnesium, calcium, etc.) and salts of ammonia or organic amines.

As used herein, "pharmaceutically acceptable" or "pharmacologically acceptable" refers to a material which is not biologically or otherwise undesirable, i.e., the material may be administered to an individual without causing any undesirable biological effects or interacting in a deleterious manner with any of the components of the composition in which it is contained, or when administered using routes well-known in the art, as described below.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavidin, digoxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample.

Labels

In some embodiments, the STING, cGAS or other molecule is labeled to facilitate its detection. A "label" or a "detectable moiety" is a composition detectable by spectroscopic, photochemical, biochemical, immunochemical, chemical, or other physical means. For example, labels suitable for use in the present invention include, but are not limited to, radioactive labels (e.g., $^{32}$P), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide.

Examples of labels suitable for use in the present invention include, but are not limited to, fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

The label may be coupled directly or indirectly to the desired component according to methods well known in the art. Preferably, the label in one embodiment is covalently bound to the molecule using an isocyanate reagent for conjugation of an active agent according to the invention. In one aspect of the invention, the bifunctional isocyanate reagents of the invention can be used to conjugate a label to a target molecule to form a label target molecule conjugate without an active agent attached thereto. The label target molecule conjugate may be used as an intermediate for the synthesis of a labeled conjugate according to the invention or may be used to detect the target molecule conjugate. As indicated above, a wide variety of labels can be used, with the choice of label depending on sensitivity required, ease of conjugation with the desired component, stability requirements, available instrumentation, and disposal provisions. Non-radioactive labels are often attached by indirect means. Generally, a ligand molecule (e.g., biotin) is covalently bound to the target molecule. The ligand then binds to another molecule (e.g., streptavidin), which is either inherently detectable or covalently bound to a signal system, such as a detectable enzyme, a fluorescent compound, or a chemiluminescent compound.

The STING, cGAS or other molecule contemplated herein for use in the methods can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means for detecting labels are well known to those of skill in the art. Thus, for example, where the label is radioactive, means for detection include a scintillation counter or photographic film, as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

Formulation of Pharmaceutical Compositions

To administer compositions of the present disclosure to human or test animals, it is preferable to formulate the active agent in a composition comprising one or more pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

In addition, compounds may form solvates with water or common organic solvents. Such solvates are contemplated as well.

The compositions are administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration, e.g. through a catheter placed close to the desired site.

Pharmaceutical compositions of the present disclosure containing the active agent described herein may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present disclosure.

Formulation of the pharmaceutical composition will vary according to the route of administration selected (e.g., solution, emulsion). An appropriate composition comprising the composition to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers.

A variety of aqueous carriers, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations are prepared for storage by mixing the active agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methyl-methacylate) microcapsule, respectively, in colloidal drug delivery systems (for example, liposomes, albumin microspheres, microemulsions, nano-particles and nanocapsules)

or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxy-benzoate.

The active agents described herein can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of active agent in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of active agent. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of active agent is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (J. Pharm. Sci., 85:1282-1285 (1996)) and Oliyai and Stella (Ann. Rev. Pharmacol. Toxicol., 32:521-544 (1993)).

In addition, the properties of hydrophilicity and hydrophobicity of the compositions contemplated for use in the present disclosure are well balanced, thereby enhancing their utility for both in vitro and especially in vivo uses, while other compositions lacking such balance are of substantially less utility. Specifically, compositions contemplated for use in the disclosure have an appropriate degree of solubility in aqueous media which permits absorption and bioavailability in the body, while also having a degree of solubility in lipids which permits the compounds to traverse the cell membrane to a putative site of action. Thus, antibody compositions contemplated are maximally effective when they can be delivered to the site of target antigen activity.

Administration and Dosing

In one aspect, methods of the present disclosure include a step of administering a pharmaceutical composition. In certain embodiments, the pharmaceutical composition is a sterile composition.

Methods of the present disclosure are performed using any medically-accepted means for introducing therapeutics directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of the cancer.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, every other day, twice weekly, three times weekly, weekly, every 2 weeks, every 3 weeks, monthly, or at a longer interval.

Also contemplated in the present disclosure is the administration of multiple agents, such as the active agent compositions in conjunction with a second agent as described herein, including but not limited to a chemotherapeutic agent. Suitable chemotherapeutic agents include: daunomycin, doxorubicin, methotrexate, and vindesine (Rowland et al., (1986) supra) and those listed in the Table below.

Alkylating agents
Nitrogen mustards mechlorethamine
cyclophosphamide
ifosfamide
melphalan
chlorambucil
Nitrosoureas carmustine (BCNU)
lomustine (CCNU)
semustine (methyl-CCNU)
Ethylenimine/Methyl-melamine thriethylenemelamine (TEM)
triethylene thiophosphoramide (thiotepa)
hexamethylmelamine (HMM, altretamine)
Alkyl sulfonates busulfan
Triazines dacarbazine (DTIC)
Antimetabolites
Folic Acid analogs methotrexate
Trimetrexate
Pemetrexed (Multi-targeted antifolate)
Pyrimidine analogs 5-fluorouracil
fluorodeoxyuridine
gemcitabine
cytosine arabinoside (AraC, cytarabine)
5-azacytidine
2,2'-difluorodeoxy-cytidine
Purine analogs 6-mercaptopurine
6-thioguanine
azathioprine
2'-deoxycoformycin (pentostatin)

-continued erythrohydroxynonyl-adenine (EHNA)
fludarabine phosphate
2-chlorodeoxyadenosine (cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Nonsteroidal antiandrogens flutamide
Natural products
Antimitotic drugs
Taxanes paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubido-mycin)
doxorubicin (adria-mycin)
mitoxantroneidarubicin
bleomycin
splicamycin (mithramycin)
mitomycinC
dactinomycin
aphidicolin
Enzymes L-asparaginase
L-arginase -continued

| Radiosensitizers |
| --- |
| metronidazole |
| misonidazole |
| desmethylmisonidazole |
| pimonidazole |
| etanidazole |
| nimorazole |
| RSU 1069 |
| EO9 |
| RB 6145 |
| SR4233 |
| nicotinamide |
| 5-bromodeozyuridine |
| 5-iododeoxyuridine |
| bromodeoxycytidine |
| Miscellaneous agents |
| Platinium coordination complexes |
| cisplatin |
| Carboplatin |
| oxaliplatin |
| Anthracenedione |
| mitoxantrone |
| Substituted urea |
| hydroxyurea |
| Methylhydrazine derivatives |
| N-methylhydrazine (MIH) |
| procarbazine |
| Adrenocortical suppressant |
| mitotane (o,p'-DDD) |
| ainoglutethimide |
| Cytokines |
| interferon (α, β, γ) |
| interleukin-2 |
| Photosensitizers |
| hematoporphyrin derivatives |
| Photofrin ® |
| benzoporphyrin derivatives |
| Npe6 |
| tin etioporphyrin (SnET2) |
| pheoboride-a |
| bacteriochlorophyll-a |
| naphthalocyanines |
| phthalocyanines |
| zinc phthalocyanines |
| Radiation |
| X-ray |
| ultraviolet light |
| gamma radiation |
| visible light |
| infrared radiation |
| microwave radiation |

The amounts of active agent composition in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveals optimal dosages for particular disease states and patient populations.

Also contemplated in the present disclosure, the amounts of active agent in a given dosage may vary according to the size of the individual to whom the therapy is being administered as well as the characteristics of the disorder being treated. It will also be apparent that dosing may be modified if traditional therapeutics are administered in combination with therapeutics of the disclosure.

Exemplary conditions or disorders that can be treated using the present methods include cancers, such as esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22; q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, and myelodysplastic syndrome.

Example 1

Activation of STING-Dependent Genes by AOM.

Figure 1B:
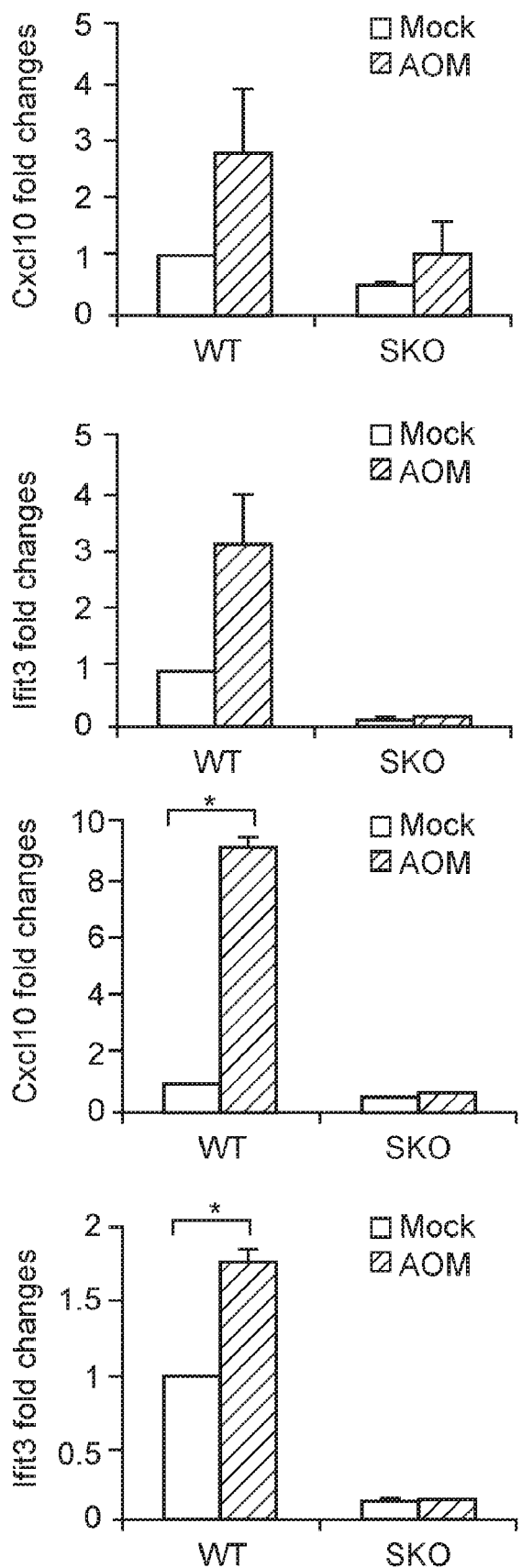

Given that chronic inflammation is known to aggravate colon cancer and that STING has been shown to influence inflammatory responses, especially that invoked by cytosolic self or pathogen related DNA, the role of STING in the control of inflammatory colitis-associated carcinogenesis (CAC) was examined. Towards these objectives, the AOM/DSS model, as described above, was utilized and analyzed the effects of AOM and precursor DMH upon STING signaling. Principally, wild type (WT) or STING-deficient (SKO) murine embryonic fibroblasts (MEF) were treated in vitro with DMH or metabolite AOM for 8 hours and microarray analysis performed to analyze the consequences to gene expression. This study indicated that AOM activated mRNA production of a wide array of innate immune related genes in WT cells, including IFIT3 and Cxcl2 (FIG. 1A; FIG. 7). However, there was a marked decrease in the production of the same genes in cells lacking STING (SKO) indicating that AOM was indeed capable of activating the STING pathway (FIG. 1A, left panel). A similar effect was observed following the treatment of cells with DMH (FIG. 1A, right panel). The observed STING-dependent gene expression was confirmed following RT-PCR analysis of select mRNA such as Cxcl10 and IFIT3 (FIG. 1B). Similarly normal human colon epithelial cells (FHC) were treated with AOM and a similar induction of innate immune genes was observed, controlled by STING, including Cxcl10 (FIG. 1C). The production of Cxcl10 by AOM was similarly reduced in FHC's treated with RNAi to STING (FIG. 1D). Thus, the DNA damaging agent DMH/AOM can invoke STING-dependent signaling.

Figure 8C:
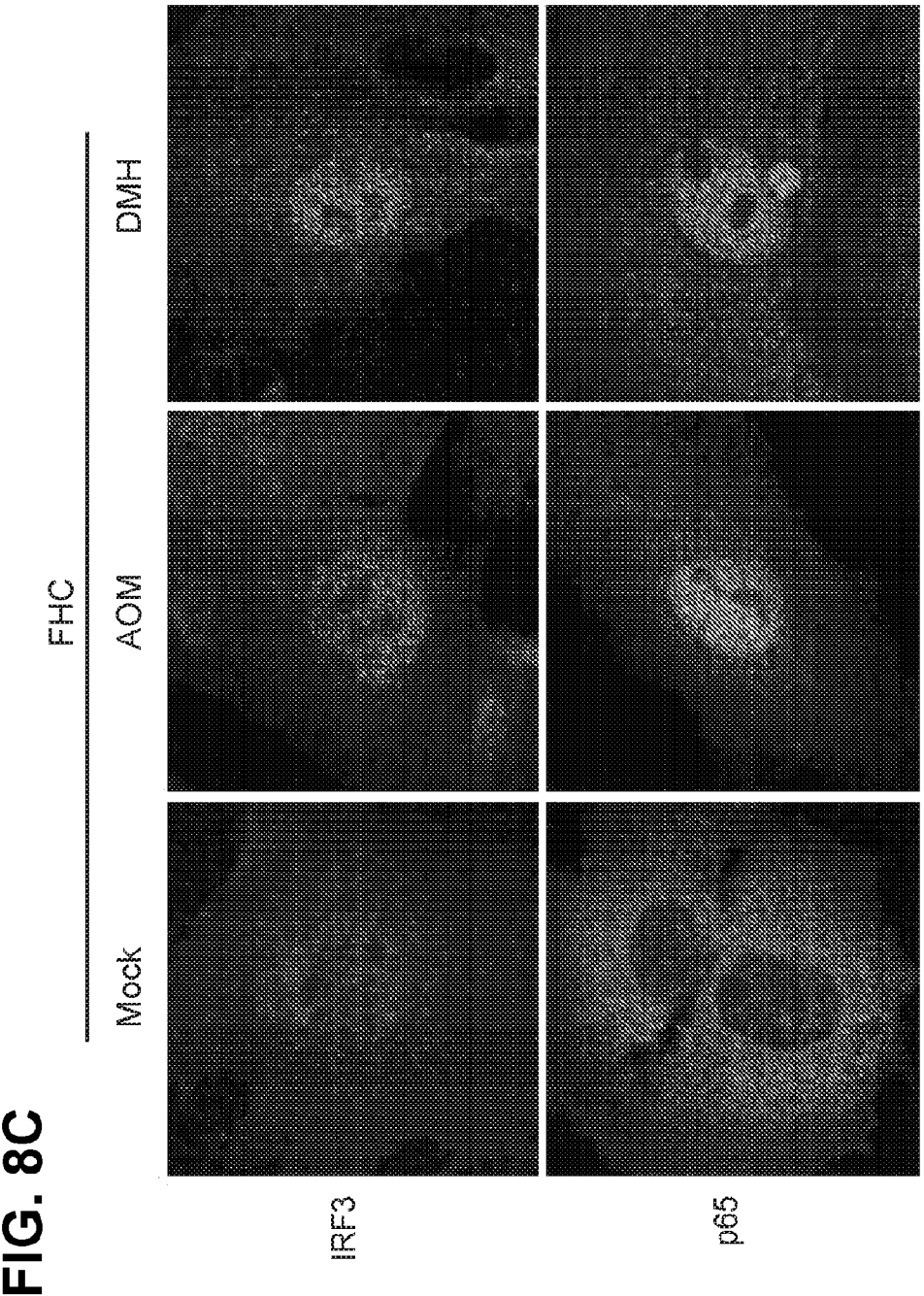
Figure 10A:
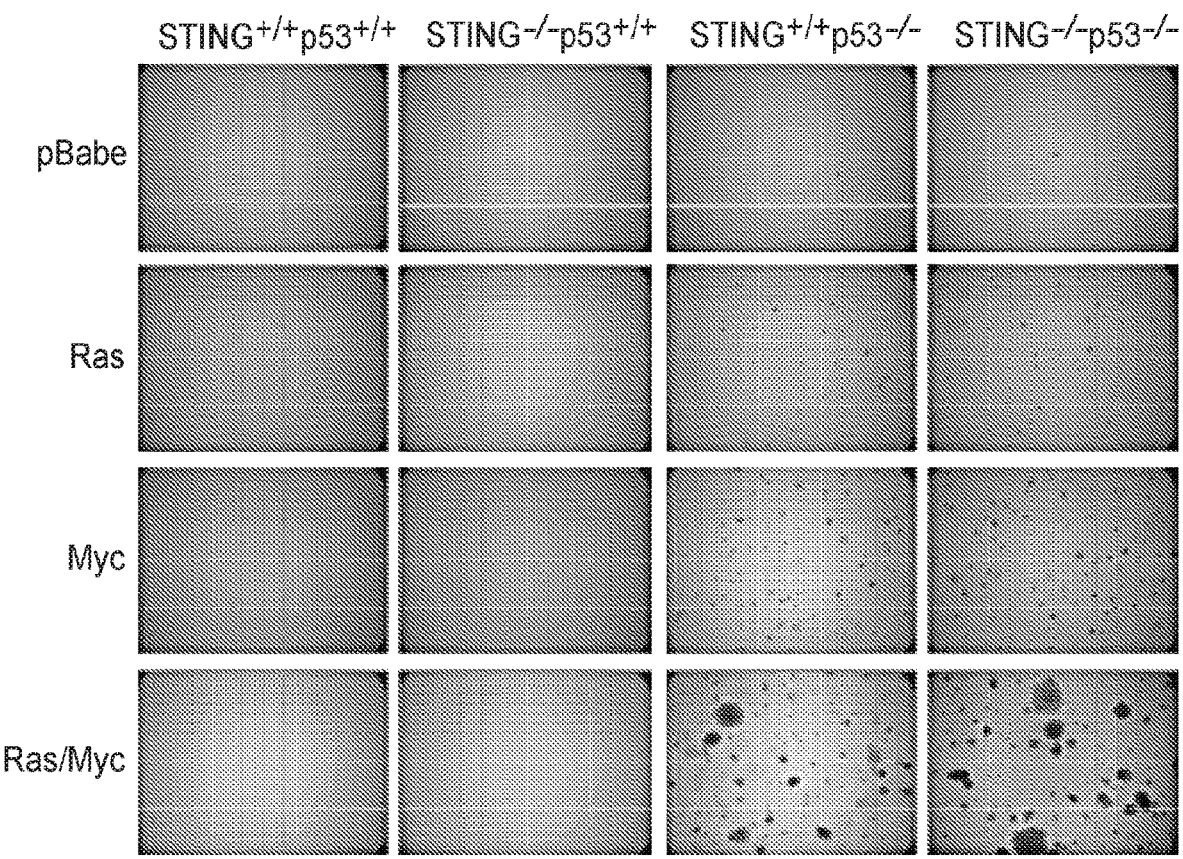
FIGS. 10A-10B show primary MEF cells lacking STING and/or p53 were transduce with retrovirus encoding human H-Ras 12V or human c-Myc. After drug selection with puromycin and hygromycin, the cells were cultured in soft agar. After 14 days, colonies were photographed (FIG. 10A) and colony numbers in one well (n=3) were counted (FIG. 10B). Error bars indicated standard deviation.
Figure 10B:
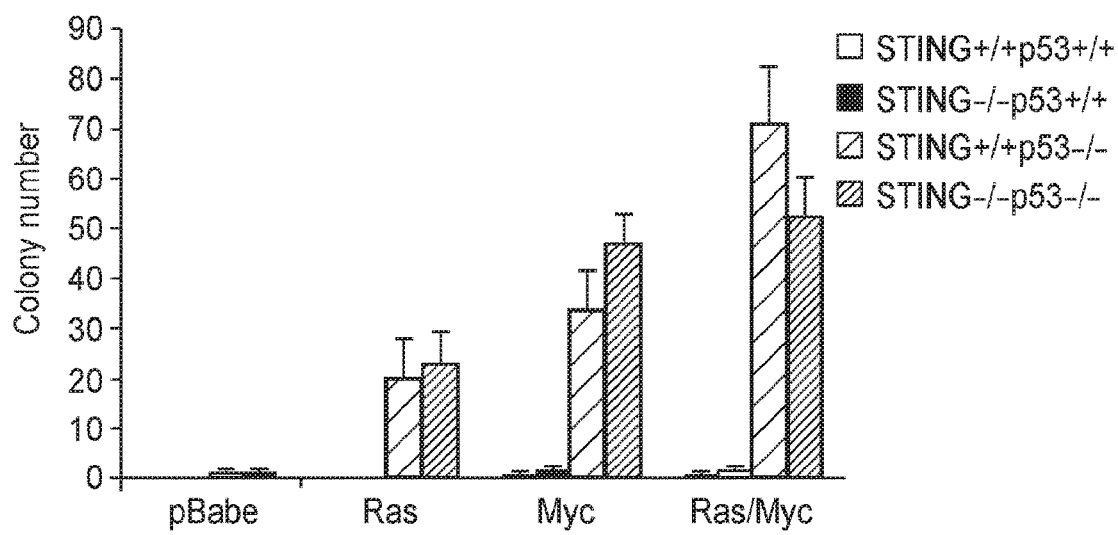

To start determining the mechanisms underlining the cause of DMH/AOM-induced STING activity, MEF or FHC cells were treated with these drugs and observed by two different approaches, DAPI staining and immunofluorescence (IF) using anti-dsDNA antibody, the leakage of DNA into the cytosol (FIGS. 8A and 8B). Cytosolic DNA activates STING and stimulates STING/TBK1 trafficking via autophagy to endosomal regions harboring the transcription factors IRF3 and NF-κB, which triggers cytokine production. Thus, to determine the consequences of DMH/AOM treatment upon STING's ability to activate these key transcription factors, IF analysis on FHC'S treated with these drugs was carried out. This study indicated that DMH/AOM could instigate the translocation of IRF3/NF-κB in treated cells (FIG. 8C). Thus, DMH/AOM induces STING-dependent signaling conceivably through the leaking of DNA into the cytosol (FIG. 1A; FIGS. 8A and 8B).

Figures 1, 2E:
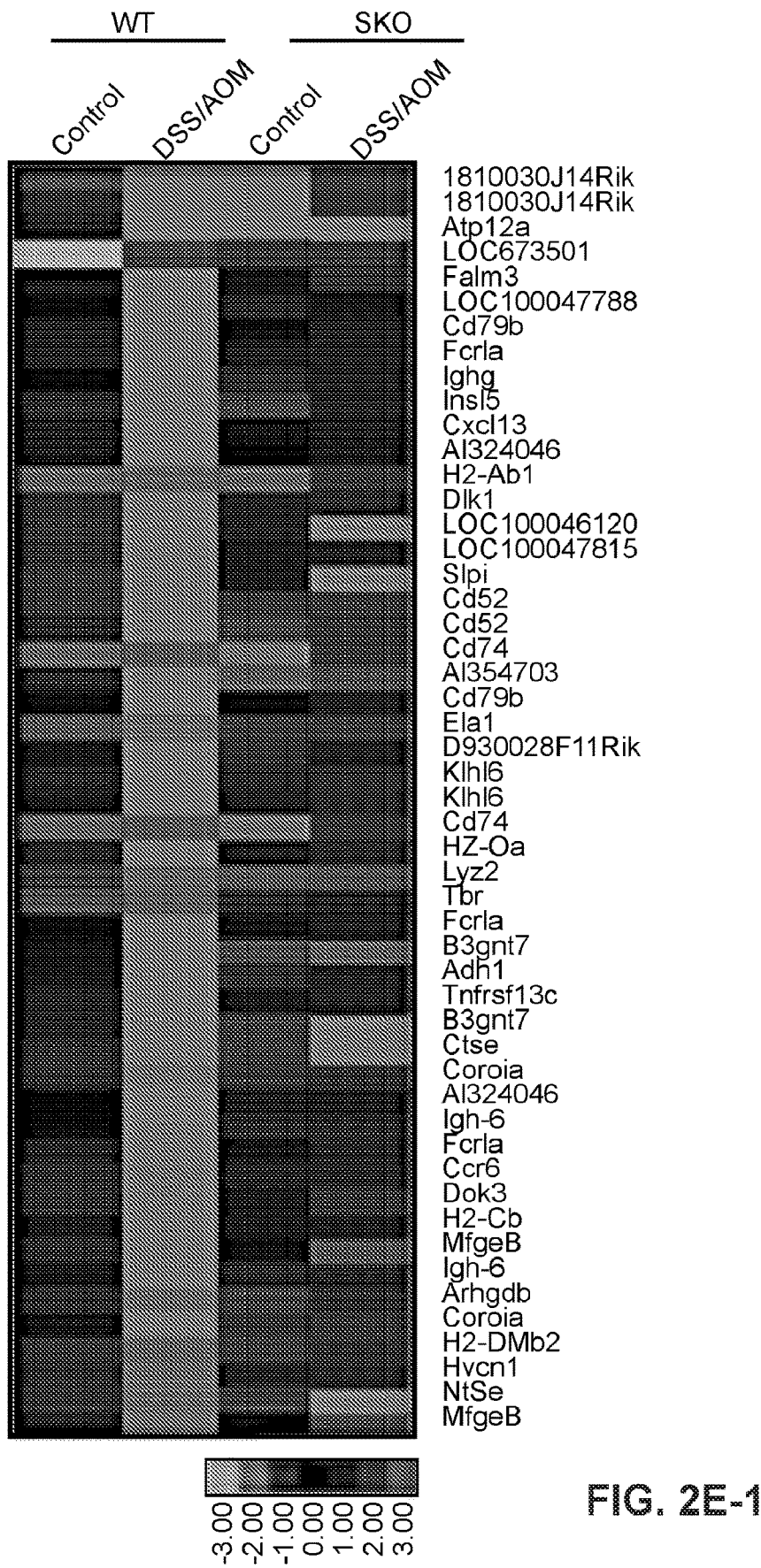

Loss of STING Renders Mice Susceptible to CAC:

The data indicates that DMH/AOM can activate STING in vitro. To examine the consequences of this in vivo, mice were treated once with AOM and subsequently orally with 4 treatments of DSS. Prior to this, STING expression in the intestine was analyzed by IHC. This study showed that STING was expressed in lamina propria cells as well as in endothelial and epithelial cells of the gastrointestinal tract (FIG. 1E). After 13 weeks the mice were analyzed for tumor development in the colon. Surprisingly, the mice lacking STING (SKO) developed colonic tumors at a much higher frequency compared to wild type mice (WT) (FIG. 2A-C; FIG. 9A). Indeed, 4/7 WT mice exhibited tumor formation compared to 7/7 SKO within the same time period (FIGS. 2A and 2B; FIG. 9A), Hematoxylin and eosin (HE) analysis confirmed that AOM/DSS treated SKO mice exhibited significant inflammatory cell infiltration and development of adenocarcinoma in colon, compared to WT mice (FIG. 2B; FIG. 9B). However, microarray analysis indicated that tumors from WT mice exhibited higher levels of select gene expression, such as Cxcl13 and Ccr6, compared to tumors retrieved from SKO mice, perhaps since loss of STING suppressed immunomodulatory transcriptional events (FIG. 2E). It is postulated that STING may recognize damaged DNA and activate the production of cytokines that conceivably could promote tissue repair or stimulate the immune system to eradicate such cells. Thus, loss of STING may enable damaged cells to escape immune surveillance processes and progress more readily into tumors.

Chronic STING Activation is Responsible for Inflammatory Bowel Disease.

Transient STING activation in response to cell damaging agents such as AOM and dextran sulphate (DSS) facilitates wound healing. Thus, loss of STING may lead to a lack of colonic repair and the infiltration of genotoxic microbiota that aggravate STING-independent inflammatory responses. However, chronic irritation of STING in wild type mice by agents such as DSS can lead to inflammatory bowel disease (IBD). Thus, suppression of STING activity by inhibitors/drugs/compounds may lead to a reduction in IBD such as Crohn's disease and ulcerative colitis.

Suppression of IL22BP Expression in STING-Deficient Mice.

In demonstrating that loss of STING facilitated colon cancer development, the tumor suppressive mechanisms associated with STING activity remain to be clarified. It remains plausible that STING could exert direct tumor suppressive, growth inhibitory or pro-apoptotic properties similar to tumor suppressor p53. Further, AOM treatment has been known to induce frequent Ras mutations, which in the context of loss of STING, could facilitate cellular transformation. Expression of oncogenic Ras in an environment where p53 function is lost renders normal cells the ability to form foci in soft agar and to become tumorigenic. To evaluate this possibility, WT, SKO, or p53-deficient MEFs were transfected as positive controls, with Myc or activated Ras and cellular transformation monitored. MEF's lacking p53 were found to be readily transformed by the introduction of Myc or activated Ras. However, MEF's lacking STING did not appear appreciably sensitive to transformation by overexpression of Myc, or activated Ras. Thus, the absence of STING does not appear to exert an oncogenic stimulus, at least in vitro or to cooperate with Myc or Ras in the cellular transformation process.

Figure 3A:
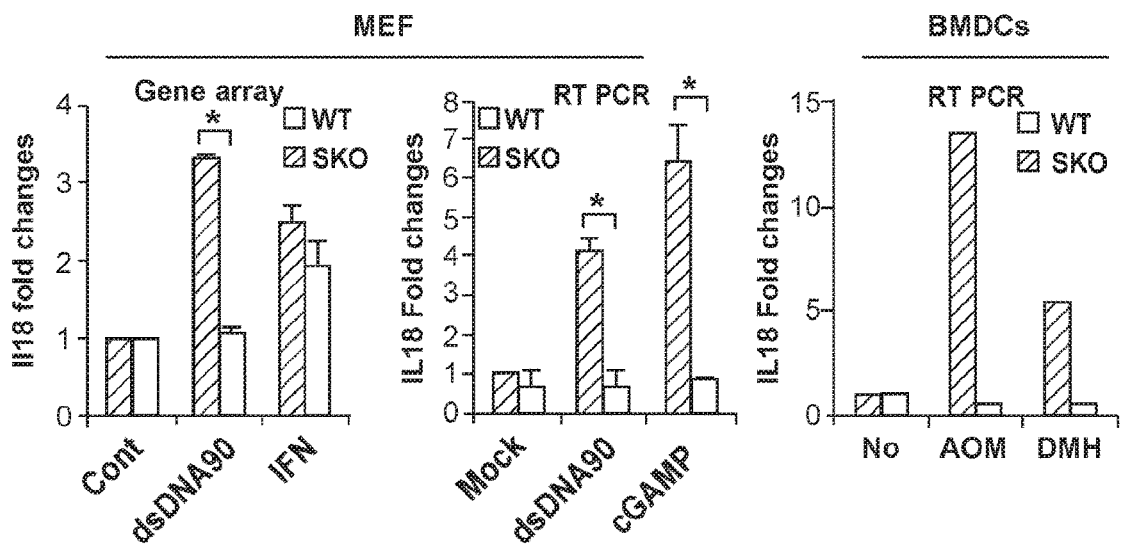
FIGS. 3A-3C show suppression of IL22BP expression in STING-deficient mice.

However, it has been demonstrated that mice lacking certain cytokines such as IL-18, IL-22 or the innate immune adaptor MyD88 are similarly susceptible to AOM/DSS induced CAC. In this situation, MyD88 exerts a protective effect by facilitating the production of IL-18 through the IL-18R, which is required to inhibit IL-22BP. IL-22BP is necessary to suppress IL-22 function, which can promote the proliferation of intestinal epithelial cells following damage by carcinogens or inflammatory agents. Mice lacking IL-18 or IL-22BP are highly susceptible to CAC, similar to STING-deficient mice. It was noted from the microarray analyses that IL-18 levels were reduced in SKO MEFs treated with STING-activating dsDNA (dsDNA90 base pairs) (FIG. 3A). Therefore investigation of the involvement of STING on the possible regulation of the IL-18/IL-22BP axis was made. First, a confirmation of the influence of STING upon IL-18 expression was made since it was additionally noted that the promoter of this cytokine is known to harbor numerous sites recognized by innate immune gene activating transcription factors such as STAT1, NF-κB, IRF1 and IRF7. The analysis indicated that IL-18, which is expressed in a wide variety of cell types, is a STING inducible gene, as determined following treatment of MEF cells with dsDNA or STING-activating CDN's (cGAMP) (FIG. 3A). A similar study indicated that DMH/AOM could also trigger the production of IL-18 in dendritic cells, in a STING-dependent manner, confirming that IL-18 can indeed be induced through the STING pathway.

Figure 3B:
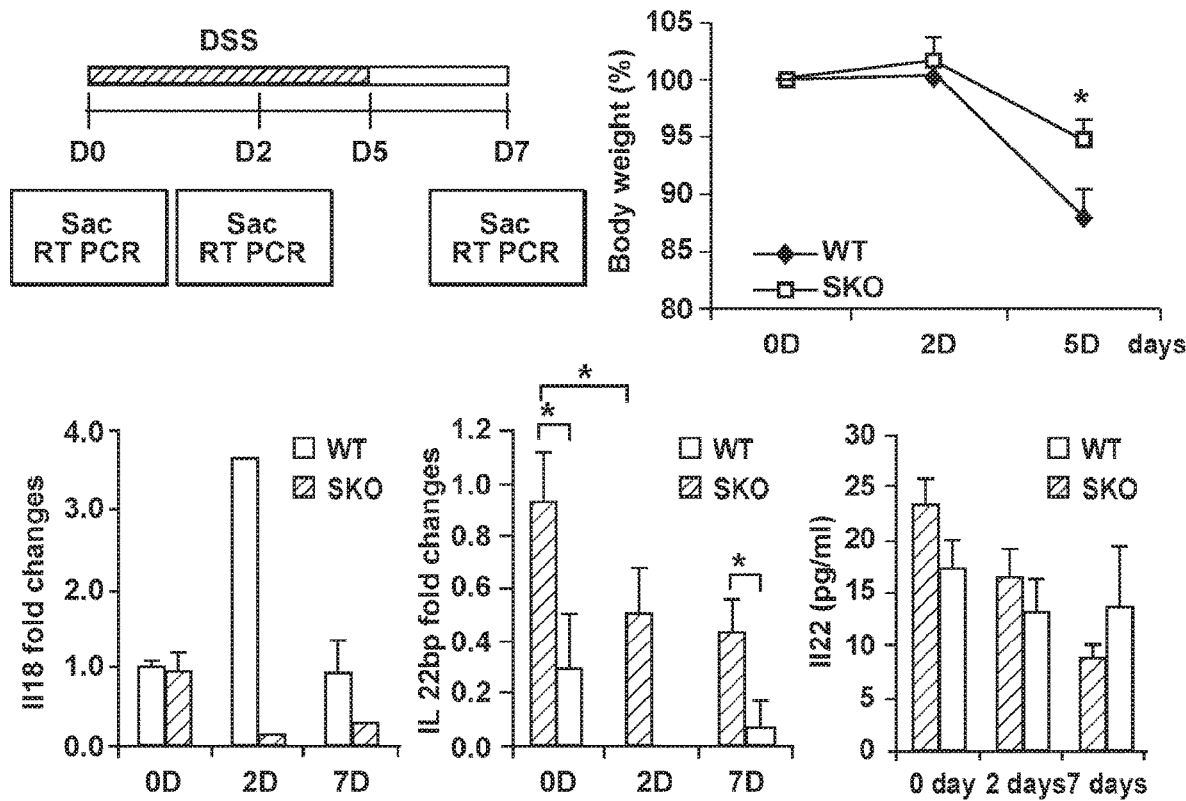
Figure 3C:
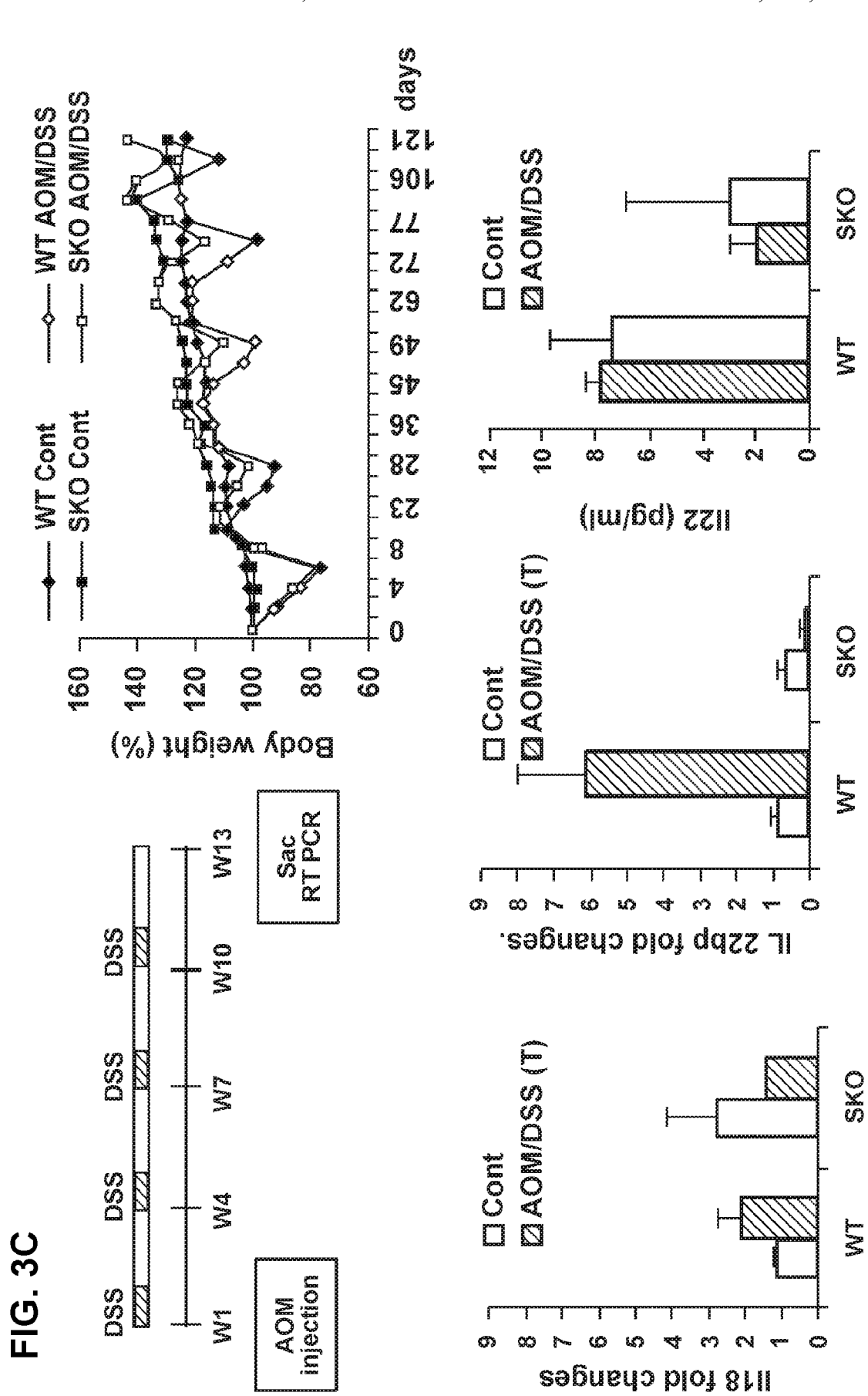

Following the confirmation, an examination of whether DSS treatment could affect IL-18 and IL-22BP expression in vivo was made. Following 7 days of DSS treatment, colons were retrieved from WT or SKO mice and IL-18, IL-22BP or IL-22 expression analyzed by RT-PCR. This study indicated that IL-18 expression was reduced in mice lacking STING (SKO) after 2 days treatment (FIG. 3B). However, a much more pronounced decrease in IL-22BP expression, a protein predominantly expressed from CD11c+ dendritic cells, was observed in SKO mice compared to WT mice (FIG. 3B). The expression of IL-22, in contrast, remained relatively unaffected. It was surprising to note that IL-22BP levels were suppressed in the absence of STING, where IL-18 levels were noted to be also relatively low. However, it has been reported that downregulation of IL22-BP can occur even in the absence of IL-18, indicating that other STING-dependent factors may also contribute to the regulation of IL-22BP. To complement this study, control or SKO mice with AOM/DSS regimes were treated and after 13 weeks again analyzed IL-22BP expression levels in normal or tumor tissue taken from the treated mice. Analogous to DSS treatment alone, observations noted the greatly reduced expression of IL-22BP in the tumors of SKO mice compared to WT mice (FIG. 3C). However, IL-18 and IL-22 levels appeared less dramatically affected. Taken together, it is conceivable that DNA damage or the sensing of microbial ligands that may invade colon tissue after intestinal damage (for example by DSS) can trigger STING activity leading to the production of IL-18. This event would suppress IL-22BP production and enable IL-22 to facilitate tissue repair. However, it appears that loss of STING function in the long term also influences IL-22BP production which is critical for controlling the growth stimulator properties of IL-22. This event may be mediated by microbes triggering STING-dependent innate immune pathways that control IL-22BP production. Data thus indicates that similar to mice lacking MyD88, IL-18 or IL-22BP, STING-deficient mice are also prone to CAC induced by AOM/DSS.

STING Activity is Suppressed in Colonic Tumor Cells.

Figure 4A:
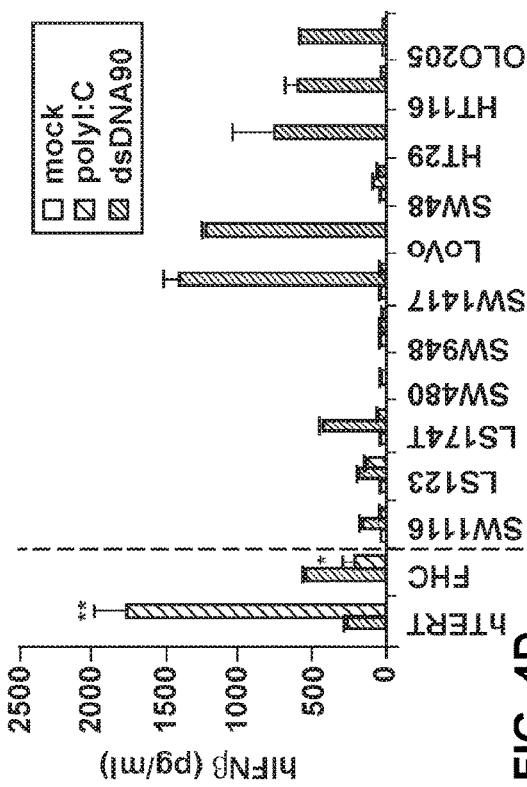
Figure 4B:
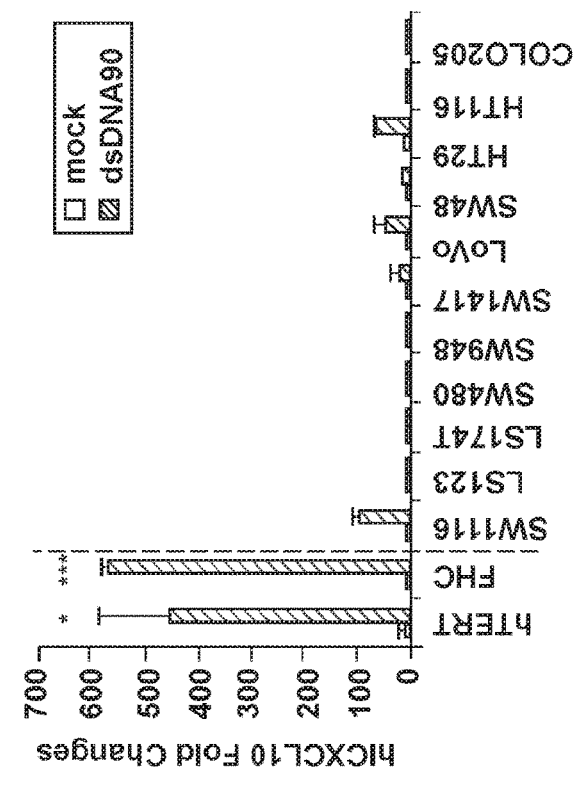
Figure 4C:
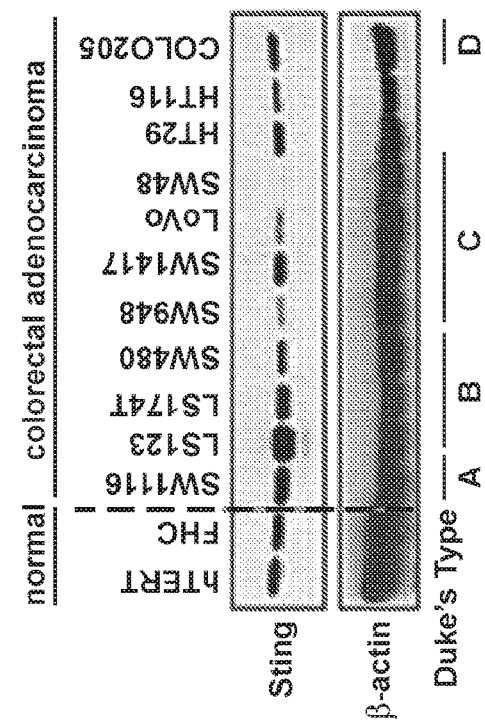
Figure 4D:
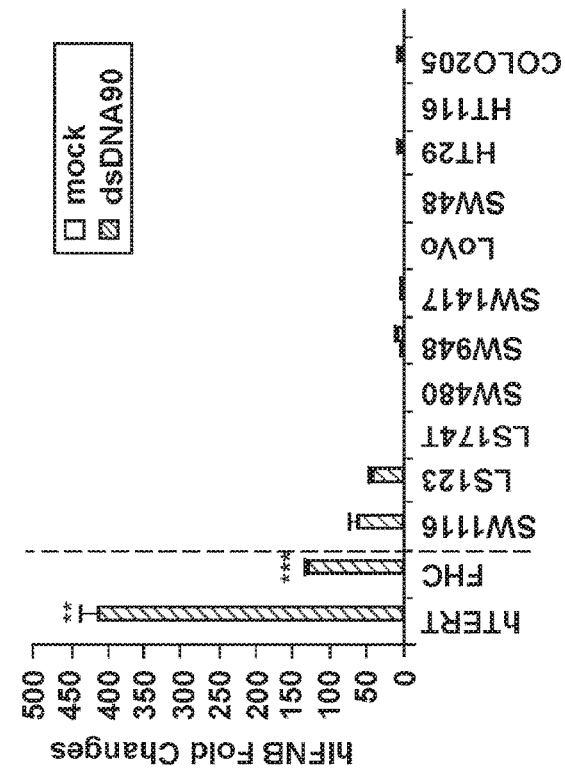
Figure 4E:
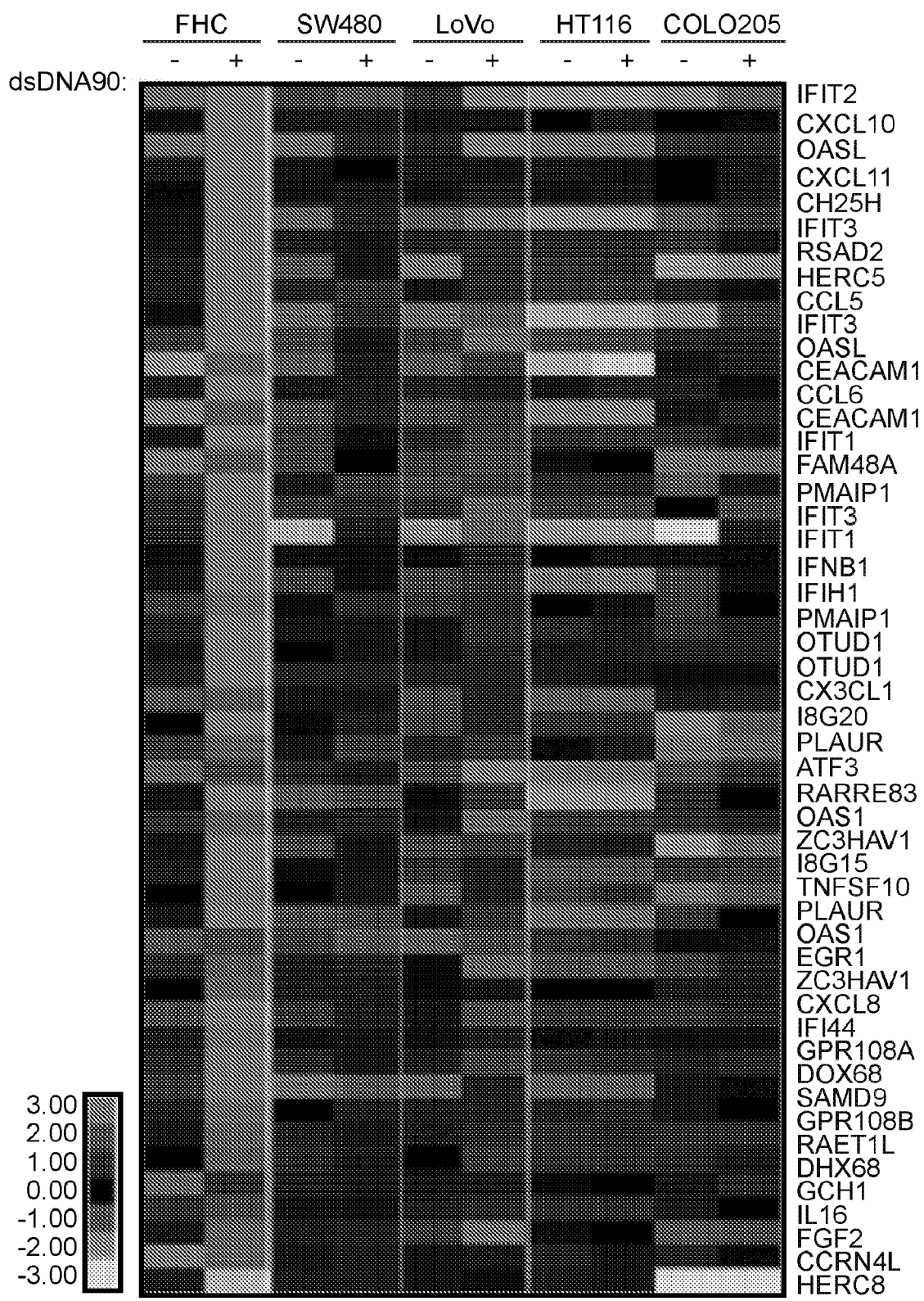

Data indicates that STING is required to protect against carcinogens and perhaps microbes that facilitate inflammation driven CAC. STING conceivably senses DNA damage and signals the event to anti-tumor immunosurveillance cells. Dendritic cells (DC) such as CD8 alpha DCs engulf tumor cells or necrotic tumor cell debris, and the DNA from the engulfed cell or debris activates STING extrinsically in the DC. This leads to the production of cytokines that are essential for anti-tumor T cell responses. Given this, STING signaling in human colonic cells was analyzed, since it was feasible that defects in STING function may enable damaged cells to evade the immune system. To thus evaluate STING signaling in human colonic cancer cells, STING expression in hTERT and (FHC) intestinal epithelial cells as controls were examined. STING was found to be expressed in these cells and to produce type I IFN in response to transfected cytosolic DNA (dsDNA 90 base pairs), which is known to be a STING-dependent event (FIG. 4A-C). A similar inducible effect by dsDNA was noted following measurement by Cxcl10, also a highly dsDNA-inducible, STING regulated gene (FIG. 4D). Next, examination of the expression of STING in a variety of tumor cells isolated from various stages of colon cancer was done and it was found that 10/11 cell lines expressed STING (FIG. 4A; FIG. 12). However, the STING pathway was defective in the majority of cells analyzed (>80%) and such cells could not efficiently produce type I IFN in response to cytosolic dsDNA (FIG. 4A-C). Only two out the 11 cell lines analyzed (SW116 and LS123) appeared only somewhat able to produce type I IFN in response to cytosolic DNA stimulation. In contrast, transfected synthetic dsRNA (polyI:C) was able to stimulate the production of type I IFN relatively well in all but 3 of the cancer cells, likely indicating that the RIGI/MDA5 pathway was functional. To confirm this analyses DNA microarray analyses on the colon cancer cells following stimulation of the STING pathway using transfected cytosolic DNA was carried out. This data indicated significant suppression of STING-dependent primary innate immune gene activation in the colon cancer cells analyzed, including type I IFN, as well as a host of other key innate immune modulatory genes such as CXCL10, CXCL11 and CCl5 (FIGS. 4E and 4F). LoVo cells were observed to retain some ability to induce cytosolic DNA-induced cells, while HT116 cells appeared significantly defective in STING-dependent signaling. The data indicates that STING-dependent innate immune pathways appear to be preferentially deregulated in colonic tumor lines.

To analyze the mechanisms of STING inactivation further, immunohistochemical (MC) analyses were carried out on the normal or the colon tumor cells. It had been previously shown that in the presence of cytosolic DNA, STING becomes activated and translocates via a non-canonical autophagy associated process required for the activation of transcription factors NF-κB and IRF3 (interferon regulatory factor 3). Thus, blockage of STING translocation through use of Brefeldin A or through suppression of the key autophagy modulator VPS34 inhibits STING signaling function. Thus, normal or human colon cancer cells were transfected with dsDNA to activate STING and it was observed that only 4/11 cell-lines (LS123, SW480, LoVo and HT29) exhibited evidence of STING trafficking (FIG. 5A). This study was then completed by analyzing the translocation of the transcription factors NF-κB and IRF3 in similarly treated cells using IHC techniques. It was observed that IRF3 was able to translocate in cells that facilitated STING trafficking, except for SW480 (FIG. 5B). This may explain, in part, the partial stimulation of innate immune genes in some of the cells analyzed by microarray, such as LoVo. However, only two of the cells (LS1116, LS123) exhibited translocation of the NF-κB subunit p65 (FIG. 5C). Since both IRF3 and NF-κB are required for optimal transcription of type I IFN, it may explain why LS1116 and LS123 remained partially able to stimulate type I IFN production, following treatment with cytosolic DNA, while the remainder did not (FIGS. 4B and 4C). However, cytosolic DNA-dependent, STING-controlled signaling remained severely defective in all colon cancer types examined as shown (FIG. 4).

Figure 5D:
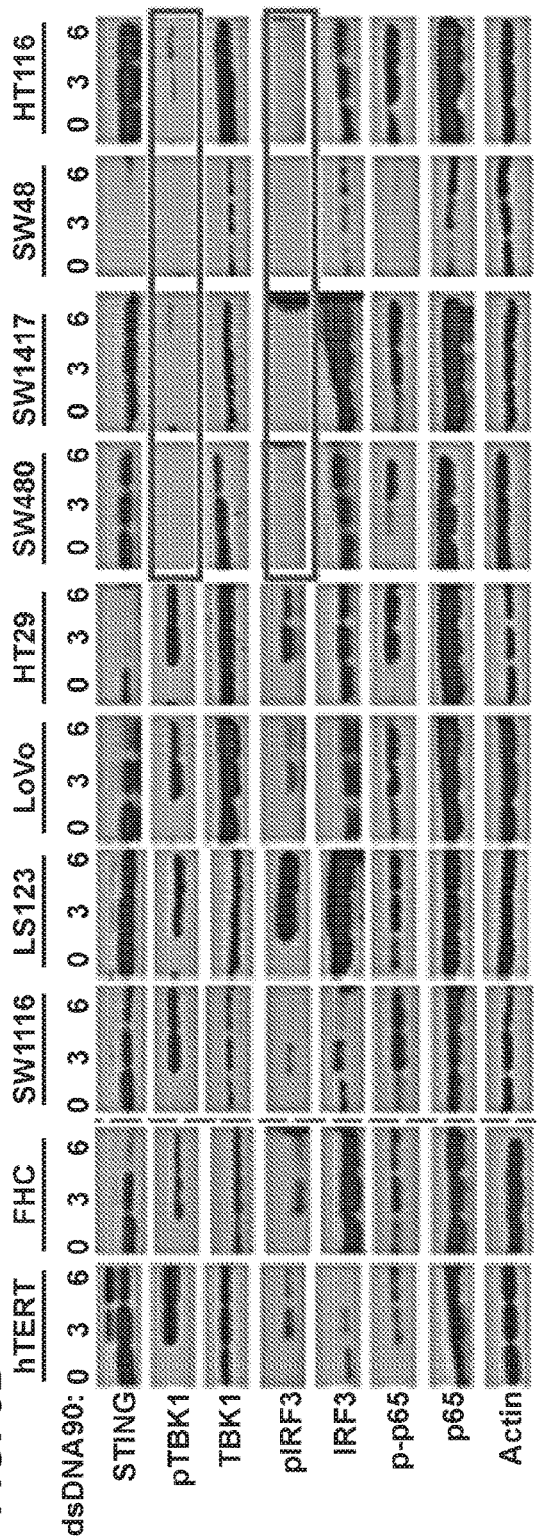

To extend these findings further, immunoblot analyses were carried out on the normal or colon tumor cells. In the presence of cytosolic DNA, STING undergoes phosphorylation and is then degraded, an event that facilitates its activity, perhaps through releasing TBK1 to phosphorylate IRF3. First, STING phosphorylation/degradation after activation was impeded in many cell lines analyzed, which may affect STING function (for example, LS123, SW480, SW1417, HT116) (FIG. 5D). Confirmation was made in tumor cells that exhibited some STING trafficking (LS1116, LS123, LoVo and HT29) that the IRF3 kinase activator Tank binding kinase 1 (TBK1) underwent phosphorylation in the presence of cytosolic DNA (FIG. 5D). Accordingly, observations of phospho-IRF3 activity in cells with active TBK1 (FIG. 5D) were made. The remainder of the tumor cells, such as SW480, SW1417, SW48 and HT116 did not exhibit phospho-TBK1 activity or IRF3 translocation, likely due to an inability of STING to undergo autophagy, or since STING expression was completely absent as in the case of SW48 (FIG. 5D). Surprisingly, observations showed that the vast majority of cells lacked p65 translocation, phosphorylation of p65 was evident (for example LoVo, HT29, SW480 and SW1417). This may suggest that NF-κB signaling could be defective at the level of p65 translocation. Taken together the study clearly indicates that STING-signaling is defective in a wide variety of colon cancer cells examined.

Cyclic Dinucleotides (CDN's) have been Shown to Activate STING.

Figure 5F:
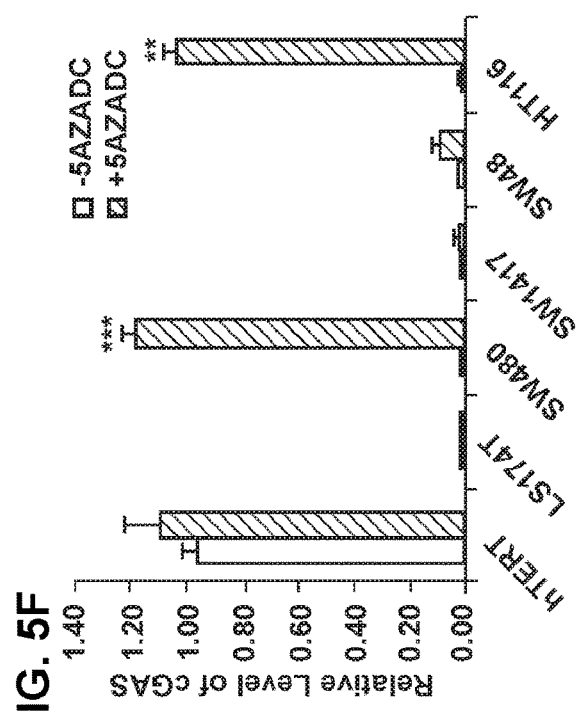
Figure 5E:
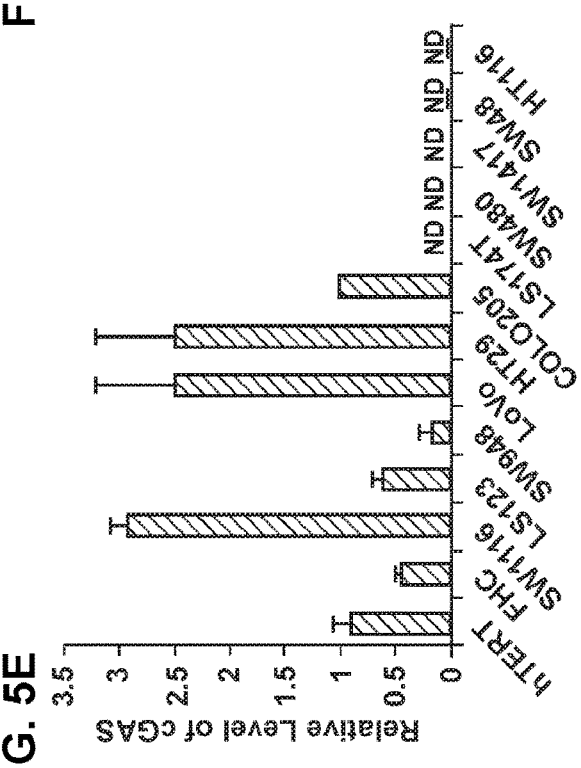
Figure 13A:
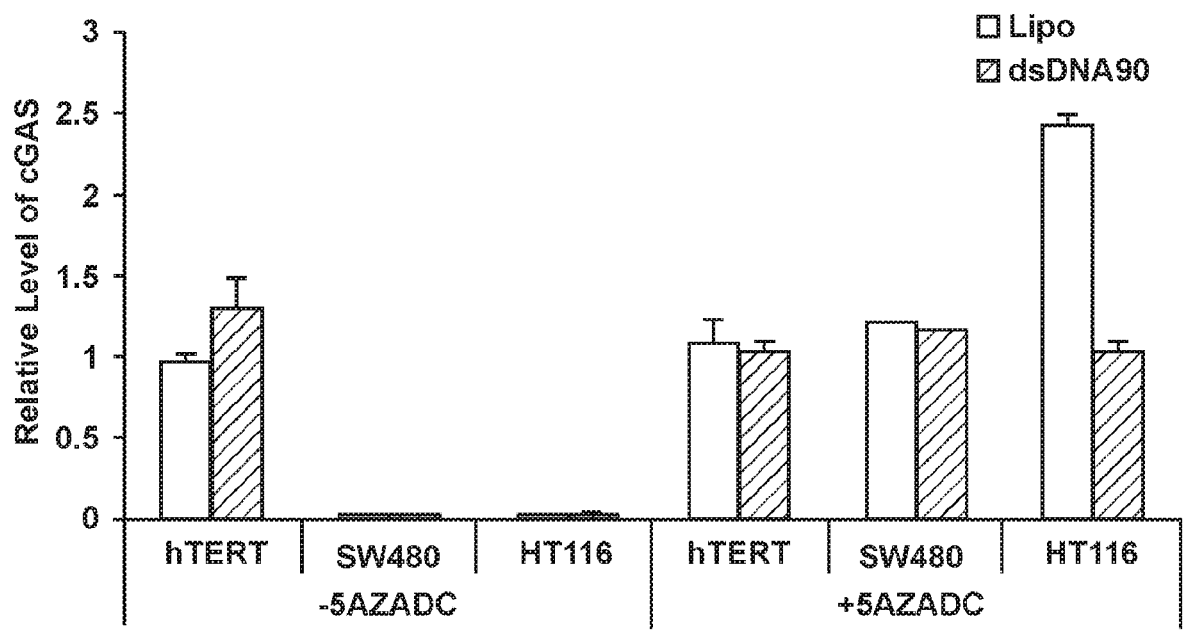
FIGS. 13A-13D show human colon cancer cells (SW480 and HT116) as well as hTERT cells were treated with 1 uM 5azacytidine for 7 days, followed by dsDNA90 transfection at 3 µg/ml for 3 hours. Total RNA was extracted and analyzed by qPCR for cGAs (FIG. 13A) and IFNB (FIG. 13B) expression.
Figure 13B:
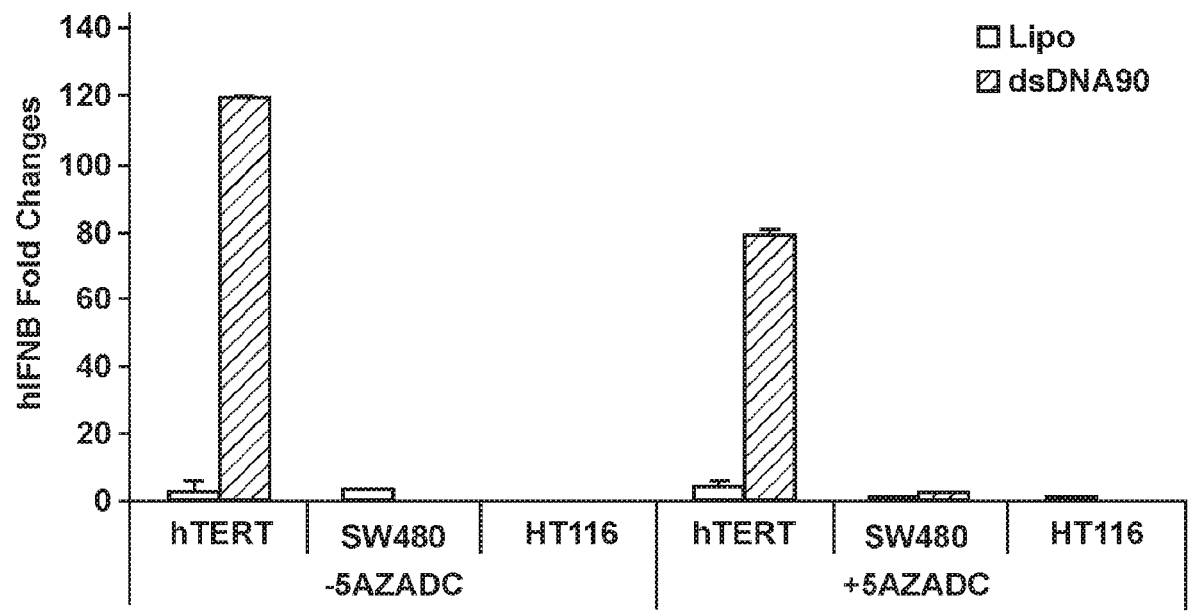
Figure 13C:
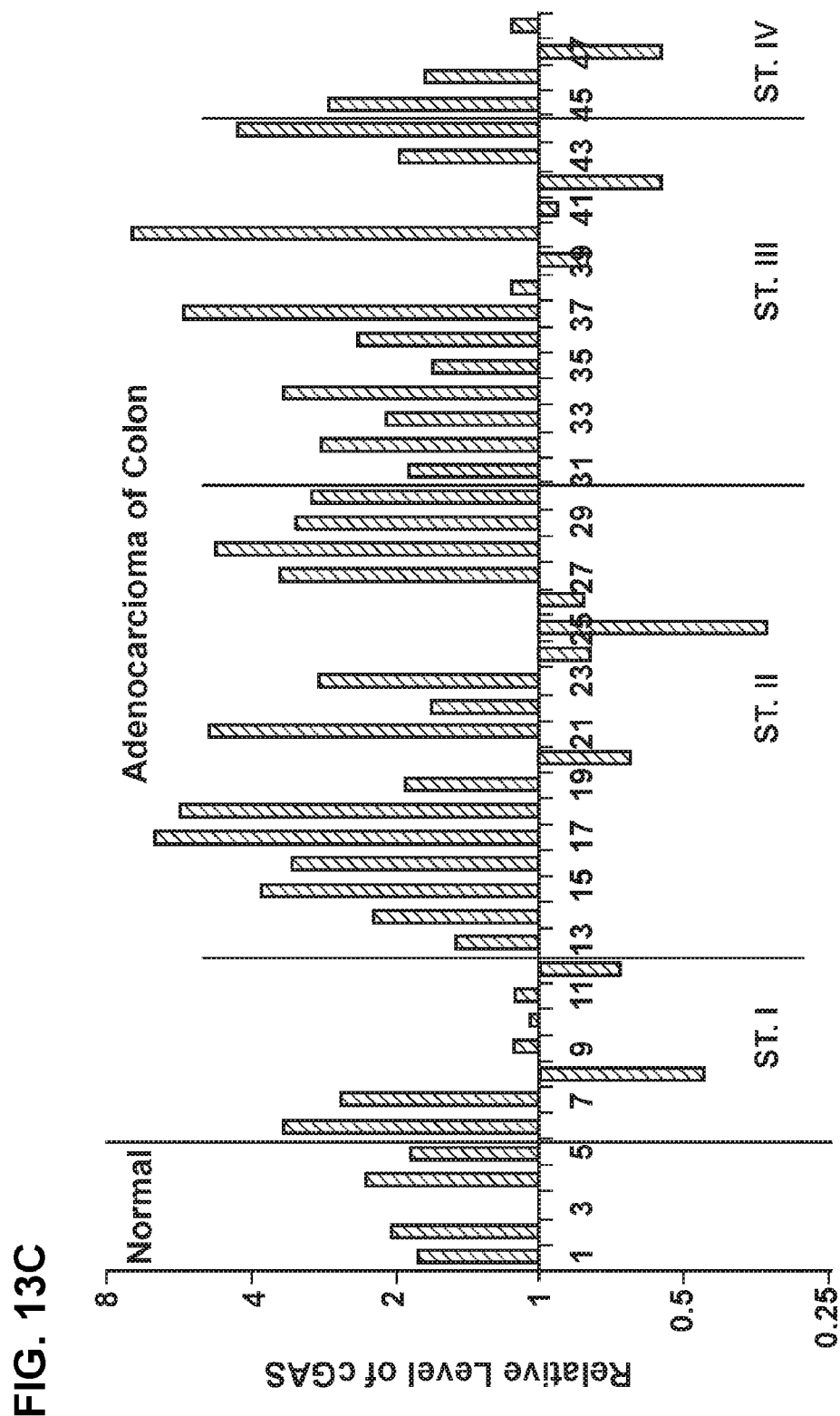
Figure 13D:
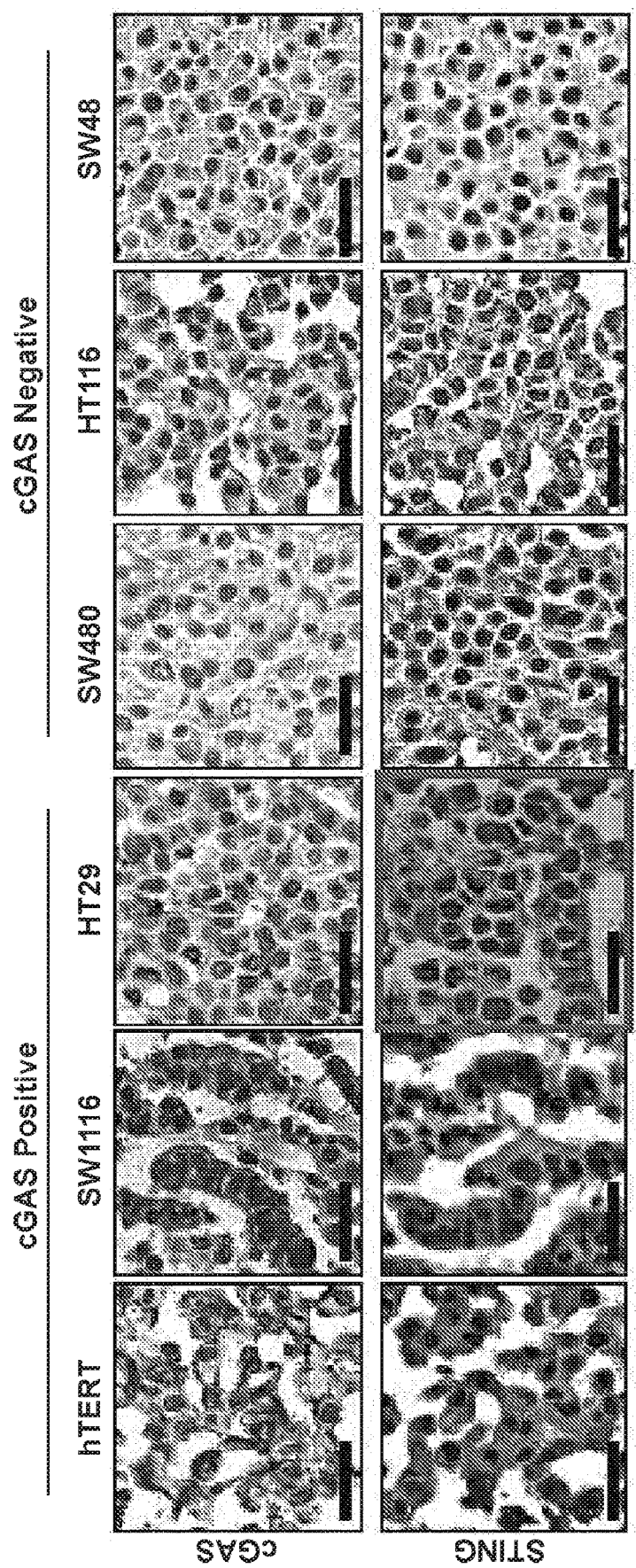
Figure 14A:
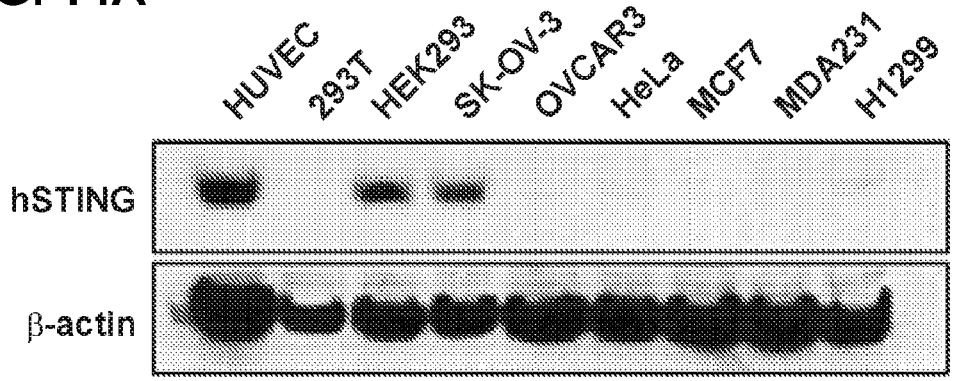
FIGS. 14A-14C show (FIG. 14A), immunoblot of STING in various transformed or cancer derived human cell lines. HUVEC was a positive control.
Figure 14B:
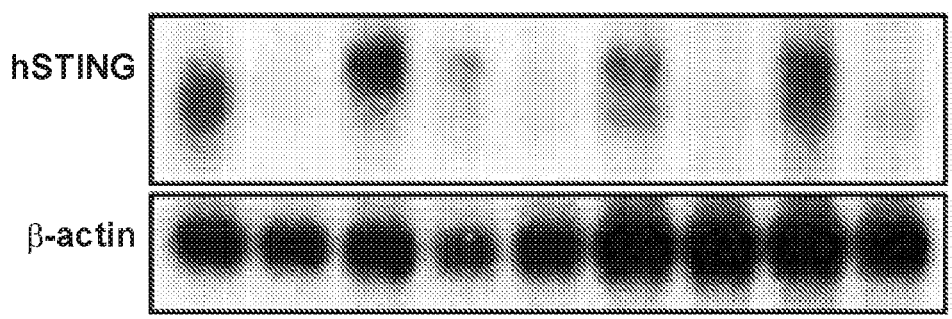
Figure 14C:
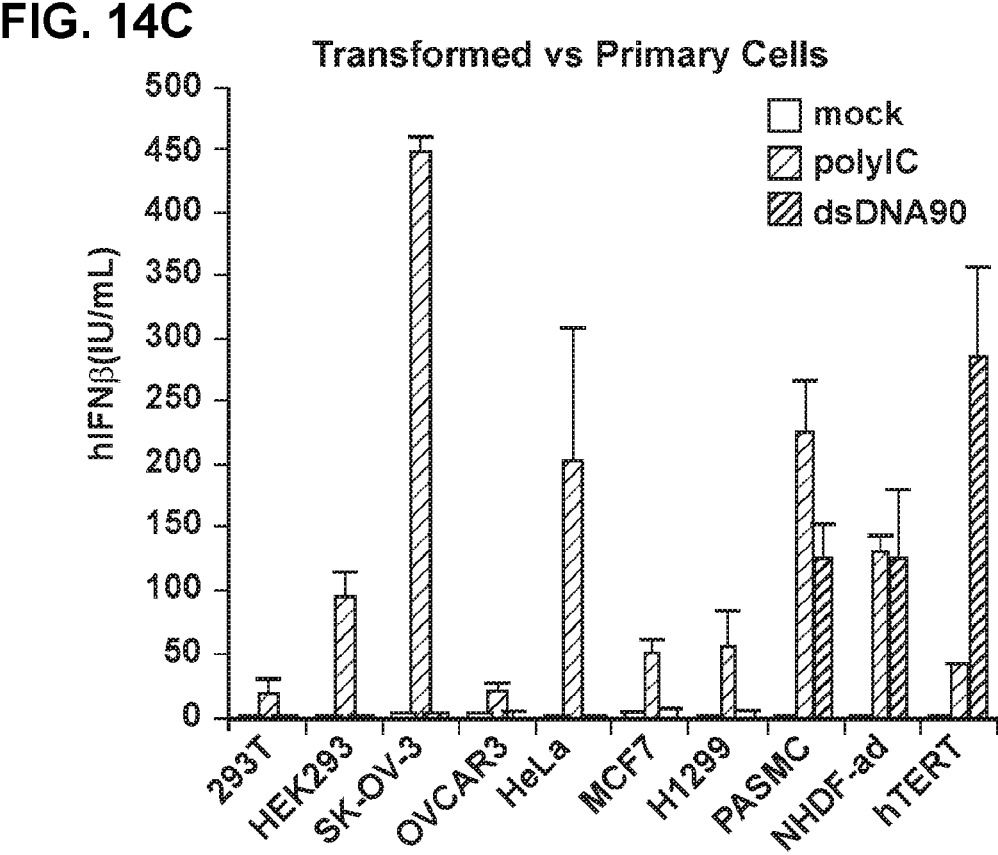

CDN's have been shown to be generated through cytosolic dsDNA species triggering the activation of a synthase, referred to as cGAS (Cyclic GMP-AMP Synthase, C6orf150, Mab-21 Domain-Containing Protein). Loss of cGAS has thus been shown to affect STING signaling. To complement the above study, the expression of cGAS in the colon cancer cell-lines was examined. This analysis indicated that 5/11 colon cancer cells had undetectable levels of cGAS expression, an event that correlated with loss of STING translocation and TBK1/IRF3 activity (FIGS. 5D and 5E highlighted by dashed line or box). Interestingly, loss of cGAS expression could be rescued using de-methylating agents lines (SW480, HT116) indicating that some cells exhibited suppressed cGAS promoter activity (FIG. 5F). However, rescue of cGAS expression did not robustly rescue STING activity as determined (FIGS. 13A and 13B) indicating that further defects in STING signaling may exist in these cells. Given these findings, examination of the expression of cGAS in 47 human colon cancers at various stages of tumorigenesis was analyzed (FIG. 13C). Expression of cGAS was low to undetectable in approximately 30% of cells analyzed. Thus, defects in cGAS or STING expression, or signaling appear defective in a large number of tumor colon cancer cells lines and could constitute a major cause of tumorigenesis. It should be noted, however, that similarly defective STING-signaling was found in a wide variety of other tumor cells examined, indicating that defects in STING function could be common in cells other than those of the colon (FIG. 14).

Cancer Cells with Defective STING Signaling are Susceptible to Viral Oncolysis.

Figure 6A:
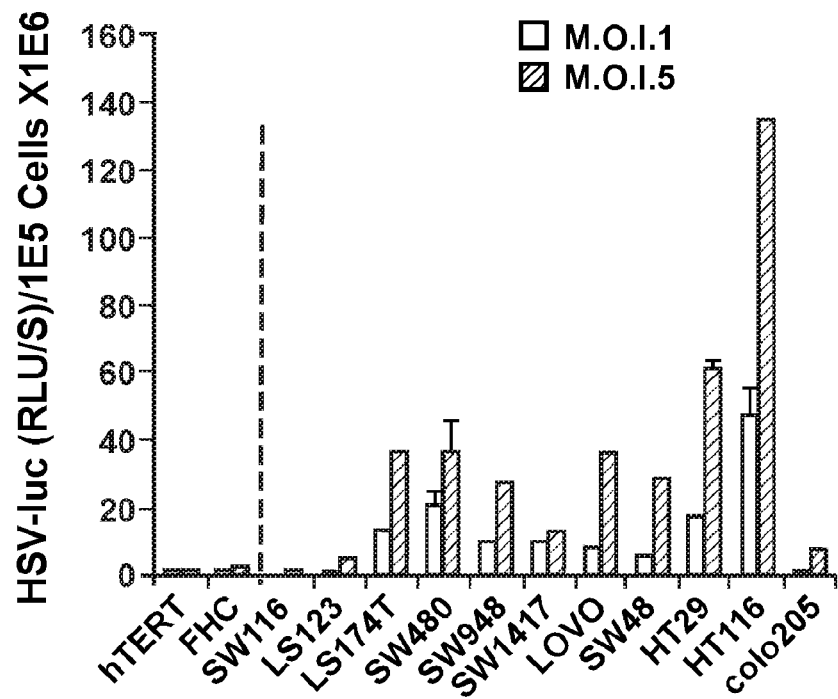
FIGS. 6A-6D show HSV1 viral production is more effective in colon cancer cells that have defected STING innate immune pathway.
Figure 6B:
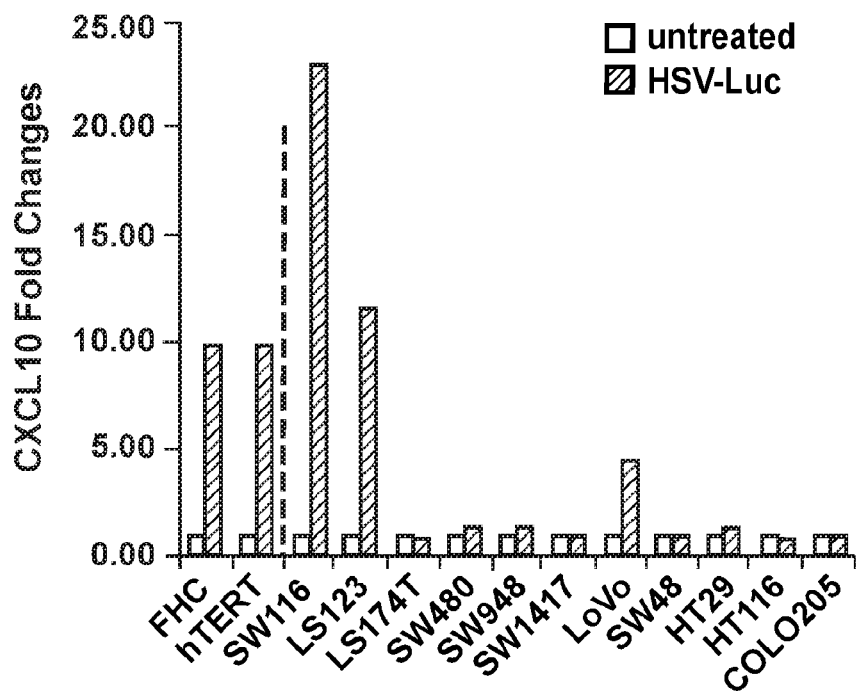
Figure 6C:
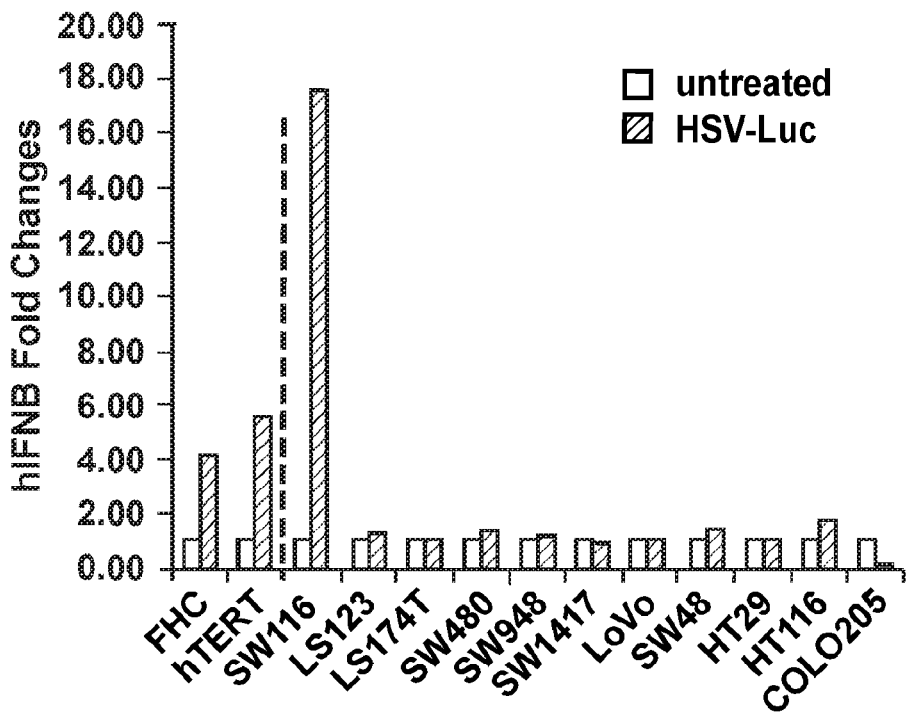
Figure 6D:
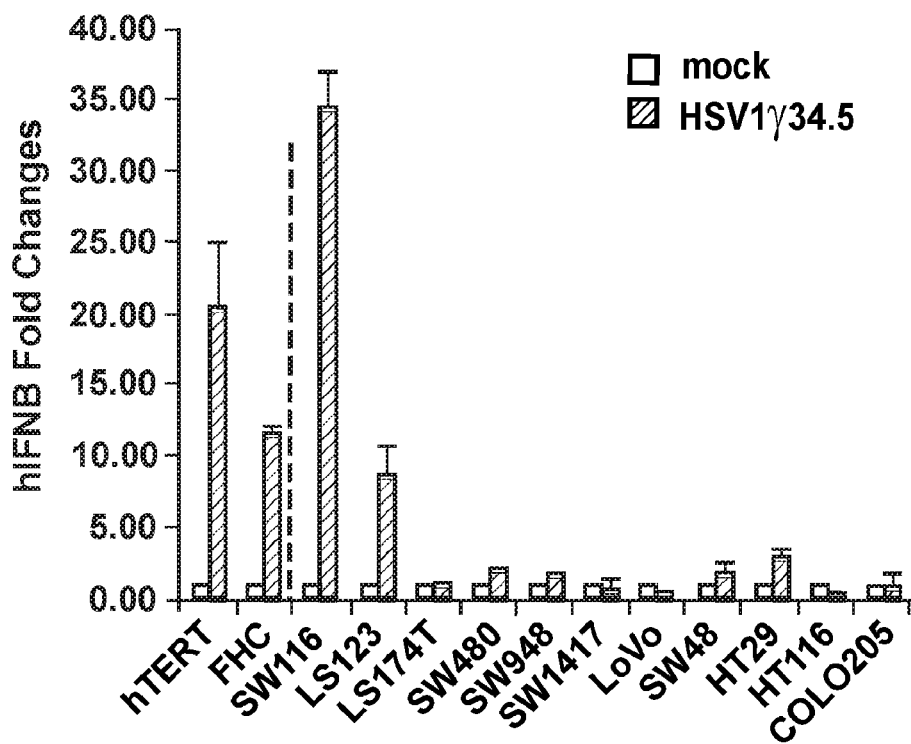

Numerous cancer cells have been shown to be defective in antiviral responses, although the mechanisms remain to be fully determined. Indeed, a variety of viruses are now being used in the clinic to determine their efficacy as anti-tumor therapeutics, including herpes simplex 1 (HSV1) which harbors a dsDNA genome. HSV1 has been shown to potently trigger innate immune responses through activating the STING. Mice deficient in STING signaling are extremely sensitive to lethal HSV1 infection since they lack the ability to mount an appropriate innate immune response, including the generation of type I IFN. Given the findings that STING signaling is defective in a large number of cancer cells, their susceptibility to HSV1 infection was examined. First, analysis of the response to a recombinant HSV1 that expresses luciferase (HSV1-Luc) was made. This analysis indicated that colon cancer cells exhibiting defective STING signaling enabled high levels of HSV1-Luc expression (FIG. 6A). However, the two cancer lines (SW116 and LS123), which exhibited partial STING-dependent innate immune responses (FIG. 4B-D), as well as the control hTERT and FHC's did not facilitate robust HSV-Luc gene expression (FIG. 6A). This coincided with the normal cells and SW116 and LS123 responding to infection by producing CXCL10, similar to their response to dsDNA (FIGS. 6B and 6C; FIG. 4C). None of the tumor cells harboring severely defective STING function could robustly produce type I IFN after infection. To extend this study, an HSV construct that lacked the γ34.5 gene (HSV1 γ34.5) was used, encoding viral protein that has been reported to inhibit host defense in part through preventing host cell translational shut-off. A similar virus that lacks γ34.5 is being examined in the clinic as an anti-cancer agent. It was observed that colon cancer cells defective in STING-signaling were unable to mount an efficient type I IFN response following infection with HSV1 γ34.5 (FIG. 6D). Thus, the examination of STING-signaling may be a useful prognostic marker for whether HSV1 or other viral based anti-cancer therapies will be efficacious for the treatment of malignant disease.

Experimental Procedure

Mice:

STING knockout mice (SKO, Sting$^{-/-}$) were generated in the University of Miami laboratory (Ishikawa 2008). Wild type mice (WT) were used as control groups. Mice care and study were conducted under approval from the Institutional Animal Care and Use Committee (IACUC) of the University of Miami.

Acute DSS Colitis.

WT and SKO mice 6-8 weeks of ages were divided into experimental and control groups. Mice in experimental group received 3% Dextran sodium sulfate (DSS, MP 160110; MW 36000-5000) for 5 days, followed by 2 days of regular drinking water. Distilled water was administered into control group mice.

AOM/DSS Induced Colitis-Associated Tumor Induction:

WT and SKO mice were injected intraperitoneally with Azoxymethane (AOM; MP 180139; MW 74.08) at a dose of 10 mg/kg. DSS at 5% which was administered in the drinking water for 7 days every 3 weeks. DSS cycle was repeated 4 times. On 91 days, micro endoscopic procedure was performed in a blinded fashion for counting number of polyps. Mice were sacrificed at day 121 and colon was resected, flushed with PBS, fixed in formalin for histology and frozen for RNA expression analysis.

Primary Cell Culture:

Mouse embryonic fibroblasts (MEFs) were obtained from e15 embryos by a standard procedure as described. Bone marrow derived dendritic cells were isolated from hind-limb femurs of 8-10 weeks old mice. Briefly, the marrow cells were flushed from the bones with Dulbecco's modified eagle medium (DMEM, Invitrogen), 10% heat-inactivated fetal calf serum (FCS, Invitrogen) with a 23 gauge needle and incubated at 37° C. for 4 hours. After harvesting floating cells, approximately 2×10$^7$ cells were seeded in 10 cm dish with complete DMEM including 10 ng/ml of Recombinant mouse GM-CSF (GM-CSF, BioLegend) for CD11c positive dendritic cells. After 1 week, bone marrow derived dendritic cells were obtained. Normal human colon epithelial cells and colon cancer cell lines were purchased from ATCC and cultured in their appropriate growth media according to the ATCC instructions. Media and supplements are from Invitrogen. hTERT-BJ1 Telomerase Fibroblasts (hTERT) were originally purchased from Clontech and were cultured in 4:1 ratio of DMEM:Medium 199 supplement with 10% FBS, 4 mM L-Glutamine and 1 mM sodium pyruvate at 37° C. in a 5% CO2-humidified atmosphere.

Gene Array Analysis:

Total RNA was isolated from cells or tissues with RNeasy Mini kit (74104, Qiagen, Valencia, Calif.). RNA quality was analyzed by Bionalyzer RNA 6000 Nano (Agilent Technologies, Santa Clara Calif.). Gene array analysis was examined by Illumina Sentrix BeadChip Array (Mouse WG6 version 2) (Affymetrix, Santa Clara Calif.) at the Oncogenomics Core Facility, University of Miami. Raw intensity values from Illumina array are uploaded on GeneSpring™ software from Agilent. Values are Quantile normalized and log 2 transformed to the median of all samples. Significantly differential expressed genes are computed using the Student's t-test and selected using threshold of P-value≤0.05. Hierarchical Clustering and visualization of selected differentially expressed genes is performed on GeneSpring using Pearson Correlation distance method and linkage was computed using the Ward method. Gene expression profiles were processed and statistical analysis was performed at the Sylvester Comprehensive Cancer Center Bioinformatics Core Facility University of Miami.

Histopathology.

Mice were sacrificed and the colon tissues were fixed in 10% formalin for 48 hours. All processes for paraffin block and Hematoxylin and Eosin staining (H&E) were performed at the pathology research resources histology laboratory in University of Miami.

Statistical Analysis:

All statistical analysis was performed by Student's t test unless specified. The data was considered to be significantly different when $P<0.05$.

Supplemental Information

Quantitative Real Time PCR (qPCR):

Total RNA were reverse-transcribed using M-MLV Reverse Transcriptase (Promega). Real-time PCR was performed using Taqman Gene Expression Assay (Applied Biosystems) for innate immune genes and inflammatory cytokines (Cxcl10: Mm00445235, Ifit3: Mm0170846).

Immunoblot Analysis:

Equal amounts of proteins were resolved on sodium dodecyl sulfate (SDS)-Polyacrylamide gels and then transferred to polyvinylidene fluoride (PVDF) membranes (Millipore). After blocking with 5% Blocking Reagent, membranes were incubated with various primary antibodies (and appropriate secondary antibodies). The image was resolved using an enhanced chemiluminescence system ECL (Thermo Scientific) and detected by autoradiography. Antibodies: rabbit polyclonal antibody against STING was developed in the laboratory; other antibodies were obtained from following sources: β-actin (Sigma Aldrich), p-IRF3 (Cell Signaling), IRF3 (Santa Cruz Biotechnology), p-TBK1, TBK1, p-p65, p65.

Interferon β ELISA Analysis:

Interferon β (IFNB, IFNβ) Elisa was performed using either the IFNβ human ELISA Kit from Invitrogen or the Human IFNβ ELISA Kit from PBL Interferon Source following the manufacturer's protocol.

Immunofluorescence Microscopy:

Cells were cultured and treated in their appropriate media on Lab-Tek II chamber slides. Cell were fixed with 4% paraformaldehyde for 15 minutes in at 37° C. and permeabilized with 0.05% Triton X-100 for 5 minutes at room temperature. Immunostaining was performed with rabbit-anti-STING polyclonal followed by fluorescence conjugated secondary antibodies (FITC-goat-anti-rabbit) (Invitrogen). Images were taken with Leica SP5 confocal microscope at the Image Core Facility, University of Miami.

Northern Blot Analysis:

Northern blot was performed with 5 μg of polyA RNA using NorthernMax®-Gly Kit (Ambion). Briefly, RNA was resolved in 1% Glyoxal gels, transferred to the BrightStar®-Plus Nylon Discussion Demonstrated here is a protective role for STING in the prevention of CAC induced by AOM/DSS carcinogenic treatment. Data indicates that this event may occur in large part through STINGS ability to control the production of IL-22BP. Following tissue damage, for example by DSS, IL-22 is induced and manifests protective, wound healing effects, including the promotion of tissue regeneration. However, if left uncontrolled, IL-22 can also endorse tumor development. Thus, IL-22 is tightly regulated by secreted IL-22BP, which is expressed by CD11c$^+$ dendritic cells. The importance of IL-22BP in controlling IL-22 has been emphasized through observing that IL-22BP-deficient mice are also susceptible to AOM/DSS induced CAC, similar to STING-deficient mice. Nevertheless, IL-22 may have dual functions since mice lacking IL-22 have also been reported to exhibit enhanced inflammatory responses when treated repeatedly with DSS, plausibly because complete loss of IL-22 may cause a delay in intestinal repair which in turn may actually aggravate inflammatory processes. The production of IL-22 BP can be suppressed by IL-18, which is known to be induced early after DSS-induced intestinal damage. Accordingly, IL-18-deficient mice are also susceptible to colon cancer, presumably through chronic suppression of IL-22 activity, by unregulated IL-22BP, which may mimic the situation observed with IL-22-deficient mice. Nevertheless, the control of IL-22BP remains to be fully clarified since down regulation of IL-22BP has also been reported to occur in the absence of IL-18. In addition, it is known that loss of the TLR and IL-1R/IL-18R adaptor MyD88 also renders mice sensitive to CAC, in part due to loss of IL-18R signaling. Finally, susceptibility to AOM/DDS-induced CAC has been shown to be enhanced in mice lacking Caspase-1, the adaptor PYCARD (Apoptosis-associated speck-like protein containing a CARD; ASC) or nucleotide-binding domain, leucine rich repeat and pyrin domain containing proteins 3 and 6 (NLRP3/6), presumably since Pro-IL-18 produced by epithelial cells or dendritic cells requires cleavage prior to secretion into an active form.

Data here indicates that IL-18 is inducible by dsDNA, or CDN's, or by AOM/DMH in a STING-dependent manner. Similar to the situation with IL-22, it is proposed that intestinal damage triggers STING activity (as a consequence of DNA damage or even from microbial ligands such as CDN's or DNA). This results in the up-regulation of IL-18 and down-regulation of IL-22BP, which would enable IL-22 to promote tissue repair. However, similar to the situation with IL-22, long term loss of STING may delay wound repair, facilitate microbial invasion trigger inflammation which would actually aggravate tumorigenesis. It was noted that IL-18 expression was not totally ablated in tumors from SKO mice, presumably since the expression of this cytokine could be induced by other pathways. Despite this, IL-22BP levels remained low in SKO mice demonstrating the importance of STING in IL-22BP regulation. Collectively, the data indicates that STING plays a key role in controlling intestinal tissue damage and CAC through regulating IL-22BP's suppression of IL-22.

Given that loss of STING invokes a pro-tumorigenic state, at least in part through an inability to transiently promote tissue repair or to signal DNA damaging events to the immune system via secretion of cytokines, the expression and function of STING in normal and cancer-related colon cells was explored. The study indicated that STING was expressed in the majority of colon cancer cells analyzed. However, it was observed that STING function was almost completely defective in greater than 80% of the examined cells. Defects in STING signaling were also observed in a wide variety of other tumor cells studied (FIG. 14). STING may associate with nucleic acids while CDN's are potent stimulators of STING activity. Cytoplasmic DNA can bind to the synthase cGAS and generate CDN's which then bind to and activate STING. This event invokes STING trafficking with TBK1 via non-canonical autophagy processes, to endosomal regions harboring the transcription factors IRF3 and NF-κB, resulting in cytokine activation. The data indicates that STING did not respond to transfected DNA and in many instances failed to translocate. In these situations a lack of IRF3 activity and translocation was observed. Interestingly, loss of STING trafficking coincided with a loss of cGAS expression (in greater than 30% of cases), presumably since CDN's were unavailable to facilitate STING function. In other situations, defects in NF-κB activity were observed. Since both NF-κB and IRF3 activity are required for the optimal production of type I IFN and other cytokines, loss of either or both of these pathways would have detrimental effects on STING's ability to stimulate the transcription of host defense genes, such as IL-18 or type I IFN, required for efficient anti-tumor T cells responses. It is proposed that loss of STING signaling may enable DNA damaged cells to escape immune surveillance and even promote inflammatory events due to an inability to repair damaged intestinal walls which may be vulnerable to invading microbes.

Finally, it has been previously shown that STING plays a key role in protecting against DNA virus infection. Since it was observed that STING function was ablated in nearly all tumor cell-lines examined thus far, these cells' susceptibility to HSV1 and vaccinia virus (VV) infection was examined. The study indicated that colon cancer cells harboring defects in STING function were highly sensitive to HSV1 and vaccinia virus infection. A number of oncolytic viruses, including HSV1, are being considered in the clinic as anti-tumor therapeutics, although understanding the mechanisms of action remain to be fully determined. The data here provides information on the causes of intestinal tumorigenesis and may provide prognostic information to dictate the success of oncolytic viral therapy, and even disease outcome including response to chemotherapeutic treatments.

Example 2

STING Function in Colorectal Adenocarcinoma

Figure 4G:
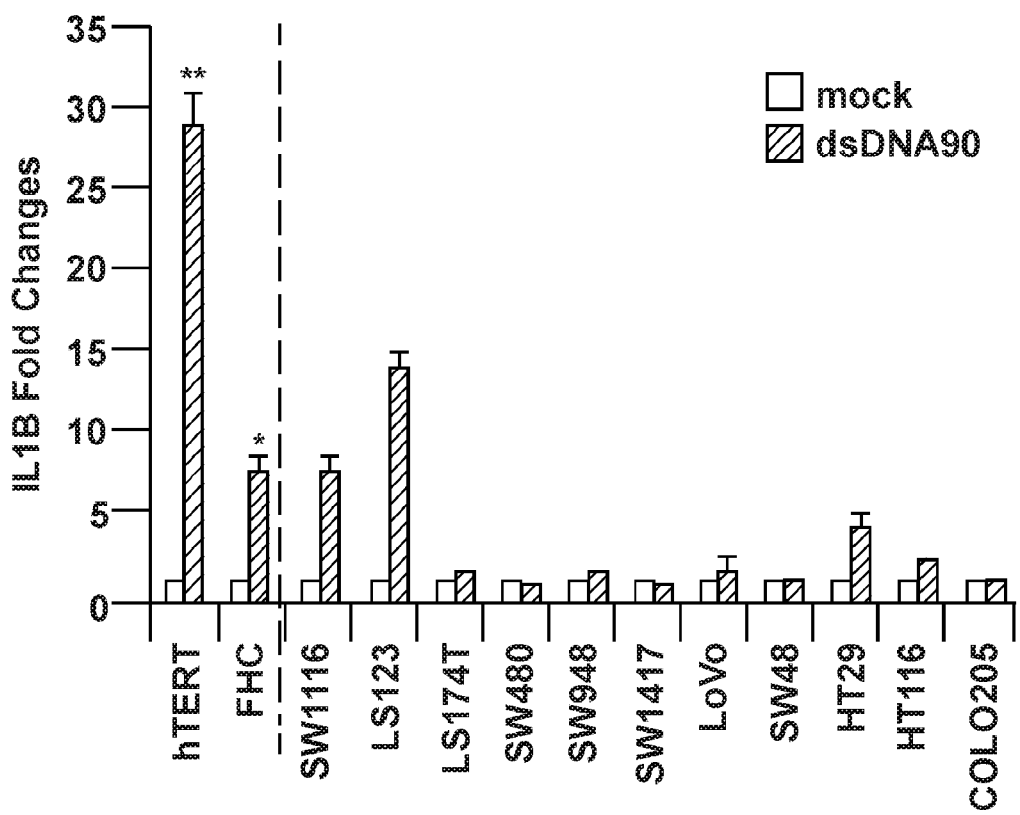
Figure 18A:
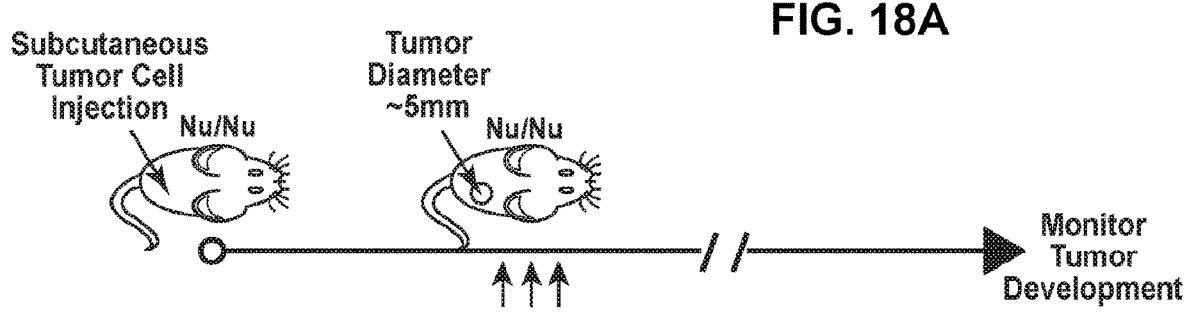
FIGS. 18A-18E show increased HSV1γ34.5 oncolytic effect was observed in colon cancer cells with impaired STING signal in vivo.
Figure 18B:
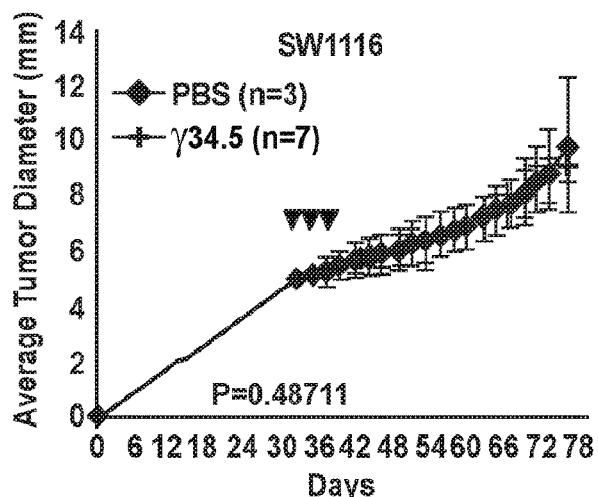
Figure 18C:
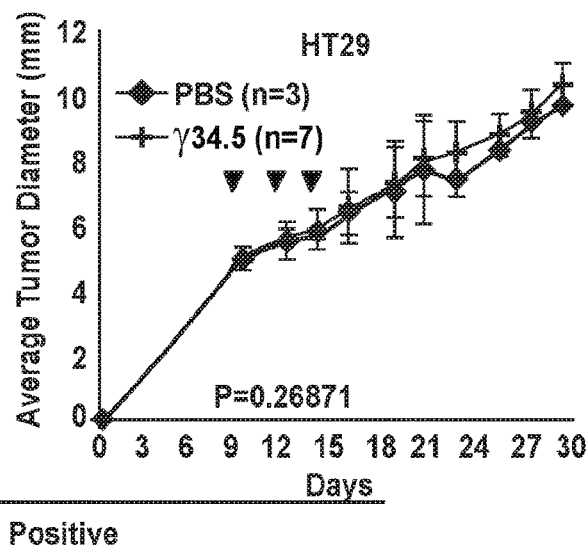
Figure 18D:
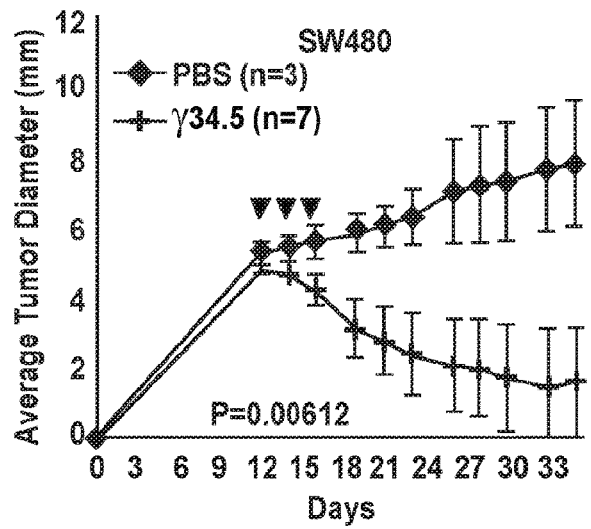
Figure 18E:
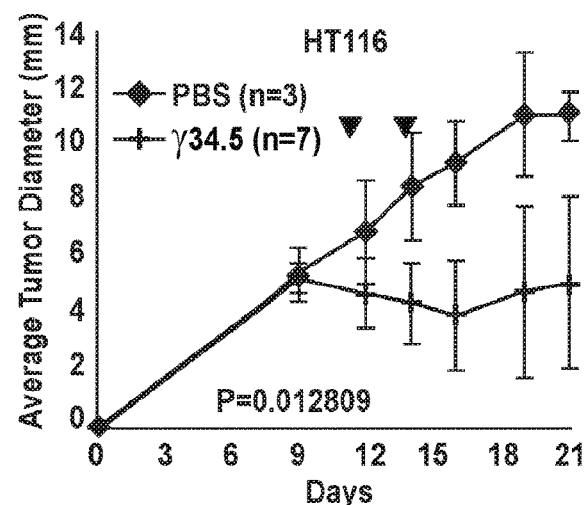
Figure 19:
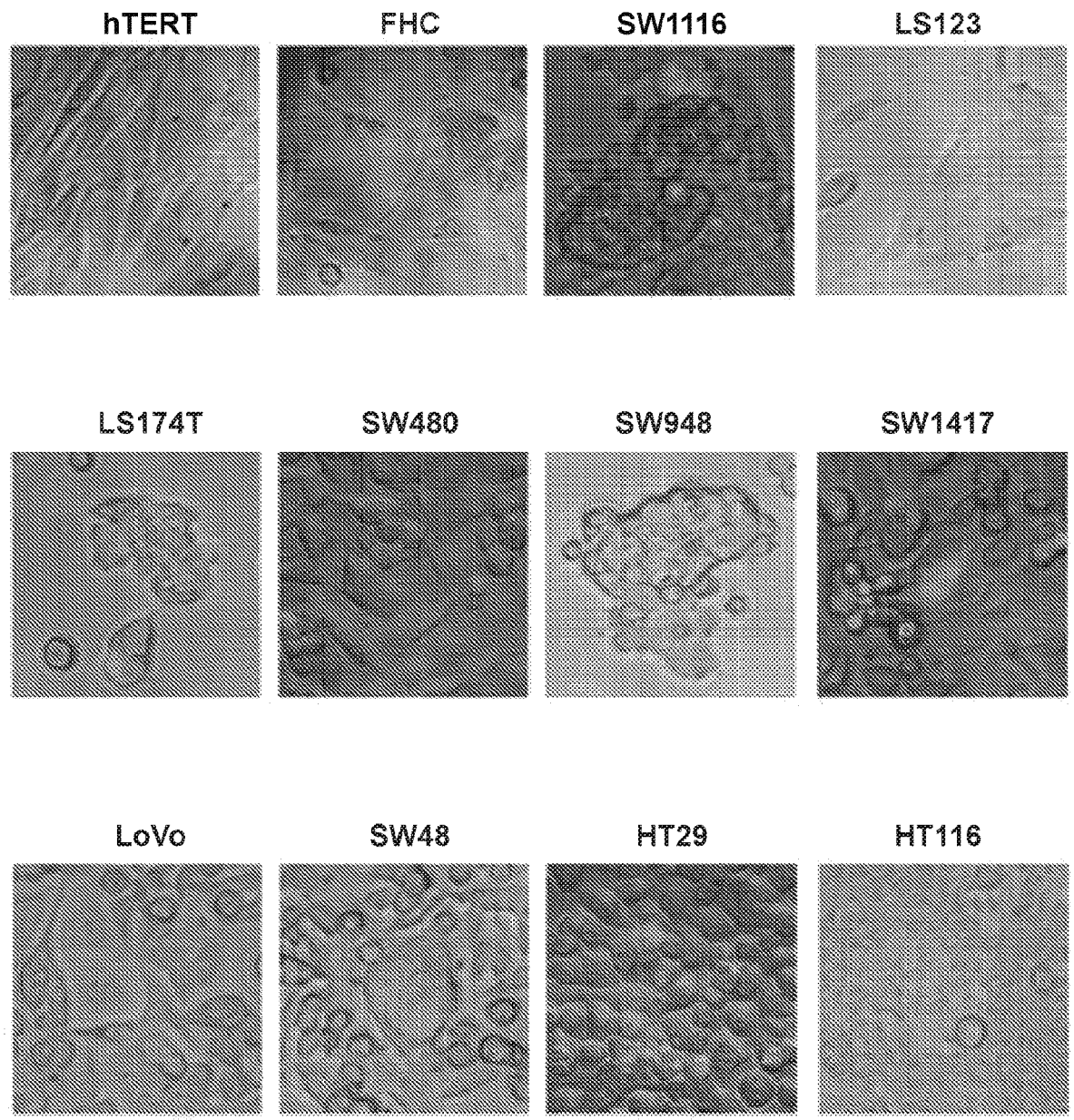
FIG. 19 shows dsDNA90 transfection efficiency into colon cancer cell lines monitored with FITC-dsDNA90 3 hours post Lipofectamine 2000 transfection under fluorescent microscopy. Images shows at 400×.

Defective STING Signaling in Colorectal Adenocarcinoma Cells:

STING-deficient mice have been reported to be prone to AOM/DSS-associated CAC. However, whether STING function is deregulated to any extent in human colorectal adenocarcinoma (CA) is unknown. To start to evaluate this, STING expression was examined by immunoblot in a variety of CA cells, generated from cancers diagnosed at various stages as described by Duke's system. Results indicated that STING was expressed in 10 out of 11 cell lines examined, albeit at varying levels (FIG. 4A). To correlate expression levels with STING function, cells were transfected with dsDNA to activate STING signaling, or with dsRNA (polyI: C) to activate the RIG-I like pathway. Type I IFN expression was measured by ELISA, which is known to be STING-inducible. It was noted that all 11 CA cells responded poorly to dsDNA-triggered type I IFN production (FIG. 4B). It was confirmed that all cells were transfected adequately using FITC-labeled dsDNA activator and immunofluorescence analysis (FIG. 18). This was in contrast to control hTERT cells or normal colon epithelial cells (FHC), which when transfected with dsDNA did express IFNβ. In contrast, 8 of the 11 CA cells were able to produce type I IFN, in various amounts, in response to dsRNA, indicating that the RIG-I-Like pathway retained function in the majority of cases examined (FIG. 4B). A similar finding was noted upon examination of CXCL10 mRNA production by RT-PCR, although some CXCL10 was detected, albeit in low levels, in LoVo and HT29 in response to STING-dependent dsDNA transfection (FIG. 4D). To extend these findings further, IL-1β production was measured in the CA cells since it was previously noted that carcinogen triggered DNA damage can induce IL-1β through STING-signaling. Loss of IL-1β has been shown to render mice susceptible to CAC due to wound healing responses being impaired. This study indicated that IL-1β was produced in the normal hTERT and FHC cells by dsDNA, indicating the importance of STING-activity in this process. However, only 3 out of the 11 CA cells appeared able to produce IL-1β in response to dsDNA treatment, again suggesting that STING function is defective in the majority of CA cells examined (FIG. 4G). SW48, which lacked STING expression, did not appear responsive to dsDNA transfection in any capacity. RNAi treatment confirmed that the upregulation of these cytokines was STING-dependent (FIG. 19A-C). Given this data, a more detailed analysis of dsDNA-dependent STING signaling in CA cells was performed, by microarray analysis. CA cells were selected based on their ability to exhibit some STING function or not. For example, data from FIG. 4D, indicated that HT29 and LoVo cells were partially able to produce CXCL10 in response to dsDNA. In contrast, SW480 and HT116 were noted to be unable to produce CXCL10 to any significant level. Microarray analysis revealed that all the CA cells examined did not respond to dsDNA signaling as efficiently as control FHC cells, and confirmed the RT-PCR analysis (FIG. 4E, 4F). For instance, the level of CXCL10 was significantly higher in the control FHC cells compared to the CA cells analyzed. However, HT29 cells did appear able to retain some response to cytosolic dsDNA, more than any of the other CA cells examined, especially when compared to SW480 or HT116 (FIG. 4E, F). While HT29 was able to produce IFNβ moderately as determined by microarray analysis, IFNβ protein production was not readily evident by ELISA, perhaps due to low level expression, which was similarly observed even in the FHC controls (FIG. 4B). Nevertheless, taken together, the data indicates that a majority of CA cells exhibit defective STING-dependent signaling with only SW1116, LS123, LoVo and HT29 exhibiting some low level activity.

Loss of IRF3 Function in CA Cells:

To examine the extent of defective STING signaling in CA cells, immunofluorescence and immunoblot analysis was performed to evaluate NF-κB and IRF3 function. In the presence of dsDNA, STING rapidly undergoes trafficking from the ER, along with TBK1, to perinuclear-associated endosomal regions, containing NF-kB and IRF3, in a process resembling autophagy (Ishikawa and Barber, 2008; Konno et al., 2013). This event accompanies STING phosphorylation and degradation, likely to avoid sustained STING-activated cytokine production which can manifest inflammation. This approach confirmed that STING could traffic and undergo phosphorylation and degradation in the control hTERT and FHC cells, following treatment with dsDNA (FIGS. 5A and 5D, left panel). In these cells, TBK1 became phosphorylated as well as its cognate target IRF3 and the p65 subunit of NF-κB (FIG. 5D, left panel). IRF3 and p65 were also noted to translocate into the nucleus, as expected (FIG. 5B, 5C). A comparable effect was observed using SW1116 and LS123 CA cells which exhibited modest dsDNA-dependent IL-1β induction, confirming that the STING pathway retained some function in these two cells (FIGS. 5A-D and FIGS. 4C, D). Similarly, HT29 and LoVo displayed similar IRF3 translocation, but lacked p65 translocation. This likely explained that the defect in dsDNA-mediated innate immune gene induction rested in the inability of STING to trigger p65 translocation (FIGS. 5A-D and FIGS. 4E,4F). However, it was noted that the other CA cells, such as SW480, SW1417, SW48 and HT116, exhibited very little STING activity or trafficking. Similarly, little evidence of TBK1 or IRF3 phosphorylation/translocation was noted. Some indication of p65 phosphorylation was revealed, for example in SW480, but translocation of this transcription factor was not evident in any of these cells. STING expression was not observed in SW48 cells as previously described (FIGS. 4A, 5A, 5D). This data indicates that dsDNA-signaling is affected at various points of the STING pathway. For example, STING retains some activity and ability to traffic and escort TBK1 to IRF3, as in HT29 or LoVo cells, but NF-kB signaling is affected. In contrast, STING does not appear to undergo any phosphorylation or trafficking in SW480, SW1417, SW48 or HT116 cells, indicating that STING function is impeded upstream of IRF3/NF-kB interaction.

Figure 15A:
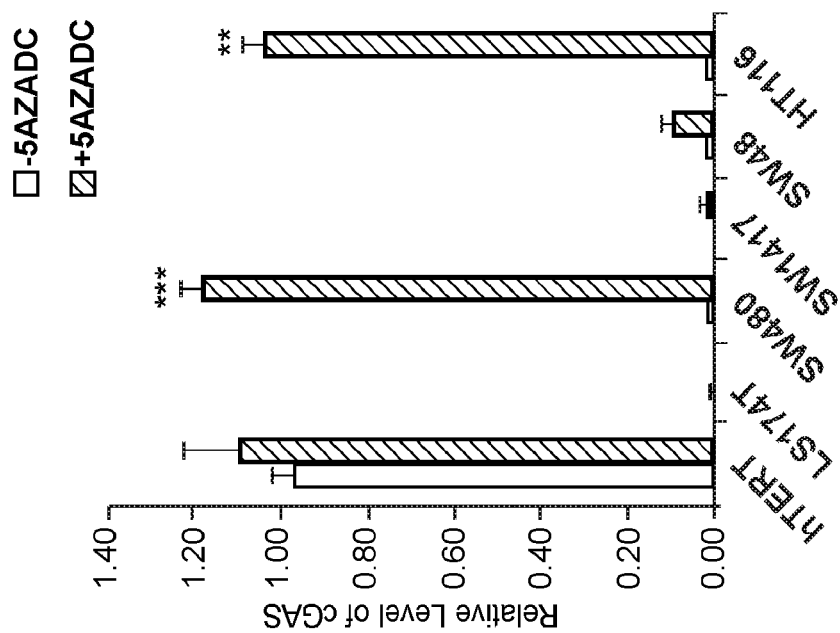
FIGS. 15A-15E show cGAS expression is suppressed in many human colon cancer cell lines and can be partially recapitulated through DNA demethylation.
Figure 15B:
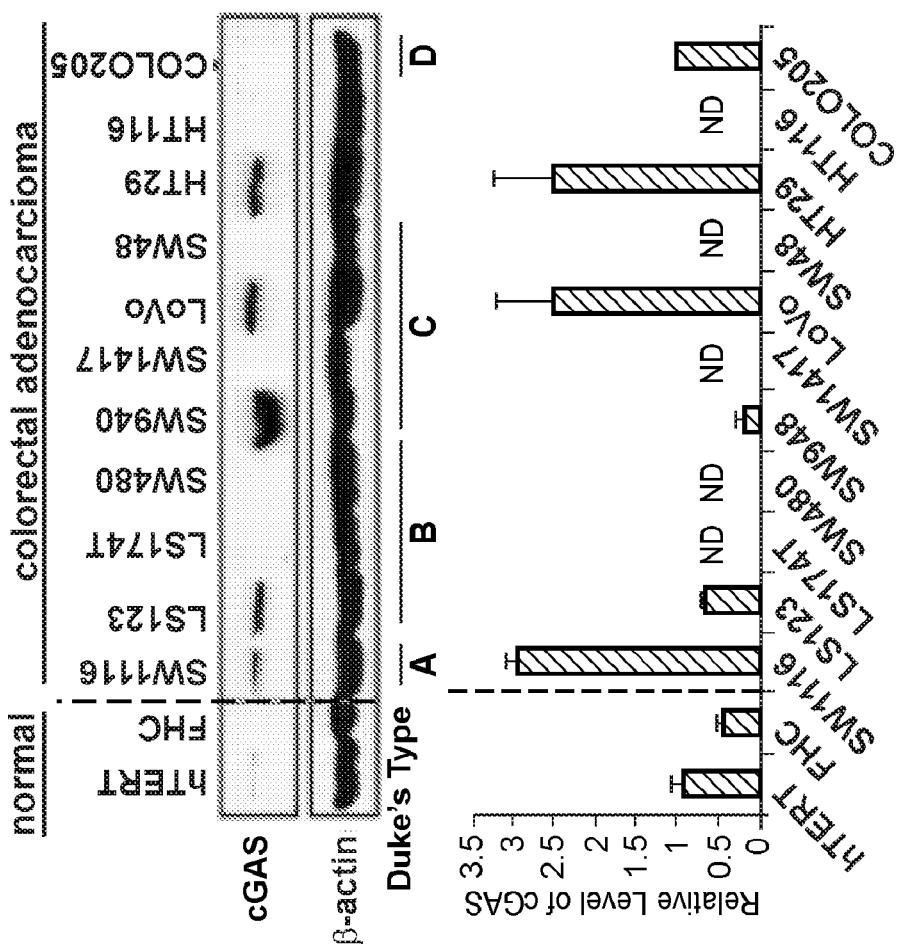
Figure 15C:
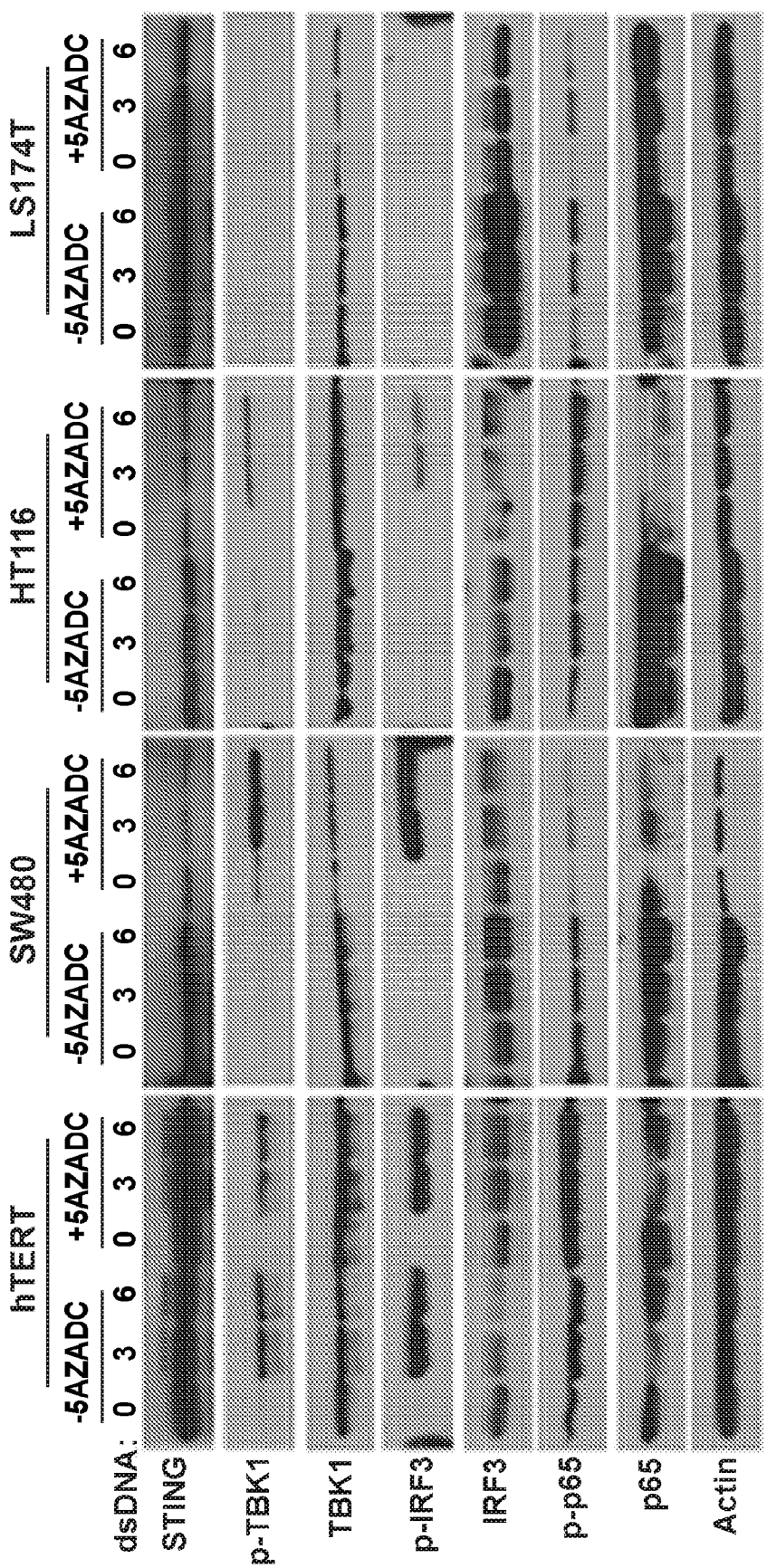
Figure 15D:
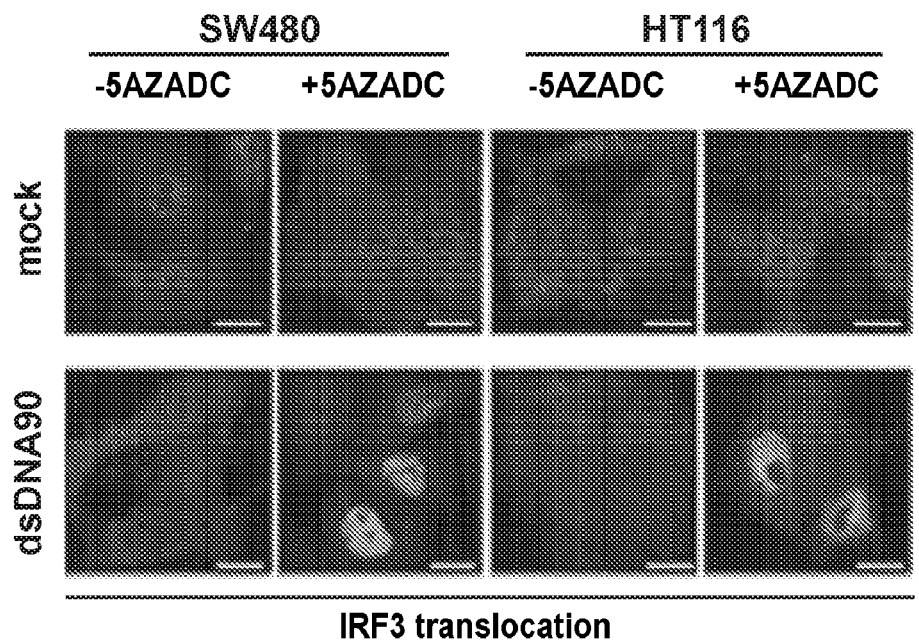
Figure 15E:
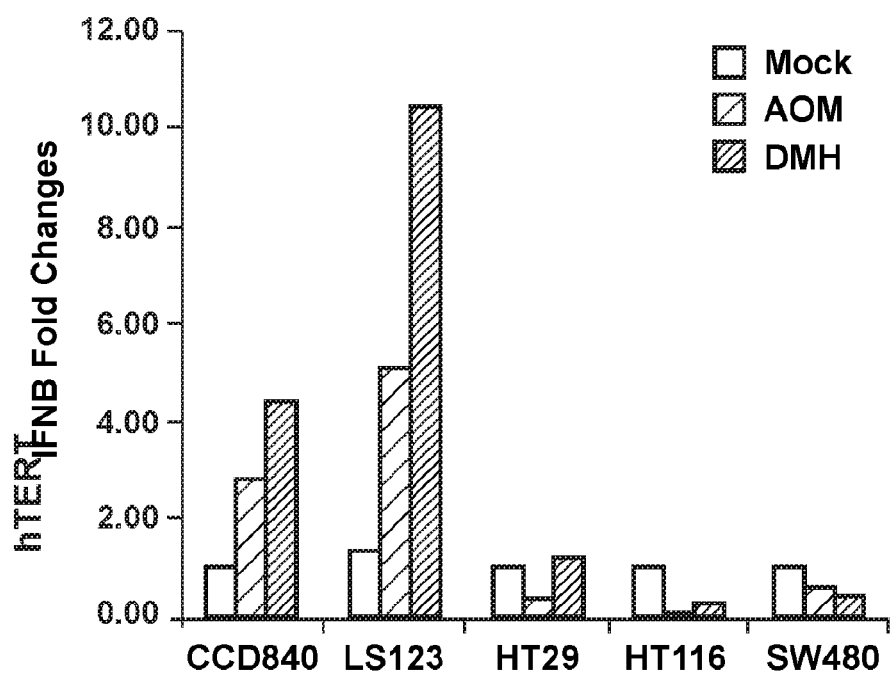
Figure 20A:
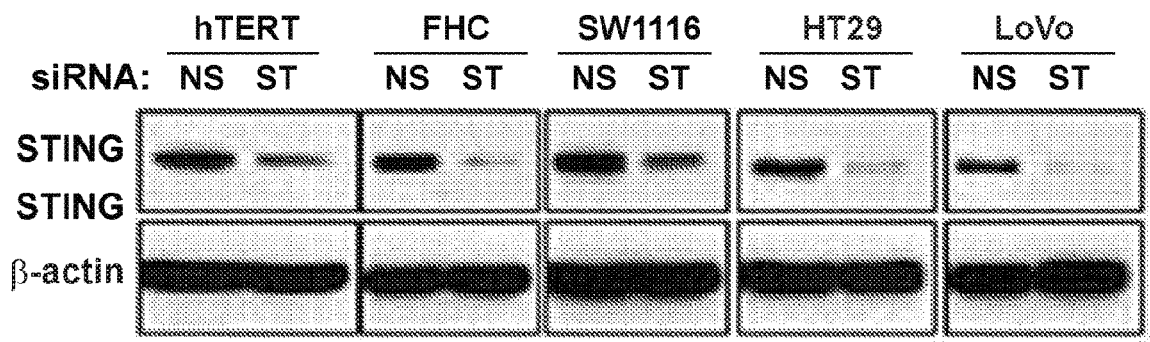
FIGS. 20A-20D show normal and colon cancer cell cells were treated with non-specific siRNA (si-NT) or STING siRNA (si-STING) for 3 days followed by dsDNA90 transfection at 3 µg/ml for 3 hours. Cells were then analyzed for STING siRNA efficiency by immunoblot (FIG. 20A) and by qPCR for IFNB expression (FIG. 20B) and CXCL10 expression (FIG. 20C).
Figure 20B:
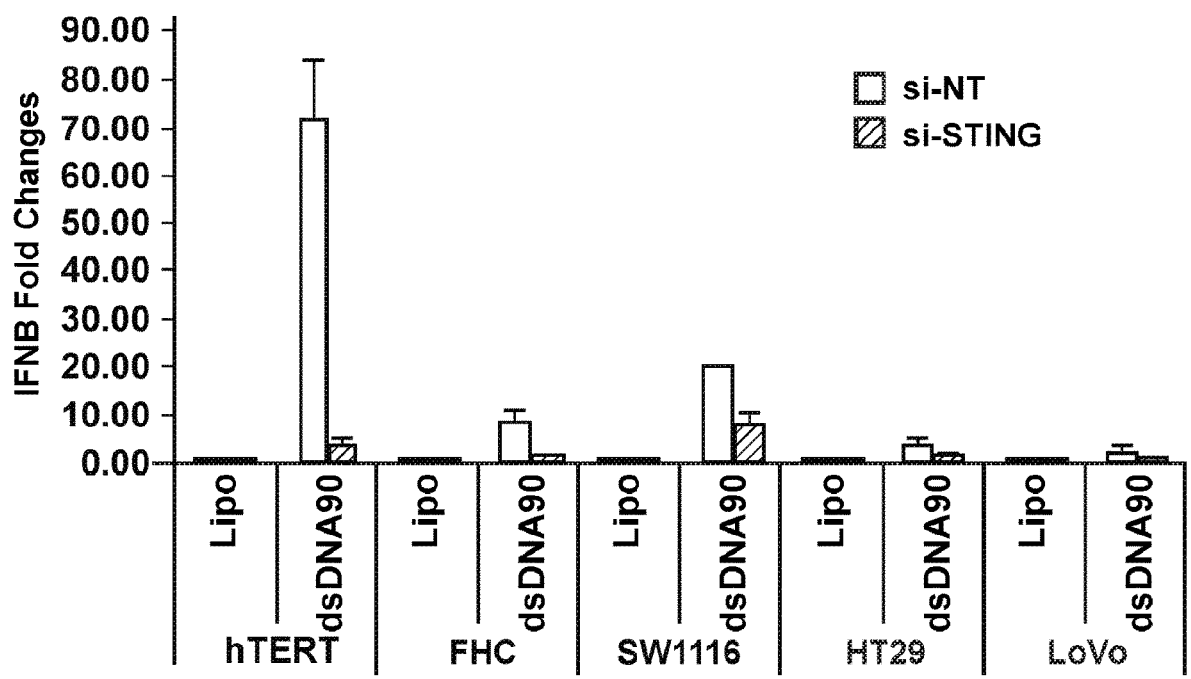
Figure 20C:
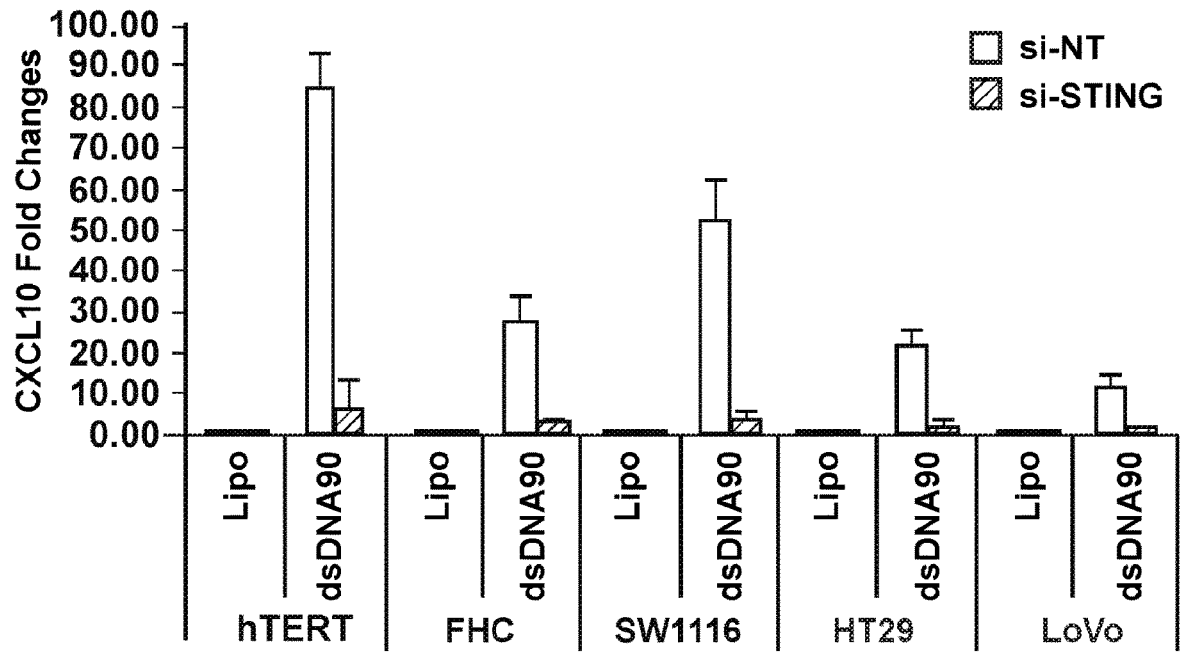
Figure 20D:
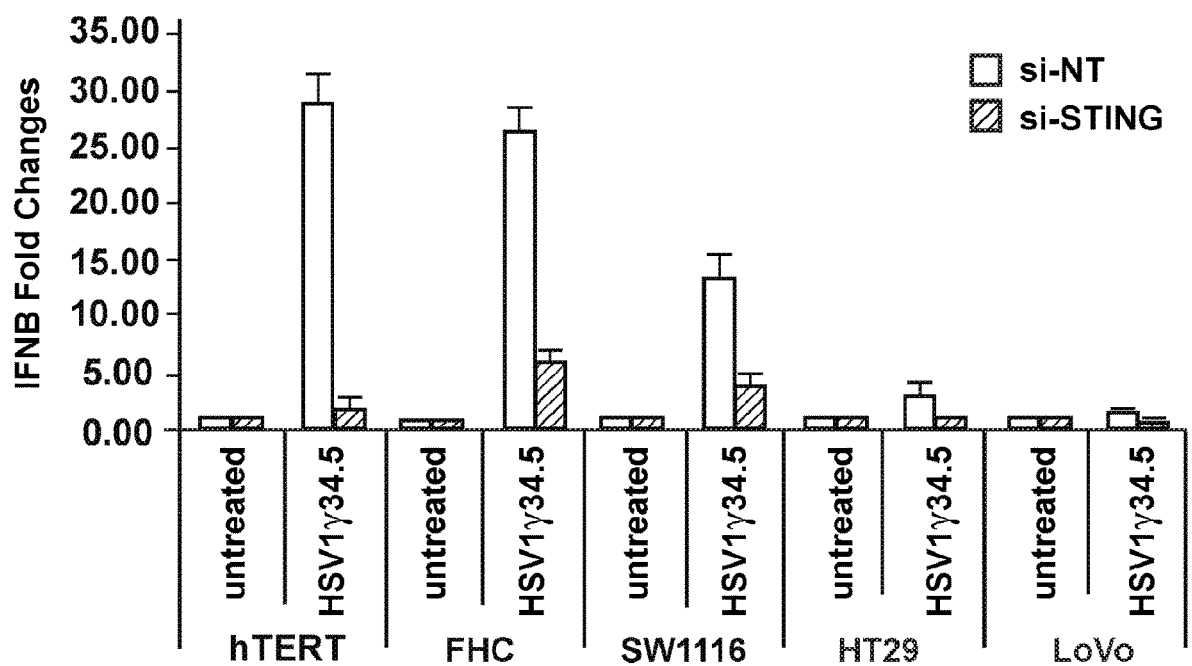
Figure 23A:
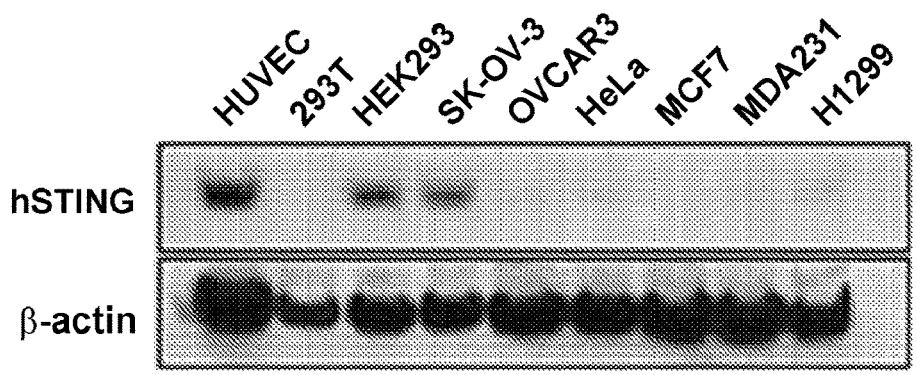
FIGS. 23A-23C show.
Figure 23B:
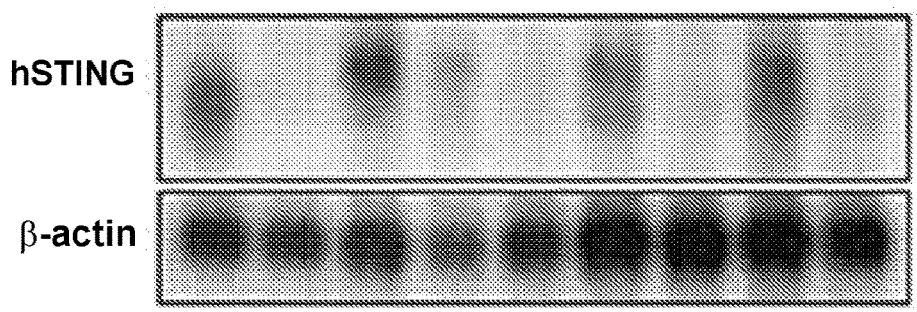
Figure 23C:
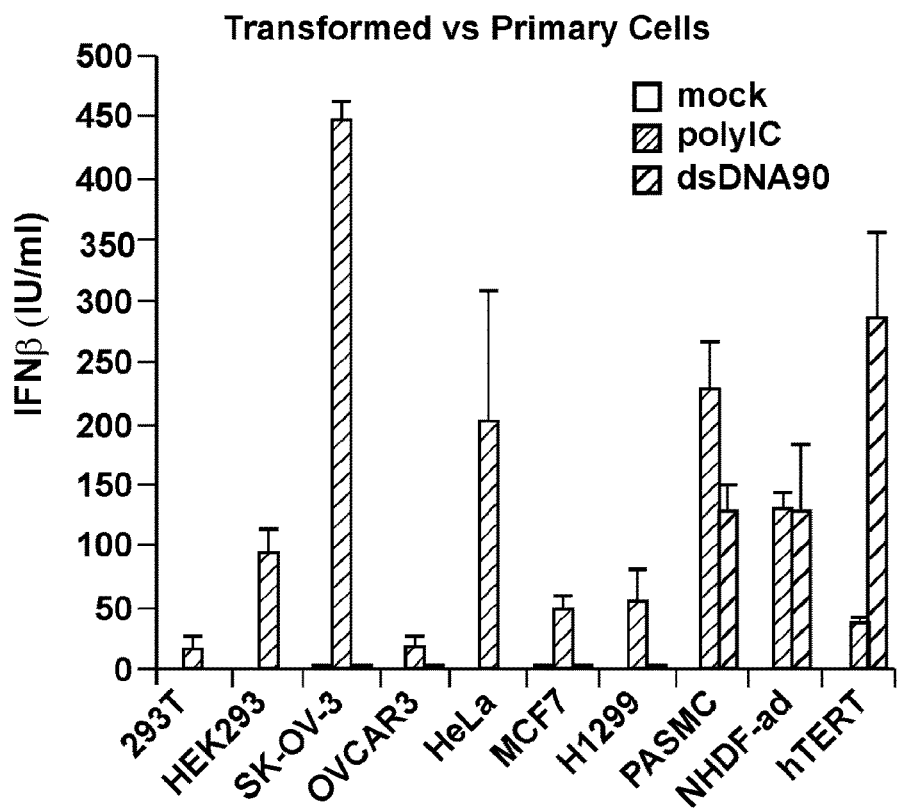

CA Cells Exhibit Defective cGAS Expression:

Loss of STING trafficking in SW480, SW1417, SW48 or HT116 cells could indicate a problem with STING function in the ER, perhaps involving a mutation that would render STING unable to interact with CDNs. Conversely, the breakdown in STING-signaling could occur upstream and involve the synthase cGAS, which generates CDNs following association with dsDNA, to augment STING function. To evaluate this, the entire STING genome within all 11 CA cells was sequenced (introns and exons comprise approximately 7.2 kb on chromosome 5q31.2). Sequence analysis indicated that 2 of the 11 CA cells (LoVo and SW480) exhibited a previously reported HAQ STING variant (Jin et al., 2011; Yi et al., 2013), which occurs in approximately 20% of the population, and which has been reported to be partially defective when overexpressed in 293T cells, yet is able to function normally in the presence of CDNs (FIG. 23). The remainder of the STING genes analyzed represented the R272 encoded product, which has not been reported to exert any defects in function and which represent approximately 85% of the population. Collectively, these findings do not suggest the existence of a major mutation in the STING gene contained within the CA cells and suggest that a defect upstream of STING, for example at the level of cGAS could plausibly be prevalent. We thus started to examine the expression and activity of cGAS in CA cells. An RT-PCR assay was developed and principally measured cGAS mRNA levels. The results indicated that, of the 11 CA cells examined, cGAS expression was absent in 5 (55%) of them (LS174T, SW480, SW1417, SW48 and HT116) (FIG. 13A). This data was confirmed via immunoblot and immunohistochemistry analysis using an antibody to cGAS (FIG. 13A, FIG. 13C). A qPCR examination of 48 human colon adenocarcinoma samples similarly indicated low to undetectable level of cGAS in 15 of 48 samples (31%) (Supplemental FIG. 13B). Our findings could be explained through loss of the cGAS gene. However, sequencing analysis similarly indicated that no major mutations or deletions existed within the genome encoding the cGAS gene (FIG. 24). In view of this, it was examined whether cGAS expression was suppressed by epigenetic phenomena, such as by hypermethylation of the cGAS promoter region (Lao and Grady, 2011; Mitchell et al., 2014). Indeed, databank analysis indicated the presence of considerable CpG islands within the cGAS promoter region (FIG. 20A). Control hTERT, or cGAS-defective LS174T, SW480, SW1417, SW48 or HT116 cells were thus treated with the de-methylating agent 5-Aza-2'-deoxycytidine (5AZADC) for 5 days, and cGAS mRNA levels again evaluated. The study indicated that cGAS expression was rescued in 2 of the 5 cells examined (SW480 and HT116) (FIG. 13B). The sequencing of bisulfite converted genomic DNA retrieved from normal and CA cells confirmed significant hypermethylation within the cGAS promoter region of CA cells where cGAS expression is suppressed (FIG. 20B). It is not yet clear why expression levels of cGAS are muted in the remainder of the CA cells (LS174T, SW1417, SW48) but suppression could speculatively involve other epigenetic modifications such as histone modifications (Jin and Robertson, 2013). Accordingly, treatment of these cells with histone deacetylase or histone-lysine methyltransferases inhibitors partially rescued cGAS mRNA expression in CA cells examined (FIG. 20C). It may also be apparent that alternate mechanisms of cGAS suppression exist, such as those involving miRNAs. To determine if reconstitution of cGAS expression rescued STING-dependent dsDNA signaling, control hTERT or SW480, HT116 (cGAS rescued by 5AZADC) or LS174T (cGAS not rescued by 5AZADC) CA cells were examined. It was observed that the 5AZADC-treated cGAS-rescued SW480, HT116 CA cells, but not LS174T cells regained phosphorylation of TBK1 and IRF3, with concomitant phospho-IRF3 translocation (FIG. 15C, D). These effects were reflected in modest expression of type I IFN and IL-1β in the 5AZADC treated SW480 and HT116 CA cells (FIG. 15E, F). Thus, demethylating agents may be able to partially rescue STING-dependent innate immune gene induction in select CAs.

Figure 21A:
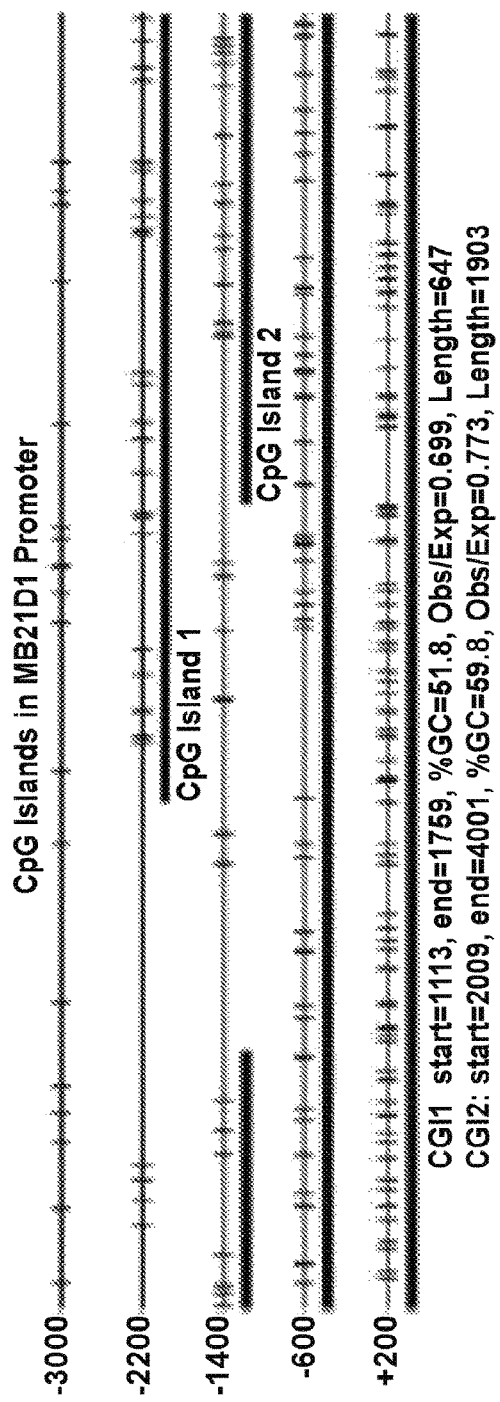
FIGS. 21A-21C show (FIG. 21A), schematic representation of CpG islands located in the proximal promoter regions of cGAS.
Figure 21B:
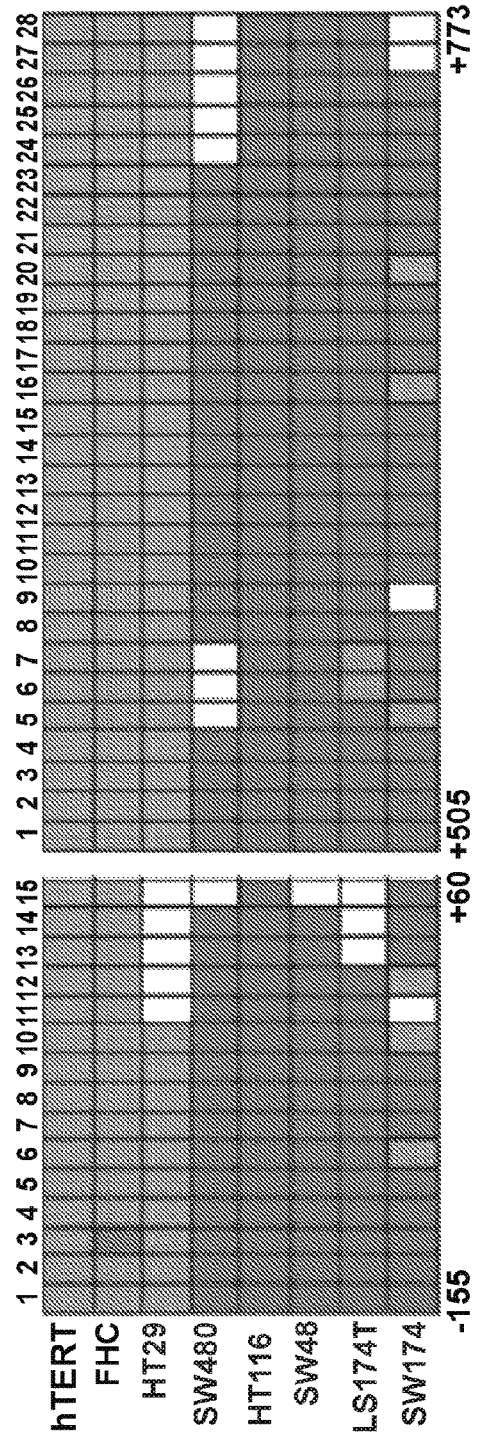
Figure 21C:
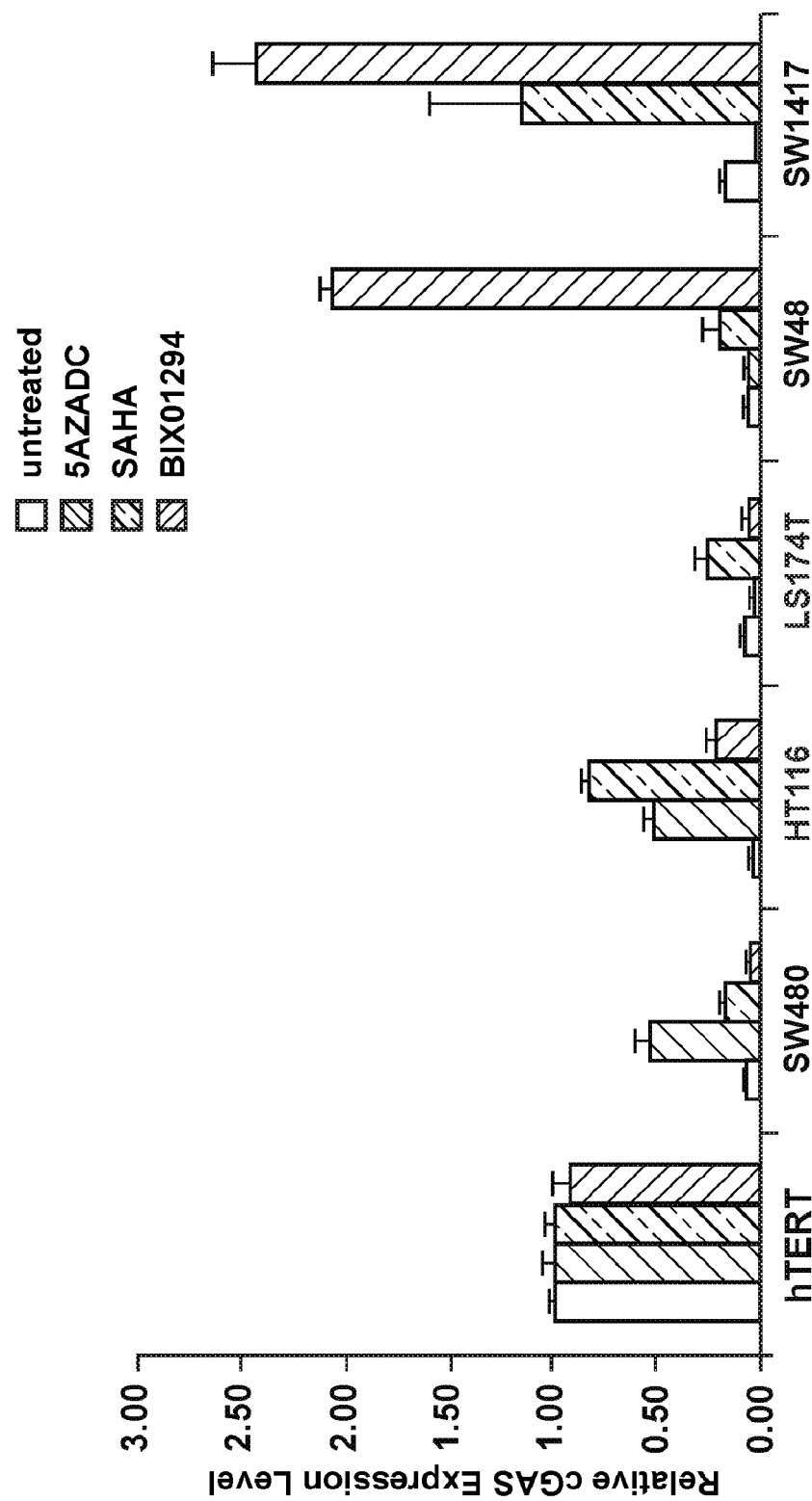
Figure 22:
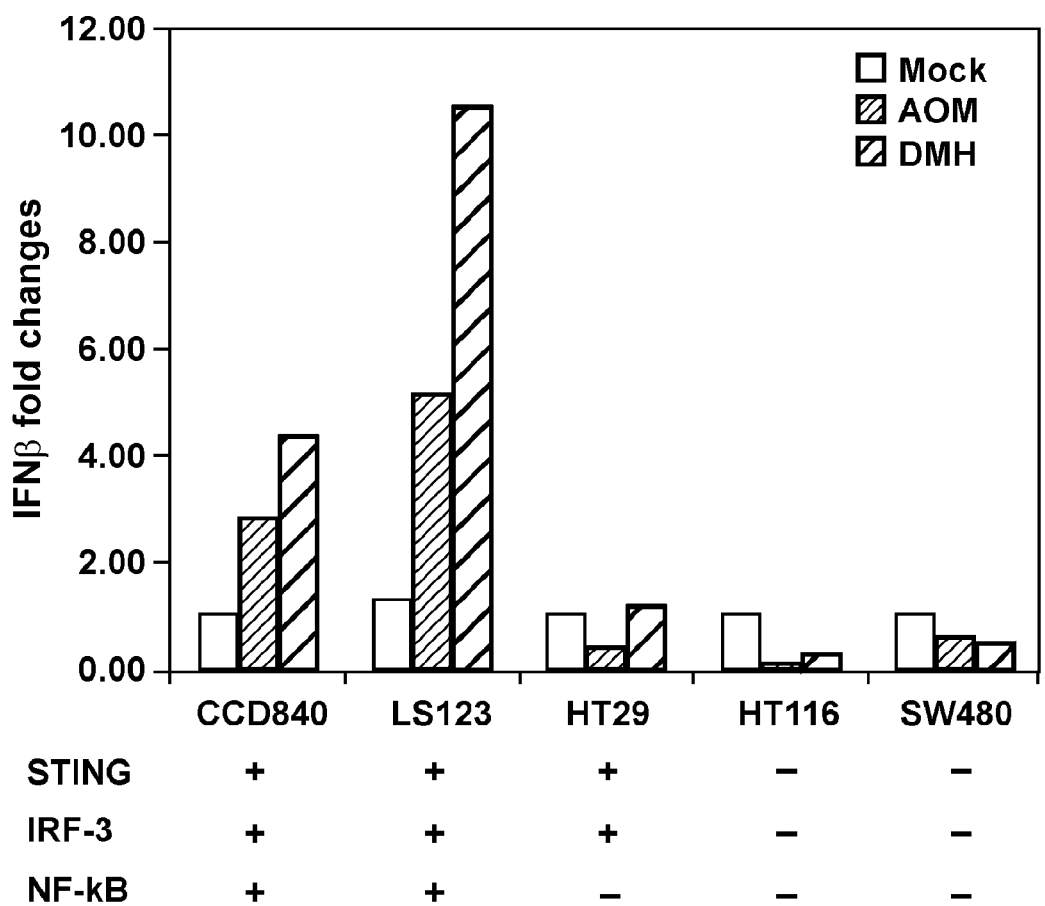
FIG. 22. Normal and colon cancer cells were treated with AOM or DMH at 15 mM for 20 hours. IFNB induction was analyzed by qPCR. STING, IRF3 and NF-kB translocation was examined; +, translocation; −, no translocation.

The question arises as to why the STING-signaling pathway may be inhibited in colon adenocarcinoma. Recently, it was shown that STING-deficient cells and mice are sensitive to AOM-induced DNA damage. In this situation, the STING pathway may play a role in the DNA-damage response pathway, to induce the production of cytokines which facilitate tissue repair or damaged cell removal (Chatzinikolaou et al., 2014; Kidane et al., 2014; Lord and Ashworth, 2012). As such, innate immune induction of CA cells in response to DNA damaging agents was examined. As shown in FIG. 21, the carcinogens AOM and DMH were able to induce the production of type I IFN in normal colon epithelial (CCD841) and in LS123 (which exhibited partial STING activity; FIGS. 4C and 4D). However, CA cells which exhibited defective STING activated IRF3 or NF-kB activity were unable to generate type I IFN in response to AOM or DMH. Thus, the inhibition of the STING pathway may enable DNA damaged cells, harboring mutations, to escape part of the DNA damage response and the immune surveillance machinery to progress into a tumorigenic state.

Figure 16A:
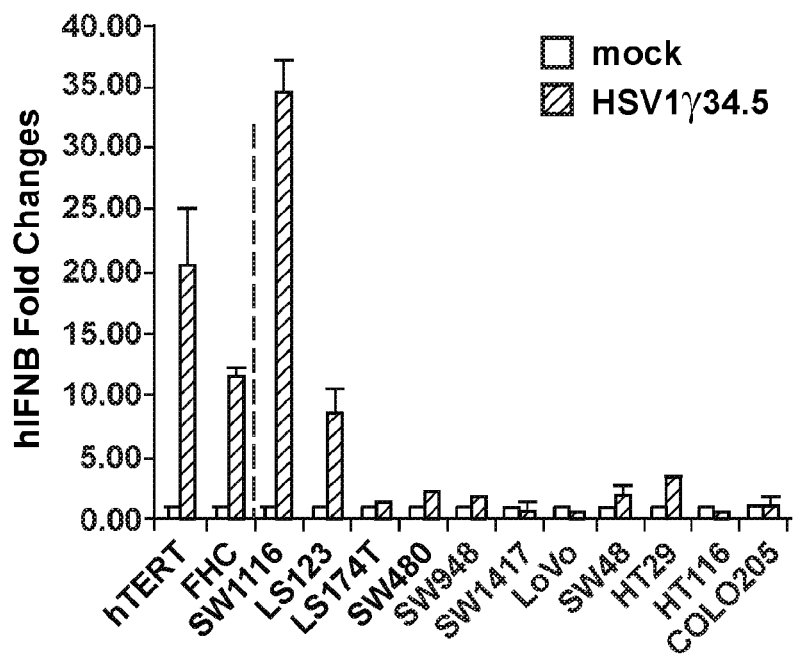
Figure 16B:
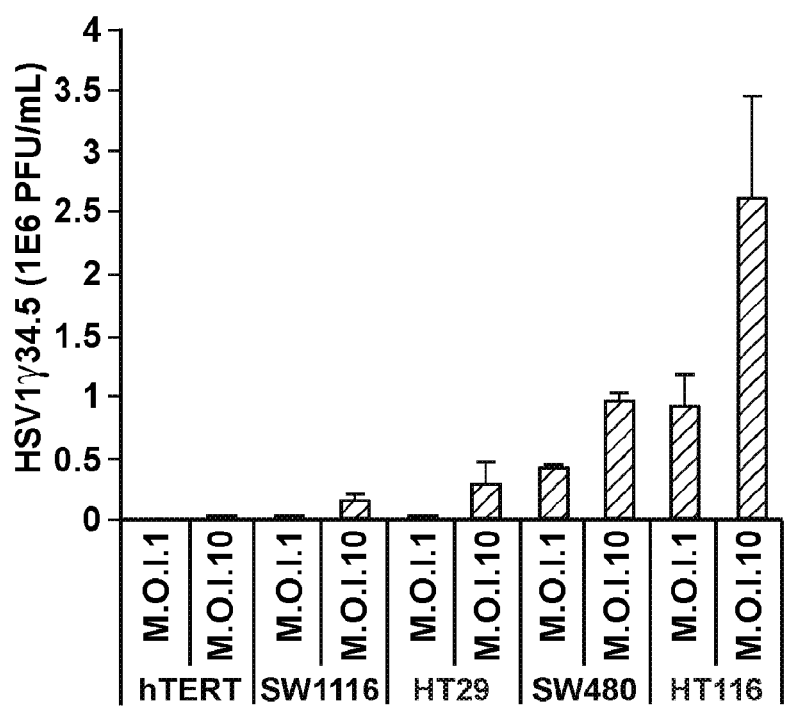

Tumors with Defective STING-Signaling are Sensitive to Viral Oncolysis:

The inventors have previously shown that loss of STING signaling in vitro or in vivo renders cells or mice, respectively, extremely sensitive to Herpes simplex virus (HSV) infection. HSV, containing a dsDNA genome of 375 kb is presently being evaluated in clinical trials as a therapeutic agent for the treatment of cancer (Kolodkin-Gal et al., 2009). However, the mechanisms of oncolysis remain to be fully determined and there is no evaluation, presently, for determining the efficacy of HSV antitumor treatment. Given that it has been previously shown that STING signaling plays a critical role in host defense responses to HSV infection, and that STING activity is defective in numerous CA cells, it was postulated that the ability of STING to signal may affect outcome to HSV therapy. To start to address this CA cells or control hTERT and FHC were infected with HSV1 lacking the λ34.5 encoding product that is presently being evaluated as an oncolytic agent, including against colon cancer as well as melanoma. The λ34.5 viral protein has been proposed to suppress host defense responses, although the mechanisms remain to be fully clarified. Thus, HSV1λ34.5 does not robustly repress innate immune signaling events and potently triggers STING-dependent innate immune gene induction, including type I IFNs. This analysis indicated that similar to our dsDNA transfection results, HSV1λ34.5 induced the production of IFNβ mRNA significantly in control hTERT and FHC cells, as well as SW1116 and LS123 CA cells (FIG. 16A). However, little type I IFN was induced in the remainder of the CA cells, including SW480 and HT116, deficient in cGAS expression. The ability to induce type I IFN inversely correlated with HSV1λ34.5 replication, due to the induced anti-viral effects (FIG. 16B). Furthermore, cells such as SW480 and HT116 underwent rapid cell death, likely due to robust viral replication, while control cells and cells with partial STING function (SW1116 and HT29) were significantly more refractory (FIG. 15C). The experiments were followed up by infecting CA cells with HSV expressing the luciferase gene that contained λ34.5 (HSV-Luc). This data confirmed that CA cells exhibiting defective STING-signaling such as SW480 and HT116 enabled more viral-induced luciferase expression (FIG. 16D). siRNA treatment further confirmed that the IFNβ responses induced by HSV1λ34.5 in normal and STING functional CA cells are STING dependent (FIG. 19D). Of note is that HSV1 is not the only DNA virus to be considered as an oncolytic therapeutic agent to treat cancer. Other candidate viruses under consideration, including as a therapeutic against colon cancer, comprise Vaccinia Virus (VV), a dsDNA virus with 190 kb genome that replicates in the cytoplasm of infected cells. To evaluate whether VV can trigger host innate immune response in the absence of functional STING signaling, we infected CA cells with partial STING signaling capacity (SW116 and HT29) or completely defective STING signaling (SW480, HT116) with VV. Similar to the situation using HSV1λ34.5, VV triggered type I IFN and CXCL10 production only in the control cells or CA cells with partial STING signaling ability and not in cells with loss of STING function (SW480 and HT116) (FIG. 16E, F). The data herein indicates that CA cells with defective STING-signaling are highly susceptible to HSV1 and VV oncolytic activity. Thus, it is plausible that being able to measure the presence or absence of STING/cGAS expression may help predict the response of patients with certain cancers to viral oncolytic therapy.

Predicting Outcome to Viral Oncolytic Therapy.

The present data indicates that the outcome of oncolytic virotherapy involving DNA-based viruses such as HSV1 may be predicted by the presence or absence of STING/cGAS expression. Since the STING pathway naturally requires the presence of STING and cGAS to function, and since it has been observed that STING and/or cGAS may be absent in 30-55% of colon cancer, being able to measure the presence of these two gene products may therefore indicate the effectiveness of DNA-viral oncotherapy. This could be achieved using RT-PCR methodology but biopsied tissue may contain infiltrating hematopoietic cells that contain normal STING/cGAS expression. Thus, analysis of STING and/or cGAS protein or RNA expression within the cancer cell itself would provide more accurate information into the status of STING function. Since an effective antibody to detect cGAS protein was not identified, a RNA in situ hybridization assay was designed using RNAscope technology that can detect the single levels copies of an mRNA within individual cells. By labeling the STING probe green (FITC), and the cGAS probe red (Cy5), both probes were detectable in the same assay and the mRNA levels of STING and cGAS within the identical cell could be effectively quantitated. To test the assay, control cells or cGAS positive (SW1116 or HT29) or negative (SW480 and HT116) CA cells were incubated with RNA probes recognizing cGAS (red) or STING (green) mRNA. This study indicated that STING and cGAS expression could be detected and quantitated in the control (hTERT and FHC) and STING/cGAS positive (SW1116 or HT29) CA cells using the RNAscope (FIG. 17A, C). However, only STING was observed in the cGAS negative (SW480 and HT116) CA cells (FIG. 17A, C). STING was not detectable in SW48 cells, as expected, using this assay (FIGS. 5A and 17A, C). This data also correlated with our previous expression analysis of cGAS in these cells by RT-PCR (FIG. 13A). Moreover, cGAS expression was observed by RNAscope in those CA cells where cGAS mRNA production was rescued following treatment with 5AZADC (SW480 and HT116); FIG. 17B, D). Thus, fluorescence in situ hybridization analysis may be able to predict the outcome to oncolytic viral therapy depending on the presence or absence of cGAS or STING.

Figures 17F, 17G:
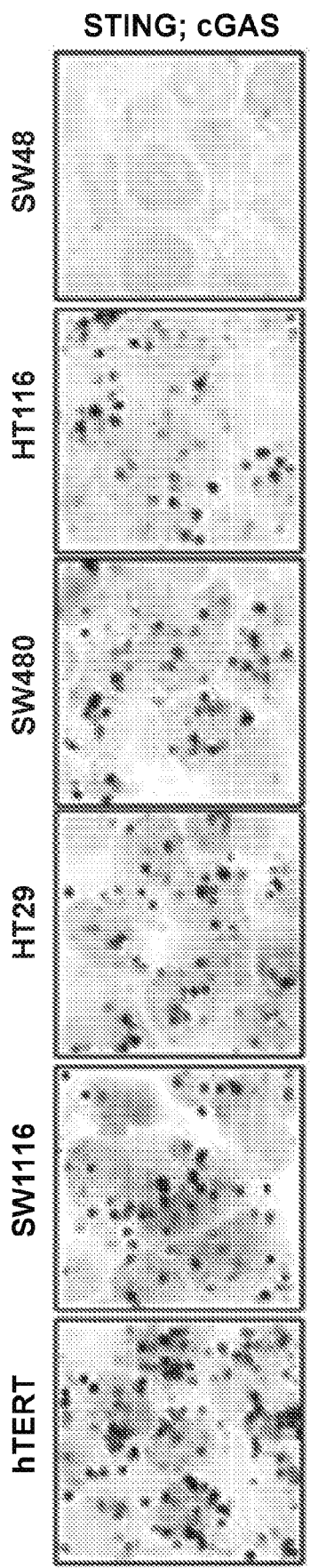
Figure 17H:
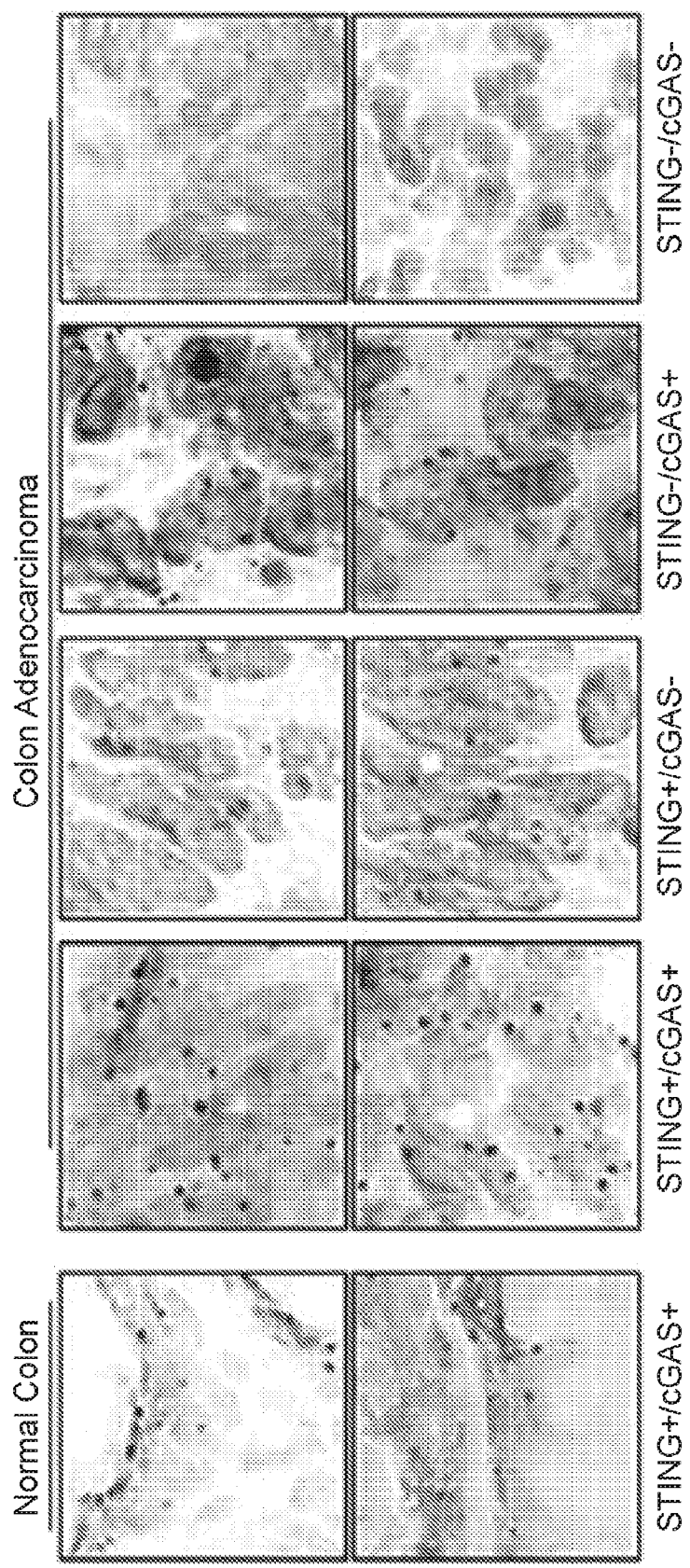

To further follow up on this assay, normal hTERT, or cGAS positive (SW1116 or HT29) or negative (SW480 and HT116) CA cells were paraffin embedded, as well as SW48 which had both cGAS and STING expression missing. This situation may mimic situations where biopsied and paraffin embedded patient derived material required analysis. The experiment was again readily able to detect using the RNA probes both STING and cGAS expression in control, SW1116 and HT29 cells, as before, and only STING in the cGAS negative SW480 and HT116 CA cells (FIG. 17E, F). Neither cGAS nor STING was observed in the double negative SW48 line (FIGS. 4A and 17E, F). This assay was further tested on 12 normal and 80 CA samples in paraffin embedded tissue microarray (TMA) and it was observed that STING was lost in 14% of CA samples and cGAS 15% of CA samples. Both STING and cGAS were lost in 9% of CA samples (FIG. 17G, H). However, it was noted that STING expression and/or function was absent in a variety of other tumors, indicating that suppression of this pathway may be widespread in human cancer (FIG. 23). Thus, RNAscope analysis of STING/cGAS duel expression from paraffin embedded tissue may help predict the outcome of select viral oncolytic therapy in vivo, as determined next.

In Vivo Analysis of CA Cells with Defective STING Signaling to HSV1λ34.5 Therapy.

To correlate the in vitro oncolytic effect of HSV1 λ34.5 in vivo, nude mice were subcutaneously inoculated with CA cells harboring partial (SW1116 or HT29) or defective (SW480 and HT116) STING signaling. HSV1λ34.5 was then administered intratumorally (FIG. 18A). It was observed that tumors exhibiting partial STING-signaling (SW1116 and HT29) were refractory to viral oncolytic treatment (FIG. 18B, C). However, tumors derived from CA cells with defective STING-signaling were noted to be extremely susceptible to virus treatment (FIG. 18D, E). This data indicates that the activity of the STING pathway may predict the outcome of HSV-related oncolytic therapy against colon as well as other cancers.

Discussion

The STING controlled signaling pathway is essential for facilitating innate immune gene transcription in response to the recognition of cytosolic DNA species. STING activity can be triggered by CDNs such as cyclic-di-AMP or cyclicdi-GMP produced from intracellular bacteria such as *Listeria monocytogenes* or by cyclic-di-GMP-AMP (cGAMP) manufactured by the synthase cGAS following association with cytosolic dsDNA species (Sun et al., 2013; Woodward et al., 2010). Such DNA can represent the genome of DNA pathogens, such as HSV-1 or bacteria such as *Mycobacterium tuberculosis*, as well as self DNA leaked from the nucleus of DNA damaged cells. STING-deficient mice, while viable, are extremely sensitive to lethal infection by a variety of pathogens. However, chronic STING activity has been shown to cause a diversity of autoinflammatory disease, through the overproduction of pro-inflammatory cytokines. Indeed, inappropriate overstimulation of STING has even been shown to aggravate inflammation driven skin cancer (Ahn et al., 2014). However, transient STING activity has been shown to be essential for mediating the generation of anti-tumor T-cell responses. Data suggests that STING, in professional antigen presenting cells (CD8+ dendritic cells) becomes extrinsically activated by the DNA of engulfed dying tumor cells which results in the triggering of cytokines such as type I IFN, which facilitates cross-presentation and CTL priming. Correspondingly, the therapeutic administration of CDNs, intratumorally, has been shown to repress tumor growth, presumably by facilitating DC-dependent CTL production (Corrales et al., 2015; Woo et al., 2014). STING may also play a role in influencing the anti-tumor effects of checkpoint inhibitors such as PD1, although the mechanisms remain to be determined.

The inventors have also recently demonstrated that STING-deficient mice are susceptible to carcinogen-aggravated CAC (Ahn et al., 2015). In this situation, evidence indicates that damaged DNA can trigger STING intrinsic activity, perhaps by leaking out of the nucleus or through other mechanisms that remain to be clarified. Presumably, this event would augment cytokine production that would attract the immune system to the damaged cell(s). Eradication of such cells may ensue, as well as the stimulation of cytokine and growth factor dependent tissue repair. Data suggests that STING can trigger the production of cytokines that facilitate wound repair in the gut, such as IL-1β. Such cytokines are processed by nucleotide-binding oligomerization-domain protein like receptors (NLRs) such as NLRP3 and NLRP6, which interact with inflammasome-associated ASC and caspase-1 to process IL-1β and IL-18. These pro-inflammatory cytokines are secreted and bind to receptors mainly requiring MyD88 for signaling. IL-18 production can suppress IL-22BP, which is responsible for inhibiting the wound repair activity of IL-22. Loss of ASC, caspase-I, MyD88 or IL22BP can increase tumorigenesis in colitis-associated colon cancer models, similar to loss of STING (Elinav et al., 2011; Huber et al., 2012; Salcedo et al., 2010). STING may thus work in concert with inflammasome processing.

Thus, loss of STING suppresses tissue healing and damaged mucosal lining may enable the infiltration and expansion of bacteria with enhanced genotoxic ability which would aggravate STING-independent inflammatory responses. The generation of ROS by overactive, infiltrating immune cells may enhance DNA damaging processes and facilitate mutational inactivation of TSGs or the mutational activation of growth stimulatory proteins such as k-ras. Thus, intrinsic STING-signaling may play a key role in preventing the development of cancer through responding to DNA damage and alerting the immune surveillance machinery. In addition, extrinsic STING activity in DCs is also required for the generation of anti-tumor CTLs. This places STING in a pivotal role in the host anti-cancer defense arsenal.

Given this, the expression and regulation of STING signaling in colon cancer was analyzed and found frequent suppression of STING activity. These events inhibited the production of DNA-damage dependent cytokine production, which may enable the damaged cell to escape the attention of the immune surveillance system. Such cells may evade eradication and further genetic mutation events may accrue to enhance the tumorigenic process. The inhibition of STING signaling was observed to mainly involve the suppression of STING expression, or of the synthase cGAS. Significant mutation or deletion events involving the STING or cGAS genes were not observed, but rather observed frequent transcriptional suppression involving hypermethylation of the promoter regions. Cytosolic DNA signaling was partially rescued using demethylating agents which regained cGAS expression in some but not other CA cells. However, it remains unclear whether the rescue of STING signaling in cancer cells may afford better responses to anti-cancer agents. Further, that cGAS and in some cases STING expression was not rescued by demethylating agents may indicate other forms of epigenetic silencing that requires additional characterization. In other CA types, it was observed that the ability of STING to activate the transcription factors NF-κB or IRF3 was impaired, by molecular mechanisms that also remain to be determined. It is noteworthy that a number of other genes involved in DNA repair, such as the mismatch repair proteins MHS2 and MLH1 are also reported to be frequently silenced in colon cancer (Chatzinikolaou et al., 2014; Lord and Ashworth, 2012). Thus, targeting the DNA repair machinery maybe a common requirement in cancer development. Collectively, it was observed that STING-dependent signaling was defective in approximately 80% or more of colon related tumors examined. This may indicate that suppression of STING function is also a key obligation for the tumorigenic process.

Since loss of STING may be common in tumors and may even predict outcome to anti-cancer therapy, the inventors developed assays to evaluate the expression levels of both STING and cGAS. Loss of either of these two proteins appears to repress cytosolic DNA mediated innate immune signaling. The present ability to measure STING and cGAS mRNA expression in situ, and STING protein expression using antibody enabled us to develop a screen that indicated loss of one or other of these proteins in over 40% of CAC. Such assays may be useful in predicting the effective response rates of cancers to select therapeutic interventions. Further, recapitulating STING signaling in tumors, via novel antitumor gene therapy approaches, might enable such cells to reactivate host antitumor immunity.

Accordingly, it was noticed that loss of STING signaling in CA cells enabled the robust replication of DNA-based viruses such as HSV1. Viruses, such as HSV1 and vaccinia virus, are presently being used as oncolytic agents for the treatment of cancer. Such viruses may directly destroy the tumor cell by lysis as well as create a tumor antigen source for engulfment by APCs for the generation of CTLs. Data indicates that STING plays a key role in both these processes. However, the efficacy of successful oncoviral therapy remains low, for reasons that remain unclear. Mainly, assays based on molecular insight, that may help predict treatment outcome have not been developed. This is because the molecular mechanisms that explain oncolysis in cancer cells rather than normal cells remains to be fully appraised. Evidence suggests that innate immune signaling pathways that exert anti-viral activity may be defective in cancer cells. Our data presented here is amongst the first clear indication that loss of an innate signaling pathway can predict the outcome to oncoviral therapy. Thus, utilization of molecular biomarker assays similar to the ones portrayed here may enable a more predictive response to the use of microbes for the treatment of cancer. Such assays may also shed insight into whether other STING-dependent anti-tumor therapies based on CDNs, or even DNA-adduct based chemotherapeutic regimes, may work or not (Mansour, 2014; Rowe and Cen, 2014). In this light, we have recently described that the immunological benefits of using chemotherapeutic agents such as cisplatin and etoposide significantly involved the STING-signaling pathway. Thus, further studies on the regulation and function of STING in cancer may provide acumen into the molecular mechanisms of tumorigenesis as well as provide a therapeutic target that may help in the treatment of cancer.

Experimental Procedures

Materials.

All reagents were from Invitrogen, ThermoScientific or Sigma unless specified.

Cell Culture.

Normal human cell and human cancer cell lines were purchased from Lozna and ATCC respectively and cultured in their appropriate growth media according to the instructions. Media and supplements are from Invitrogen. hTERT-BJ1 Telomerase Fibroblasts (hTERT) were originally purchased from Clontech and were cultured in 4:1 ratio of DMEM:Medium 199 supplement with 10% FBS, 4 mM L-Glutamine and 1 mM sodium pyruvate at 37° C. in a 5% CO2-humidified atmosphere.

Immunoblot Analysis.

Equal amounts of proteins were resolved on sodium dodecyl sulfate (SDS)-Polyacrylamide gels and then transferred to polyvinylidene fluoride (PVDF) membranes (Millipore). After blocking with 5% Blocking Reagent, membranes were incubated with various primary antibodies (and appropriate secondary antibodies). The image was resolved using an enhanced chemiluminescence system ECL (Thermo Scientific) and detected by autoradiography (Kodak). Antibodies: rabbit polyclonal antibody against STING was developed in our laboratory as described previously in Ishikawa et al, 2008; other antibodies were obtained from following sources: β-actin (Sigma Aldrich), p-IRF3 (Cell Signaling), IRF3 (Santa Cruz Biotechnology), p-p65 (Cell Signaling), p65 (Cell Signaling), p-TBK1 (Cell Signaling), TBK1 (Abcam), cGAS (Cell Signaling).

Interferon β ELISA Analysis.

Interferon β Elisa was performed using either the IFNβ human ELISA Kit from Invitrogen or the Human IFNβ ELISA Kit from PBL InterferonSource following the manufacturer's protocol.

Immunofluorescence Microscopy.

Cells were cultured and treated in their appropriate media on Lab-Tek II chamber slides. Cell were fixed with 4% paraformaldehyde for 15 minutes in at 37° C. and permeabilized with 0.05% Triton X-100 for 5 minutes at room temperature. Immunostaining was performed with rabbit-anti-STING polyclonal, rabbit-anti-IRF3 (Santa Cruz Biotechnology) or rabbit-anti-p65 (Cell Signaling) followed by fluorescence conjugated secondary antibodies (FITC-goat-anti-rabbit) (Invitrogen). Images were taken with Leika LSM confocal microscope at the Image Core Facility, University of Miami.

Microarray Analysis.

Total RNA was isolated from cells or tissues with RNeasy Mini kit (Qiagen). RNA quality was analyzed by Bionalyzer RNA 6000 Nano (Agilent Technologies). Gene array analysis was examined by Illumina Sentrix BeadChip Array (Human HT-12_V4_Bead Chip) at the Oncogenomics Core Facility, University of Miami. Gene expression profiles were processed and statistical analysis was performed at the Bioinformatics Core Facility, University of Miami. Briefly, raw intensity values from Illumina array are uploaded on GeneSpring™ software from Agilent. Values are Quantile normalized and log 2 transformed to the median of all samples. Significantly differential expressed genes from a two-class comparison are computed using the Student's t-test and selected using threshold of P-value≤0.05. Hierarchical Clustering and visualization of selected differentially expressed genes is performed on GeneSpring using Pearson Correlation distance method and linkage was computed using the Ward method. Fold Change analysis was performed between two groups and differentially expressed genes were selected based on threshold of Fold Changes.

Quantitative Real-Time PCR (qPCR).

Total RNA was reverse transcribed using QuantiTect Reverse Transcription Kit (Qiagen). Real-time PCR was performed with the TaqMan gene Expression Assay (Applied Biosystems).

Immunohistochemistry and Histological Analysis.

Tissue Microarray was purchased from Origene. Immunohistochemistry staining was performed with rabbit-anti-cGAS antibody following standard protocol.

HSV1γ34.5 Amplification, Purification, Titration and Infection.

HSV1γ34.5 was amplified in Vero cells and purified by sucrose gradient ultracentrifugation following standard protocol. Plague assay using serial diluted virus was performed in Vero cells following standard protocol. Cells were infected with HSV1γ34.5 at specific M.O.I. for 1 hours, washed and then incubated for designated period for specific assay examination.

RNA In Situ Hybridization.

STING and cGAS RNA probed was custom designed by ACD and RNA in situ Hybridization was performed using RNAscope® Multiplex Fluorescent Reagent Kit for cultured cells and 2-plex RNAscope® Reagent Kit for FFPE cells and tissue following the manufacturer's instruction.

Mouse Treatment.

Balb/C nu/nu mice were purchased from Charles River. Tumor cells were introduced in the flanks of Balb/c nude mice by subcutaneous injection of 2E106 of the appropriate tumor cells and tumors allowed to develop to an average diameter of approximately 0.5 cm. HSV1γ34.5 was then be injected into the tumors every other day for a total of three times at appropriate dosage (i.e. 50 µl at 1E7). PBS was used as vehicle control. Effects on tumor growth was monitored. Mice were euthanized when tumor diameter exceeds 10 mm.

Bisulfite Sequencing Analysis.

Bisulfite conversion of genomic DNA was performed using EZDNA Methylation Kit from Zymo Research followed by PCR amplification. PCR products were then gel purified and sequenced.

Statistical Analysis.

All statistical analysis was performed by Student's t test unless specified. The data were considered to be significantly different when P<0.05.

Example 3

STING Function in Melanoma

Given the findings above, the studies were extended into evaluating STING function in melanoma, in part because such cancers appear to be susceptible to viral oncolytic treatment, which suggests defects in innate immune pathways. Here it is reported that STING mediated innate immune signaling is largely impaired both in human melanoma derived cells and in primary patient melanoma-derived tissues. Loss of STING and/or cGAS expression in melanoma was recurrently found, predominantly through epigenetic hypermethylation silencing. These findings suggest that suppression of STING signaling may be an important part of tumor development. Moreover, loss of STING function rendered melanoma cells more susceptible to HSV1 and vaccinia virus-mediated oncolysis. Therefore, the development of a prognostic assay that enables the measurement of STING or cGAS expression may lead to a better indication of the efficacy of viral oncolytic treatment.

Recurrent Loss of STING Signaling in Human Melanoma Derived Cell Lines.

Figure 26A:
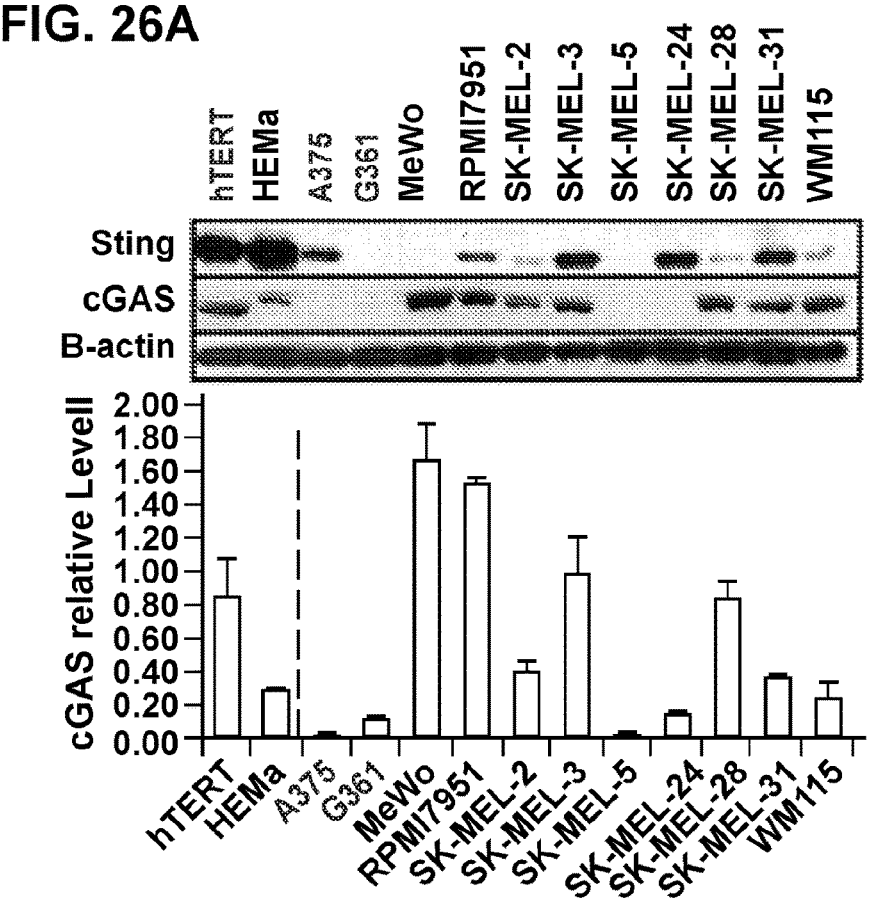
FIGS. 26A-26D show STING expression is suppressed and dsDNA induced innate immune activation is impaired in majority of human melanoma cell lines.
Figure 26B:
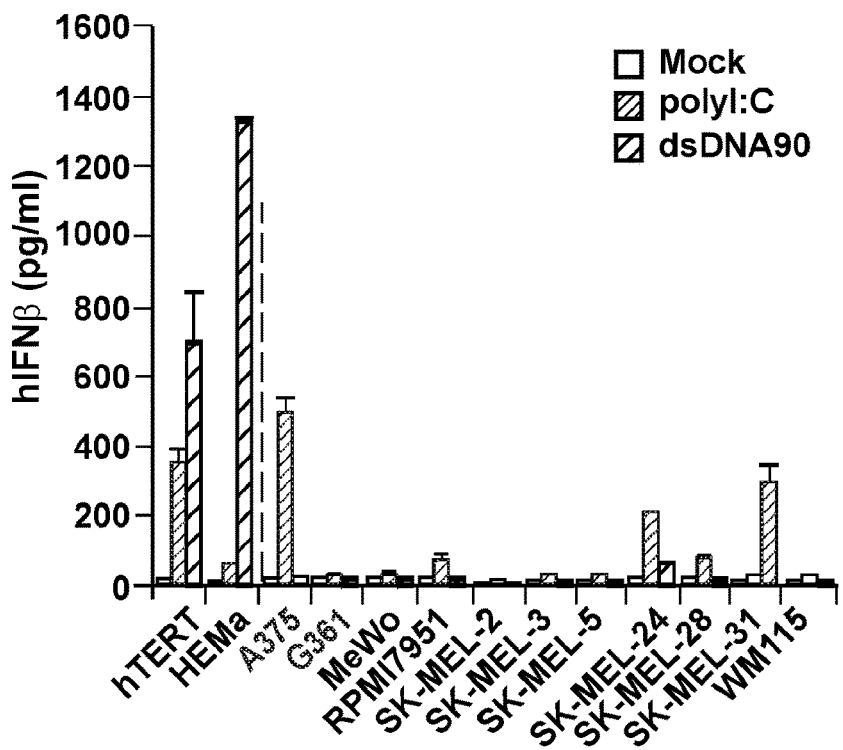
Figure 26C:
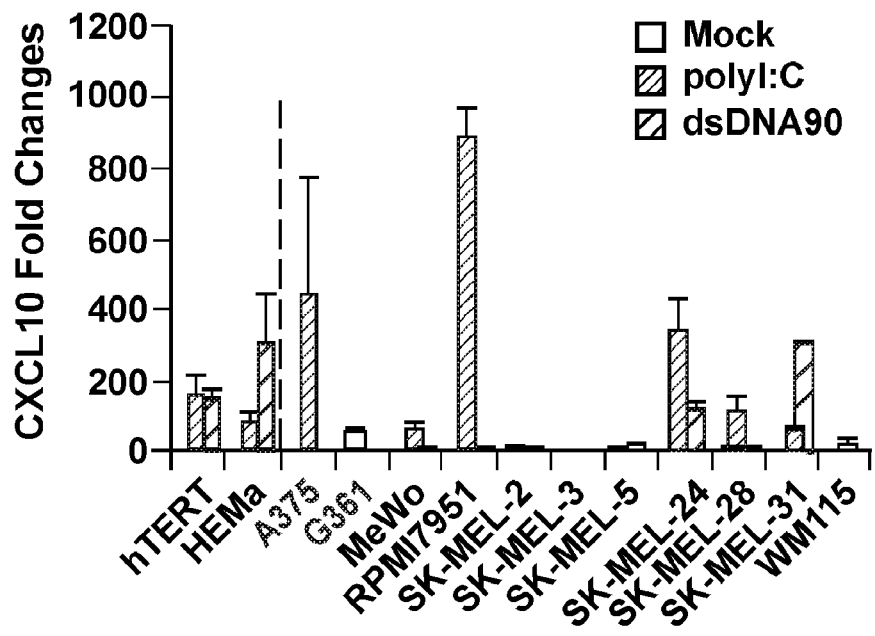
Figure 26D:
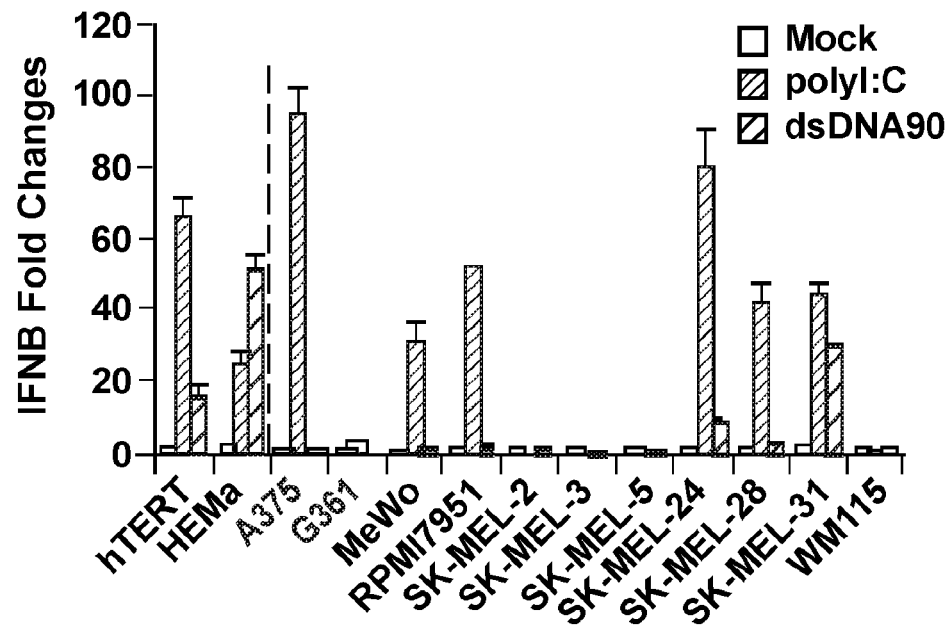

The STING-controlled innate immune pathway has been reported to be largely impaired in human colon cancers, an event which may facilitate tumorigenesis (Xia T, Konno H, Ahn J, Barber G N. Deregulation of STING Signaling in Colorectal Carcinoma Constrains DNA Damage Responses and Correlates With Tumorigenesis. Cell reports. 2016; 14:282-97). To evaluate whether this key pathway is similarly defective in other types of cancer STING expression was further examined by immunoblot in a panel of human malignant melanomas. These results showed that STING expression was not detectable in 3 out of 11 cell lines examined (G361, MeWo and SK-MEL-5) and STING expression level was dramatically suppressed in a further 3 cell lines (SK-MEL-2, SK-MEL-28 and WM115) (FIG. 26A). The synthase cGAS resides upstream of STING and generates CDN's capable of triggering STING function. Next, the expression of cGAS by immunoblot was examined and it was found that this synthase was absent in 4 out of 11 cell lines examined (A375, G361, SK-MEL-5 and SK-MEL-24) (FIG. 26A). Real-time PCR analysis using cGAS probe confirmed that cGAS was not detectable in A375 and SK-MEL-5, but low level of cGAS was detected in G361 and SK-MEL-24 (FIG. 26A). To correlate STING/cGAS expression analysis with functional STING signaling, cells were transfected with dsDNA to activate STING-dependent cytokine production, or with dsRNA (polyI:C) to activate the STING-independent RIG-I like signaling pathway and measured type I IFN expression by ELISA (Ishikawa et al., 2008). This study indicated that all 11 melanoma cells responded poorly to STING-dependent, dsDNA-triggered type I IFN production. Using fluorescence microscopy analysis, it was confirmed that all cells were indeed transfected with FITC-labeled dsDNA activator. However, control hTERT cells and normal human melanocytes (HEMa) were able to express high levels of IFNβ when transfected with dsDNA, suggesting the STING mediated type I interferon responses were suppressed specifically in the melanoma cells (FIG. 26B). This finding was further supported by real-time PCR analysis, in which dsDNA stimulated IFNB and CXCL10 induction was suppressed in majority of the melanoma cells examined, although weak activity were detected in SK-MEL-24 and SK-MEL-31 cells (FIG. 26C-D). In contrast, 6 of the 11 Melanoma cells were able to produce type I IFN and CXCL10, albeit at various levels, in response to dsRNA, indicating that the RIG-I-Like RNA signal pathway were mostly intact in majority of melanoma cells examined (FIG. 26C-D). Using siRNA treatment to knock down STING expression in normal cells and 2 melanomas cell-lines (SK-MEL-24, SK-MEL31) that appeared to retain partial STING activity, it was confirmed that the upregulation of these dsDNA-induced cytokines was STING-dependent. Taken together, our data indicates that STING-dependent signaling is largely impaired in a majority of melanoma cells with only SK-MEL-24 and SK-MEL-31 exhibiting weak STING activity.

Loss of STING Dependent TBK1-IRF3 Activation in Melanoma Cells.

Figure 27D:
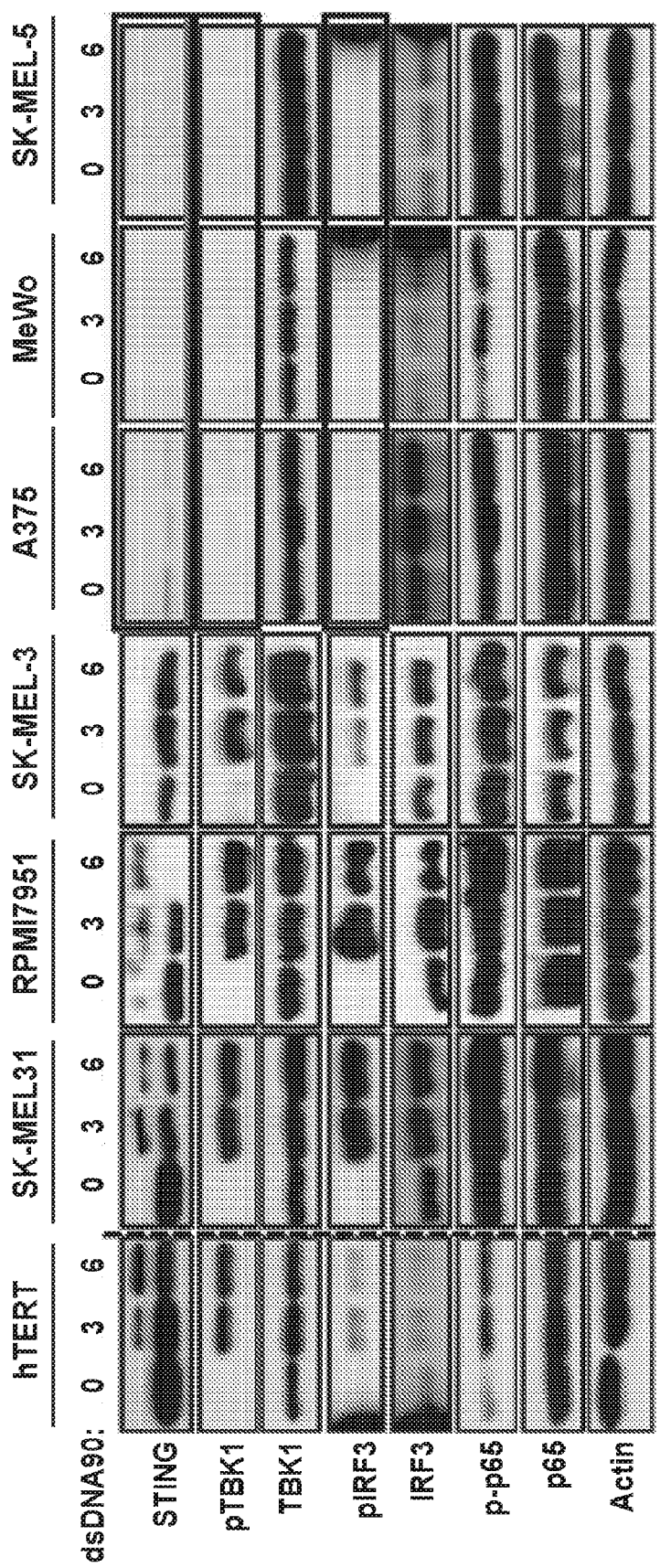

To examine the extent of STING signaling defect in melanoma cells, IRF3 and NF-κB activation were evaluated by immunofluorescence microscopy and immunoblot analysis. When stimulated with dsDNA, STING rapidly undergoes translocation from the ER, along with TBK1, to perinuclear-associated endosomal regions, containing NF-kB and IRF3, in a procedure similar to autophagy (Ishikawa et al., 2008, Konno et al., 2013). This incident accompanies STING phosphorylation and degradation, almost certainly to avoid prolonged STING-induced cytokine production which is now known to provoke chronic inflammation (Ahn et al., 2014). Our results confirmed that, following dsDNA treatment in normal hTERT cells, STING translocated to perinuclear region and underwent phosphorylation and degradation events, (FIGS. 27A and 27D, left panel). During this process, TBK1 was phosphorylated in hTERT cells as well as its cognate target IRF3 and the p65 subunit of NF-κB (FIG. 27D). IRF3 and p65 translocation into the nucleus was also observed, indicating normal activation (FIGS. 27B, C and D). A similar effect was observed in SK-MEL-24 and SK-MEL-31 cells which exhibited partial dsDNA-dependent cytokine production, confirming that these two cell lines retained some STING function (FIGS. 27A-D and FIGS. 26B-D). However, while RPMI7951 and SK-MEL-3 retained STING/cGAS expression and displayed similar IRF3 activation upon dsDNA treatment, these cells lacked p65 translocation. This observation would explain why dsDNA failed to trigger type I IFN production, which requires both IRF3 and NF-kB for its transcriptional activation (FIGS. 27A-D and FIGS. 26B-D). In addition, in cells where STING and/or cGAS expression were not detected (such as A375, G361, MeWo and SK-MEL-5), no evidence of TBK1 or IRF3 phosphorylation/translocation was detected in these cells following dsDNA treatment (highlighted by boxes) (FIGS. 27B, D). Although phosphorylated p65 was observed, no translocation of this transcription factor into the nucleus was evident in any of the RPMI7951, SK-MEL-3, A375, G361, MeWo or SK-MEL-5 cells (FIGS. 27C-D). These results indicate that dsDNA induced STING signaling is deregulated at various points along the pathway in many of the melanoma cell lines examined. For example, while STING retained some signaling activity and ability to induce the translocation of IRF3, as in RPMI7951 and SK-MEL-3 cells, NF-kB signaling was observed to be affected. In contrast, STING did not appear to undergo any phosphorylation or translocation in A375, G361, MeWo or SK-MEL-5 cells, suggesting that STING function is affected upstream of IRF3/NF-kB activation, likely due to loss of STING and/or cGAS expression.

RNAscope and IHC Analysis of STING/cGAS Expression.

Figure 28A:
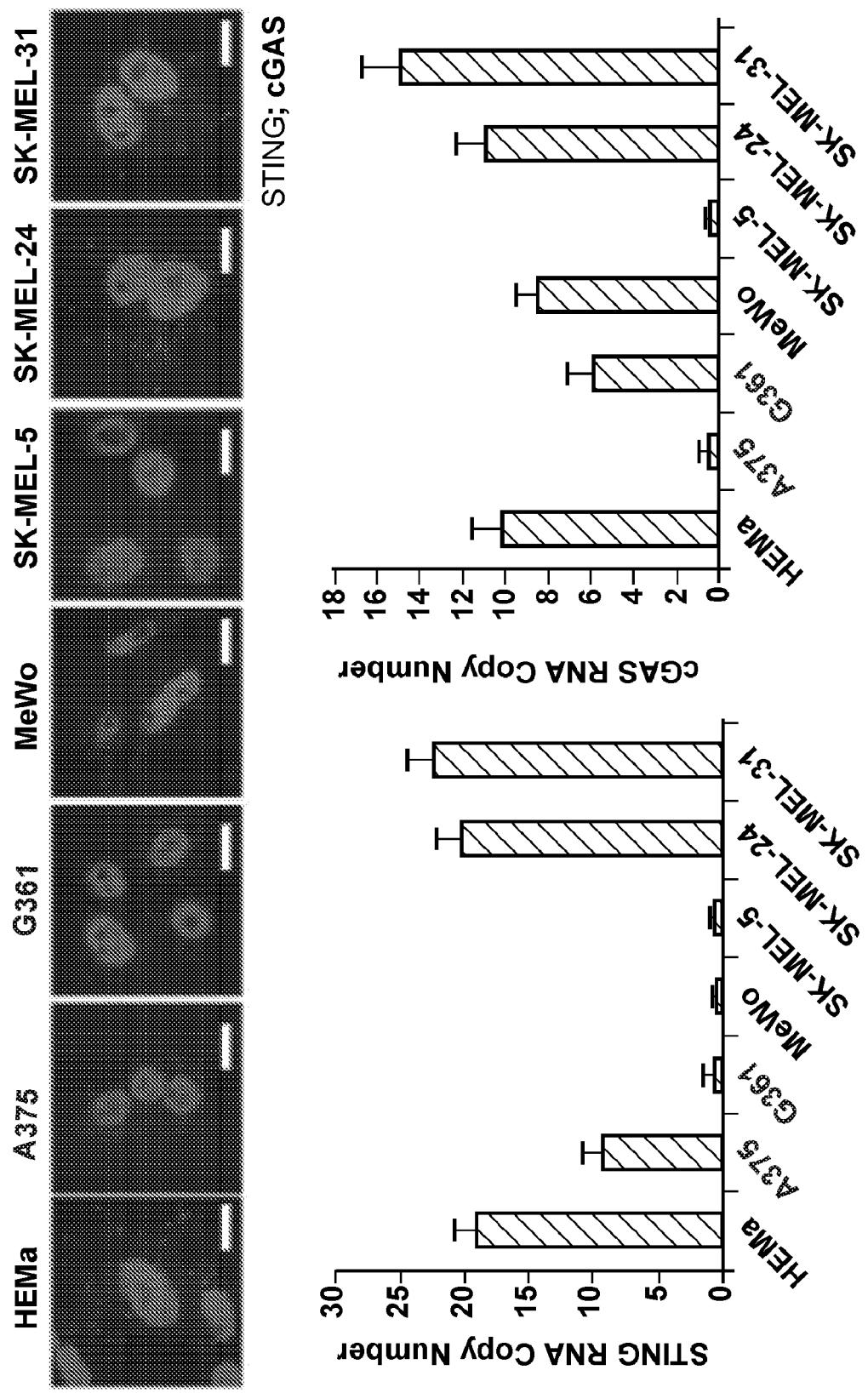
FIGS. 28A-28C show RNA in situ hybridization and immunohistochemistry analysis of STING and cGAS in human melanoma cell lines.
Figure 28B:
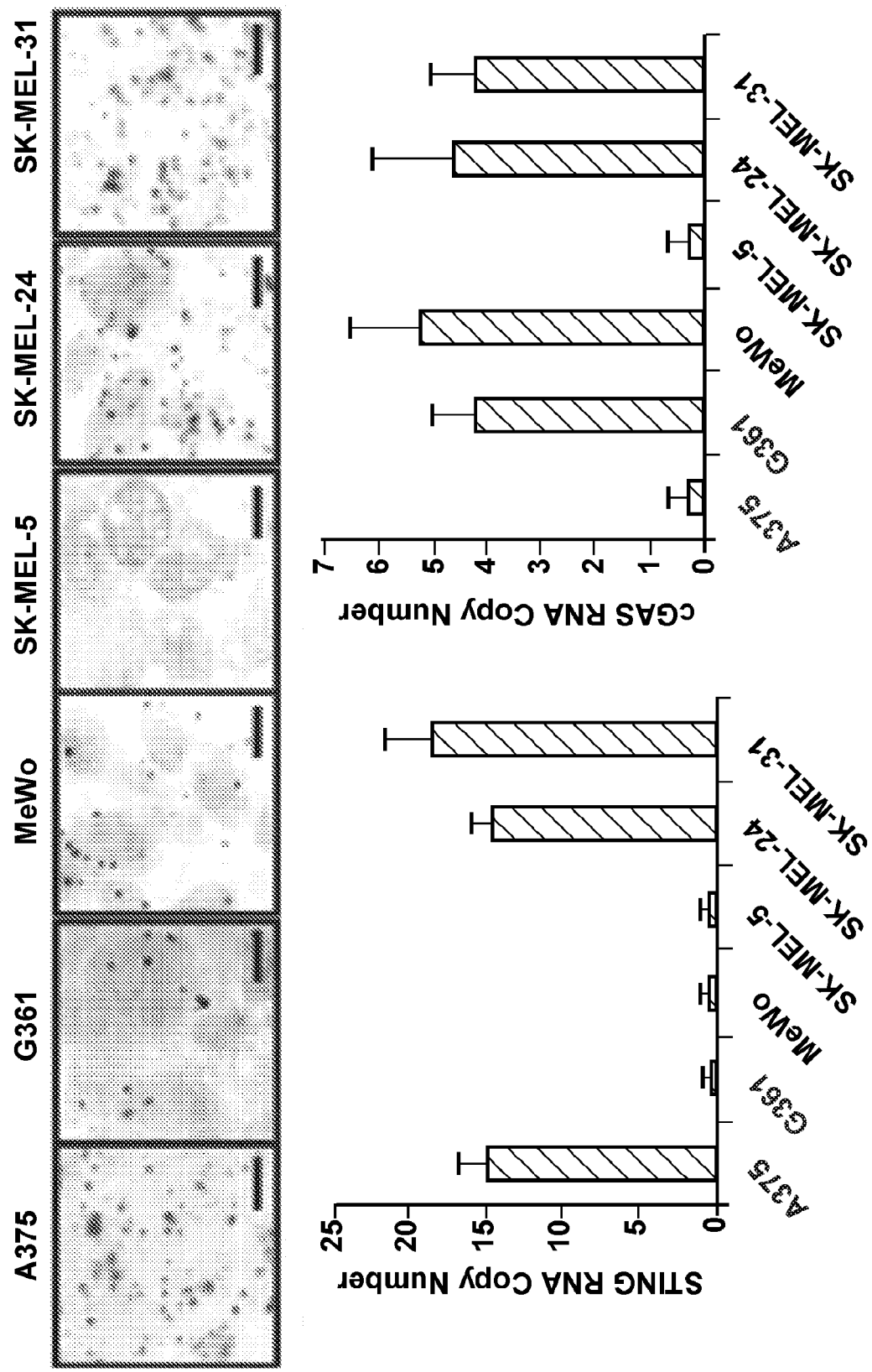

Since the STING pathway requires the presence of STING and cGAS, and since STING and/or cGAS expression was observed to be absent in ~40% melanoma cells examined, being able to measure the presence of STING and cGAS could be useful in predicting functional STING signaling in melanoma. Although immunoblot and RT-PCR methodology is effective in examining STING/cGAS expression in cultured cell lines, biopsied tissue often contains not only tumor cells but also other cell types including infiltrating immune cells that could retain normal STING/cGAS expression (Ishikawa et al., 2009). Thus, analysis of STING and/or cGAS protein or RNA expression within the cancer cell itself is necessary for accurate evaluation into the presence of these products. As described above, an RNA in situ hybridization assay using RNAscope technology that can efficiently detect STING/cGAS mRNA copies within individual cells. By using FITC-labelled STING probe (green), and Cy5-labelled cGAS probe (red), melanoma cells were examined using RNA fluorescent in situ hybridization (RNA FISH). Results showed that both probes combined within the same assay effectively detected STING and cGAS mRNA in control HEMa cells. STING mRNA was also detected in A375, SK-MEL-24 and SK-MEL-31 cells but not in G361, MeWo or SK-MEL-5 cells whereas cGAS mRNA was not detected in A375 or SK-MEL-5 cells (FIG. 28A). mRNA copy numbers were quantitated with results being consistent with our previous results obtained using our expression analysis (FIG. 26A, 28A). Thus, RNA fluorescence in situ hybridization analysis can effectively quantitate STING/cGAS expression simultaneously in single cells.

mRNA expression by chromogenic in situ hybridization (RNA CISH) of paraffin embedded melanoma cells was also evaluated. This situation may mimic situations where biopsied and paraffin embedded patient derived material are generally used for biomarker analysis. This study was able to detect and quantitate both STING and cGAS mRNA expression in SK-MEL-24 and SK-MEL-31 cells as before. In A375 cells, only STING was detected whereas cGAS was absent. STING was not detected in G361 or MeWo cells. Both STING and cGAS were absent in SK-MEL-5 cells (FIG. 28B). Overall RNA CISH analysis generated similar results to RNA FISH evaluation.

Figure 28C:
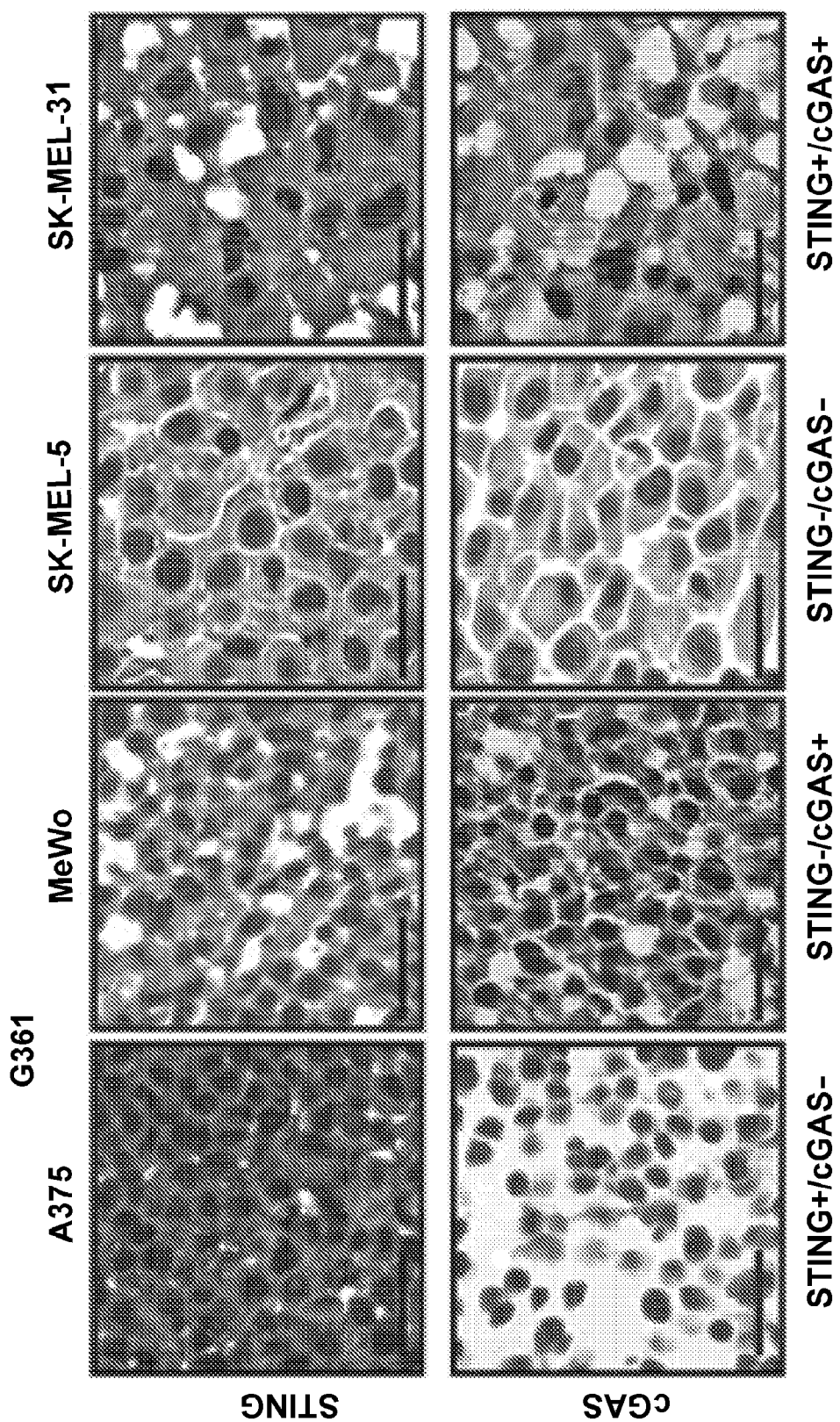

Using antibody to cGAS and STING, immunohistochemistry (IHC) analysis on paraffin embedded cells was also performed, which confirmed cGAS and STING protein expression status in accord with our immunoblot and RNAscope studies (FIG. 28C).

IHC Analysis of STING/cGAS Expression in Melanoma TMA.

Figure 29:
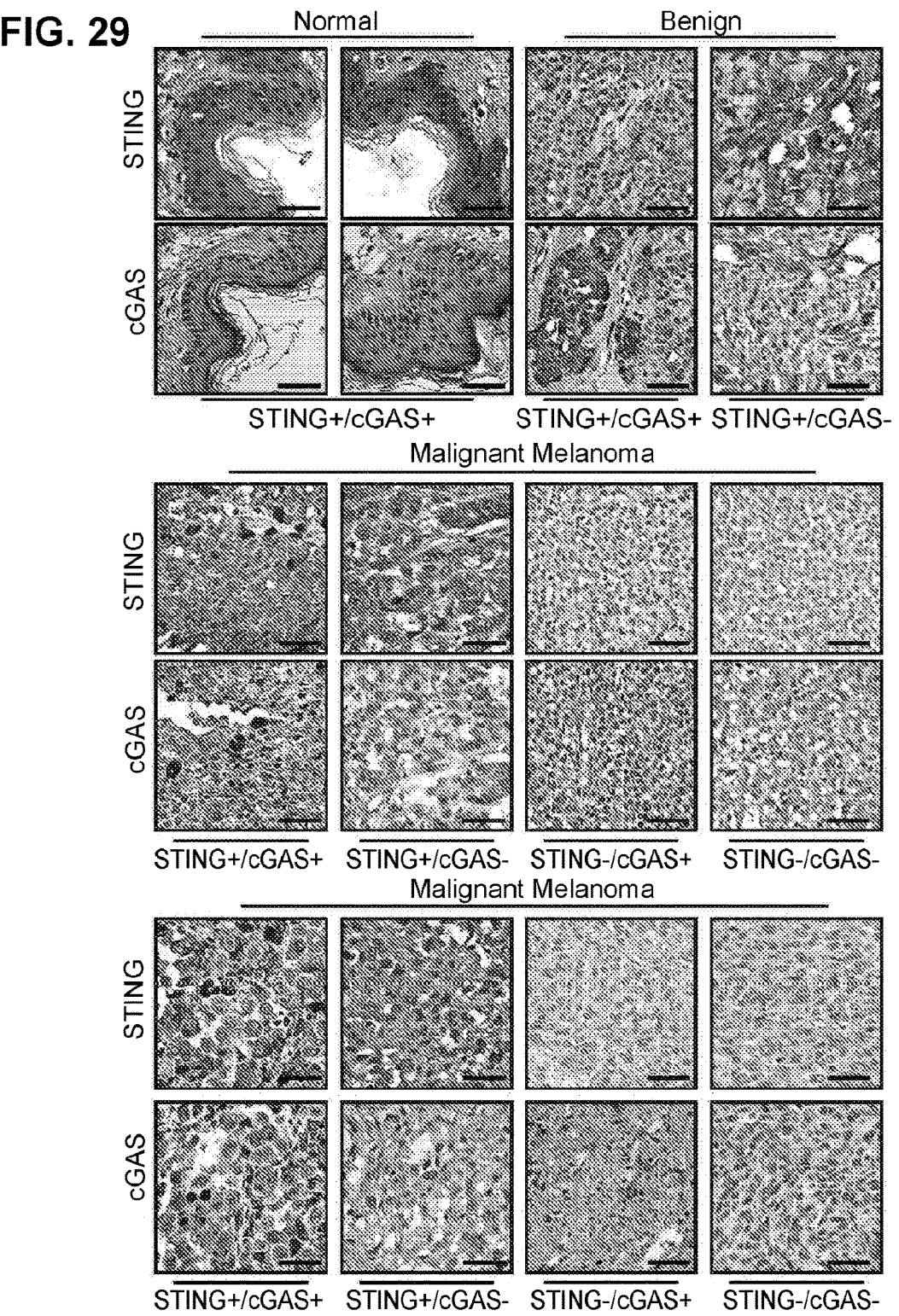
FIG. 29. STING and cGAS expression were suppressed in high percentage of human melanomas. Immunohistochemistry analysis of STING and cGAS in human melanoma tissue microarray containing normal human epidermal and human melanoma tissues. Representative images of normal human epidermal and human melanoma tissues stained for STING and cGAS. Images are shown at 400×. Bar size, 50 µm. STING and cGAS expression status is summarized and shown in bottom panel.

To evaluate STING/cGAS expression in patient-derived melanoma samples, we subsequently examined by IHC analysis a paraffin embedded melanoma tissue microarray (TMA, MEL961, Pantomics) that contains 8 normal skin tissues, 8 benign nevus tissues, 56 malignant melanoma tissues and 24 metastatic melanoma tissues. It was observed that all normal tissues expressed both STING and cGAS. cGAS was not detected in 2 benign nevus tissues, while STING was noted to be present in all 8 nevi. In malignant melanoma tissues, 23.2% of melanoma samples lost STING expression, while 16.1% of melanoma samples did not express cGAS, and both STING and cGAS were absent in 14.3% of melanoma tissues. In more advanced metastatic melanoma tissue, loss of both STING and cGAS was more profound (41.7%) (FIG. 29). Given this data, suppression of STING or cGAS expression may commonly occur in human melanoma and plausibly other human cancers (Xia et al, 2016). In summary, our IHC procedures may be useful for the analysis of cGAS and STING expression in FFPE preserved clinical tumor samples.

STING/cGAS Expression May be Suppressed Through DNA Hypermethylation in Melanoma Cells.

Loss of STING/cGAS expression could occur through either genetic alteration or mutation. To evaluate the gene status of STING and cGAS in melanoma cells, we sequenced the STING and cGAS gene within all 11 melanoma cells. Sequence analysis of the entire STING gene (introns and exons comprise approximately 7.2 kb on chromosome 5q31.2) indicated that 7 of the 11 melanoma cells exhibited HAQ STING variant (Jin et al., 2011, Yi et al., PloS One, 2013), which was previously reported to occur in approximately 20% of the population. STING gene in all melanoma cells as well as normal HEMa cell contains the R272 polymorphism, which was reported to represent approximately 85% of the population but does not exert any defects in STING function. Collectively, sequence analysis did not reveal any major genetic defect in the STING gene within the melanoma cells. Similar sequence analysis was also carried out on cGAS exons. However, no major mutations or deletions were noted. Taken together, genetic mutations or deletions do not seem to be involved in STING/cGAS defective expression in melanoma cells.

Figure 30A:
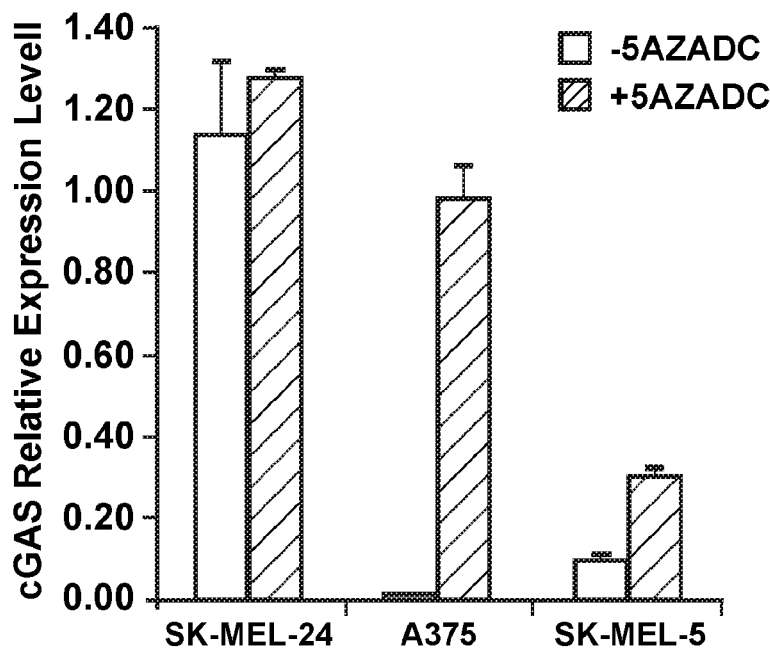
FIGS. 30A-30G show DNA demethylation partially recapitulated STING and cGAS expression in human melanoma cell lines.
Figure 30B:
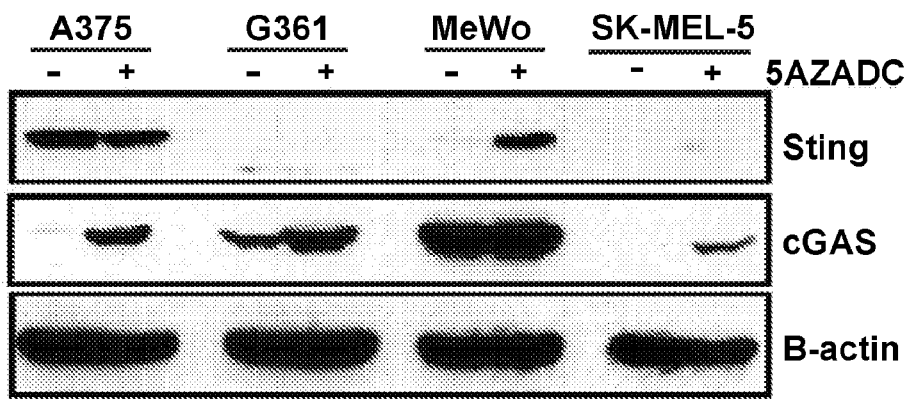
Figure 30C:
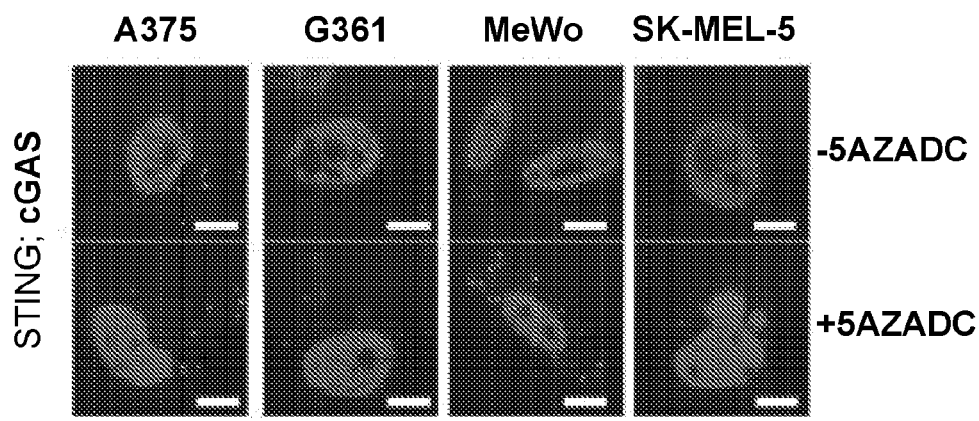
Figure 30D:
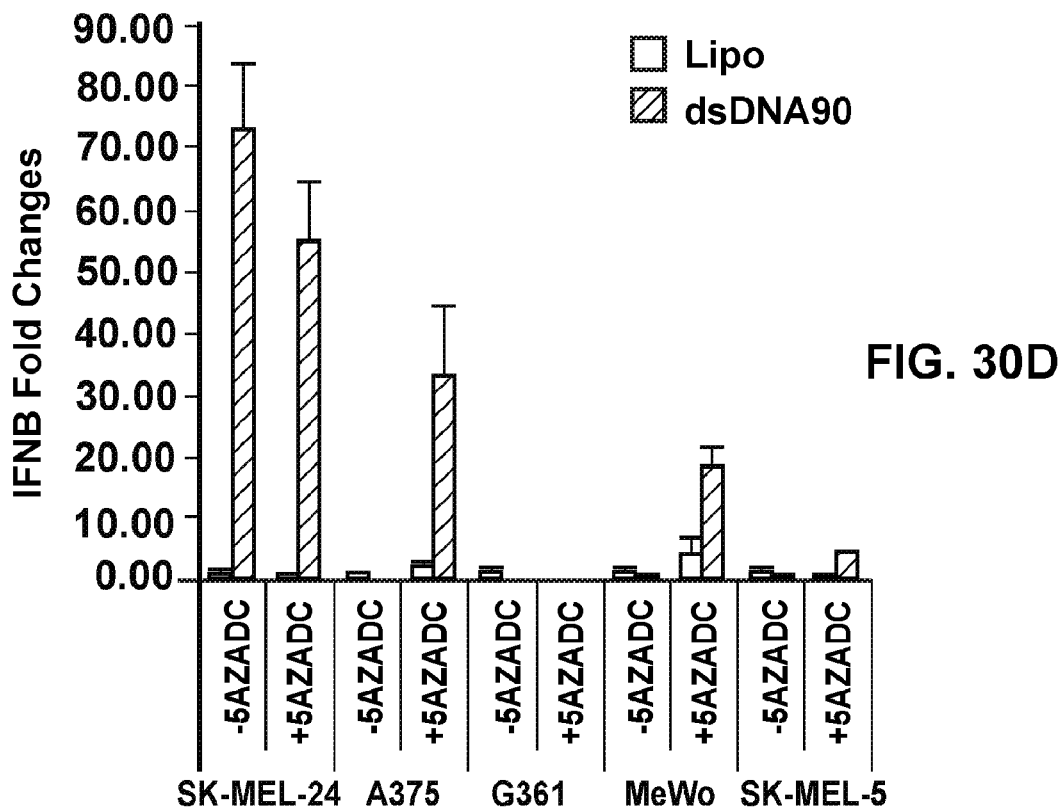
Figure 30E:
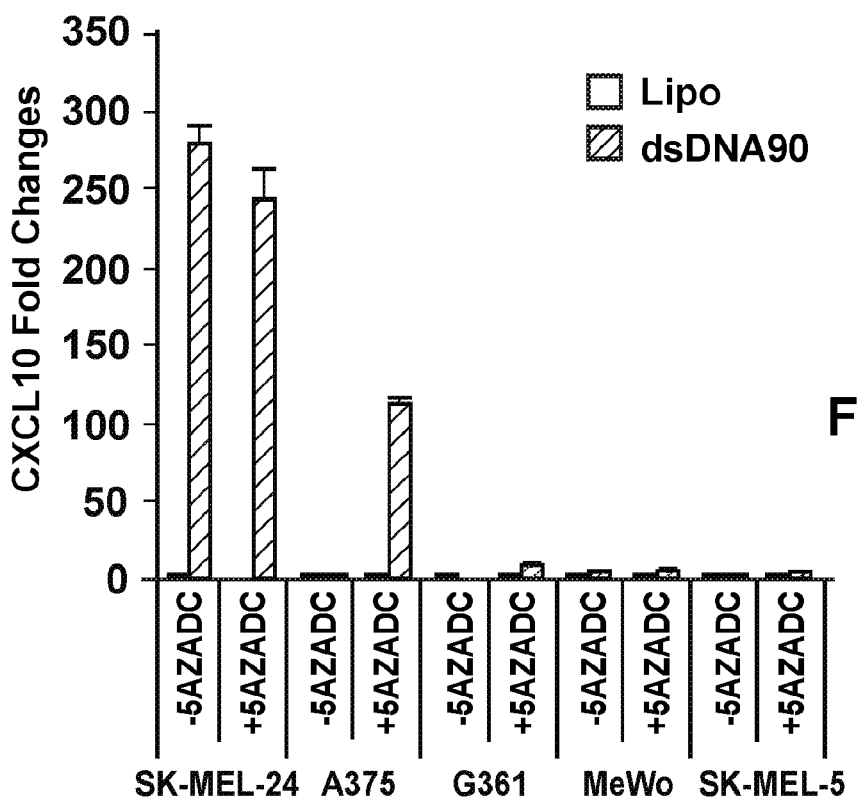
Figures 30F, 30G:
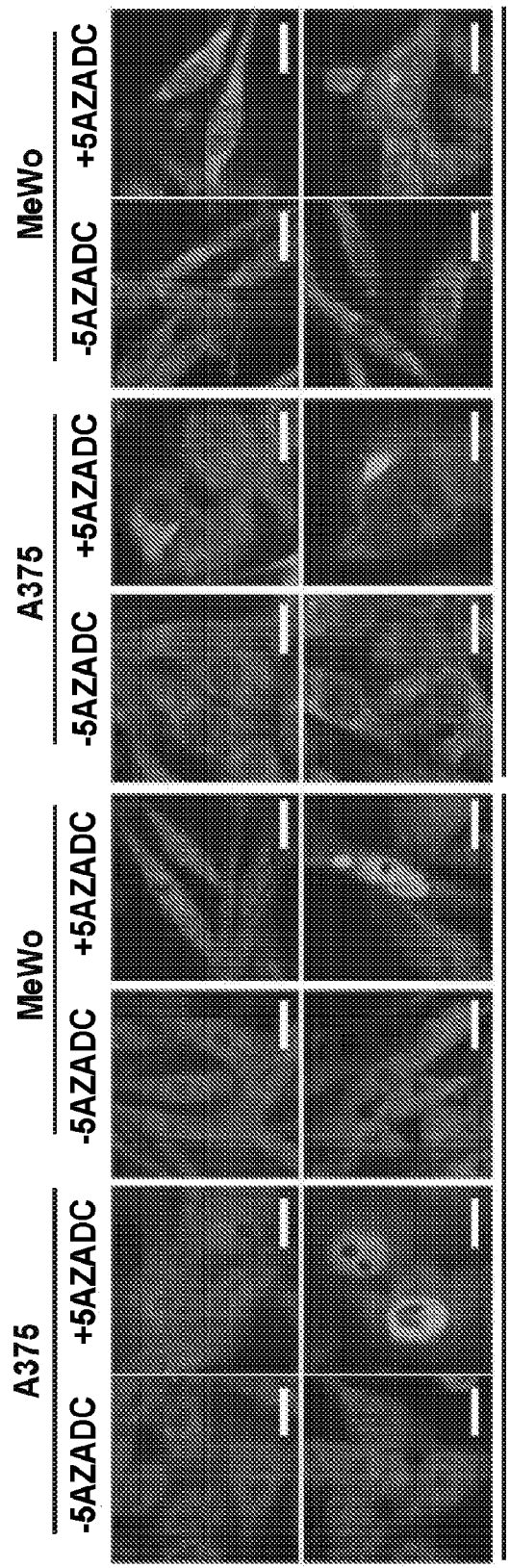

In view of this, it was examined whether STING or cGAS expression was suppressed by epigenetic processes, such as by hypermethylation of the promoter regions (20, 21). Indeed, databank analysis indicated the presence of considerable CpG islands within the STING and cGAS promoter region. As such, melanoma cells lacking either STING or cGAS expression were treated with the de-methylating agent 5-Aza-2'-deoxycytidine (5AZADC) for 5 days and evaluated recapitulation of STING or cGAS expression. Realtime PCR analysis showed that cGAS expression was recovered in A375 cells as well as SK-MEL-5 cells although at lower extent. Although SK-MEL-24 exhibited low cGAS expression by RT-PCR, 5AZADC treatment did not seem to affect cGAS expression level of SK-MEL-24 cells significantly (FIG. 30A). This result was again confirmed by both immunoblot and RNA FISH analysis, in which cGAS expression was apparently recapitulated in A375 and SK-MEL-5 cells following 5AZADC demethylation (FIG. 30B-C). In MeWo cells, STING expression was restored by 5AZADC treatment as shown by both immunoblot and RNA FISH analysis. However, STING remained absent in similarly treated G361 cells as well as in SK-MEL-5 cells, although cGAS expression was partially restored in the same treated SK-MEL-5 cells (FIG. 30A-C). Therefore DNA hypermethylation is involved in silencing STING or cGAS expression in some melanoma cells (A375 and MeWo). However it is not yet clear why expression levels of STING are muted in the remainder melanoma cells (G361, SK-MEL-5). Other epigenetic modifications such as histone modifications or other transcription regulator factors such as miRNA could be involved in suppressing STING and/or cGAS expression (Jin et al., 2013, Yarbrough et al., 2014). To determine if reconstitution of STING/cGAS expression rescued STING-dependent dsDNA signaling, IFNB and CXCL10 induction was examined in 5AZADC treated melanoma cells following dsDNA stimulation. Induction of both IFNB and CXCL10 production was observed in cGAS rescued A375 cells, as well as modest expression of IFNB in STING rescued MeWo cells, concomitant with IRF3 and STING translocation (FIG. 30D-G). Whereas no STING function was observed in G361 or SK-MEL-5 cells following 5AZADC treatment, confirmed that both STING and cGAS are necessary for dsDNA stimulated cytokine production (FIG. 30D-E). Thus, demethylating agents may be able to partially rescue STING-dependent innate immune gene induction in select melanoma cells.

Defect in STING Signal Renders Melanoma Cells Susceptible to DNA Virus Infection.

Figure 31A:
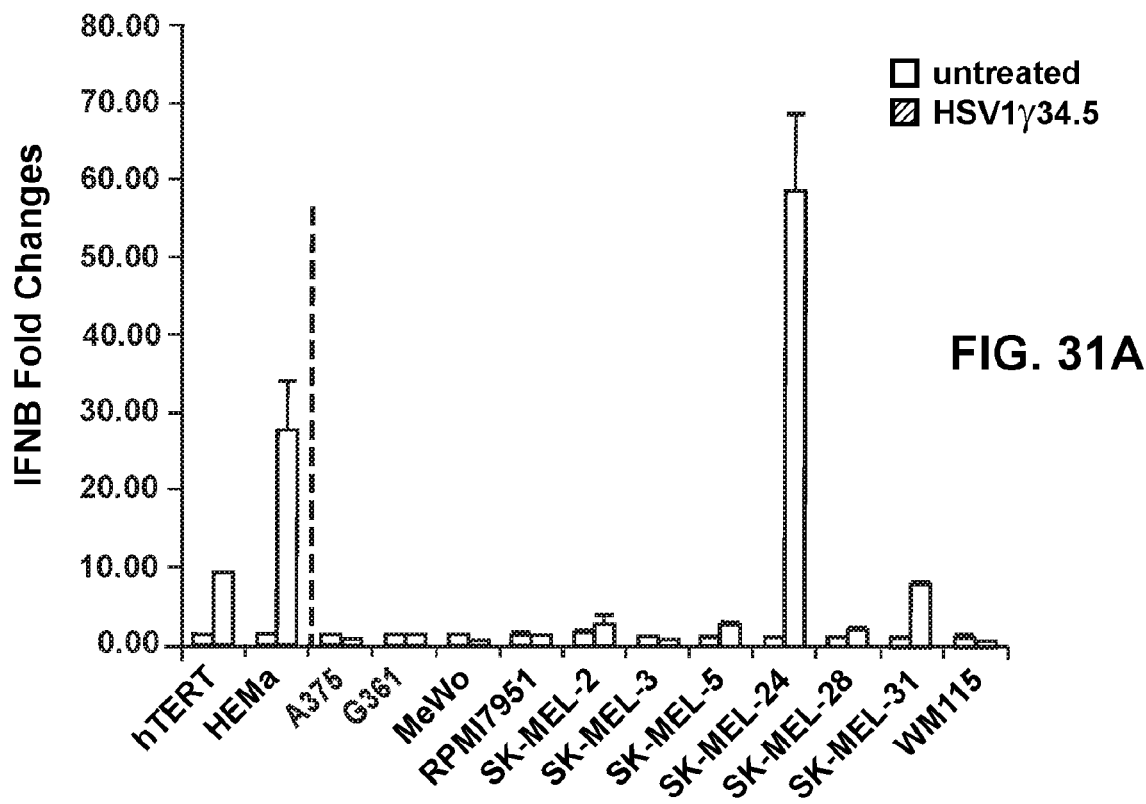
FIGS. 31A-31D show STING signal defect leads melanoma cells more susceptible to HSV1 infection. Cells (same as in FIG. 1) were infected with HSV1γ34.5 at M.O.I. 5 for 1 hour and human IFNB (FIG. 31A) and CXCL10 (FIG. 31B) induction was analyzed by qPCR 3 hours post infection.
Figure 31B:
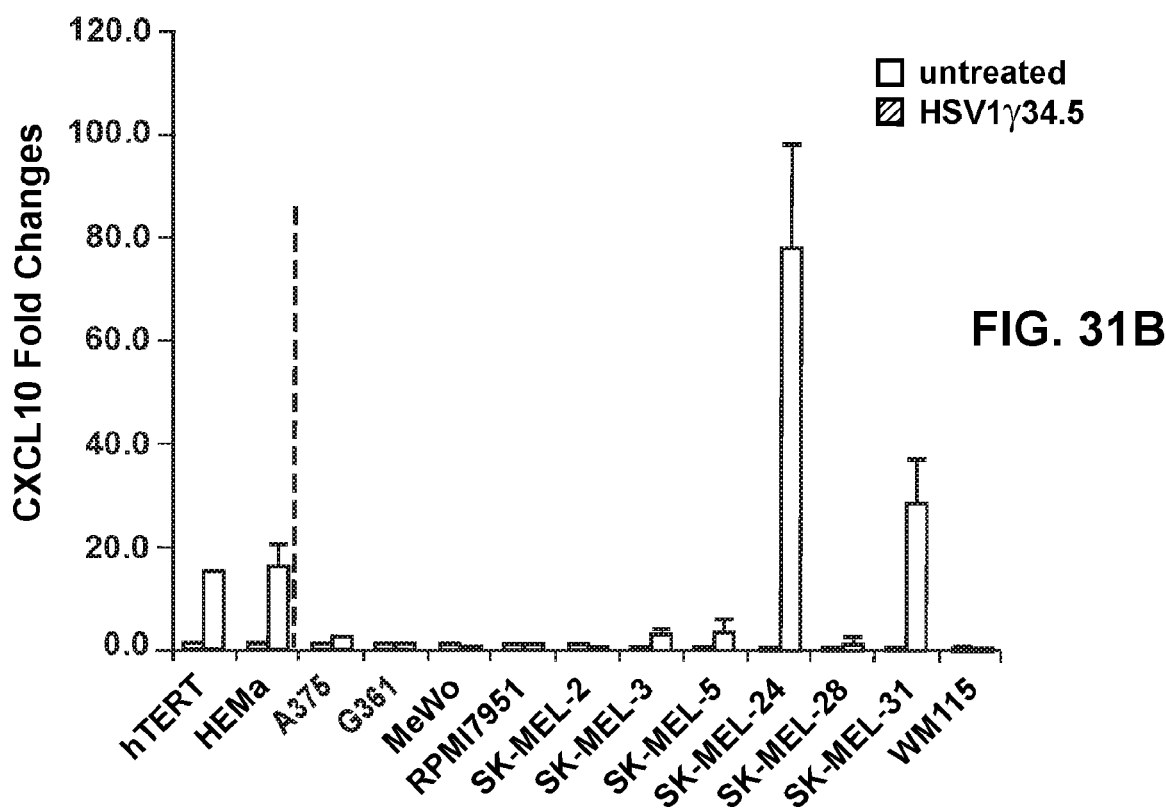
Figure 31C:
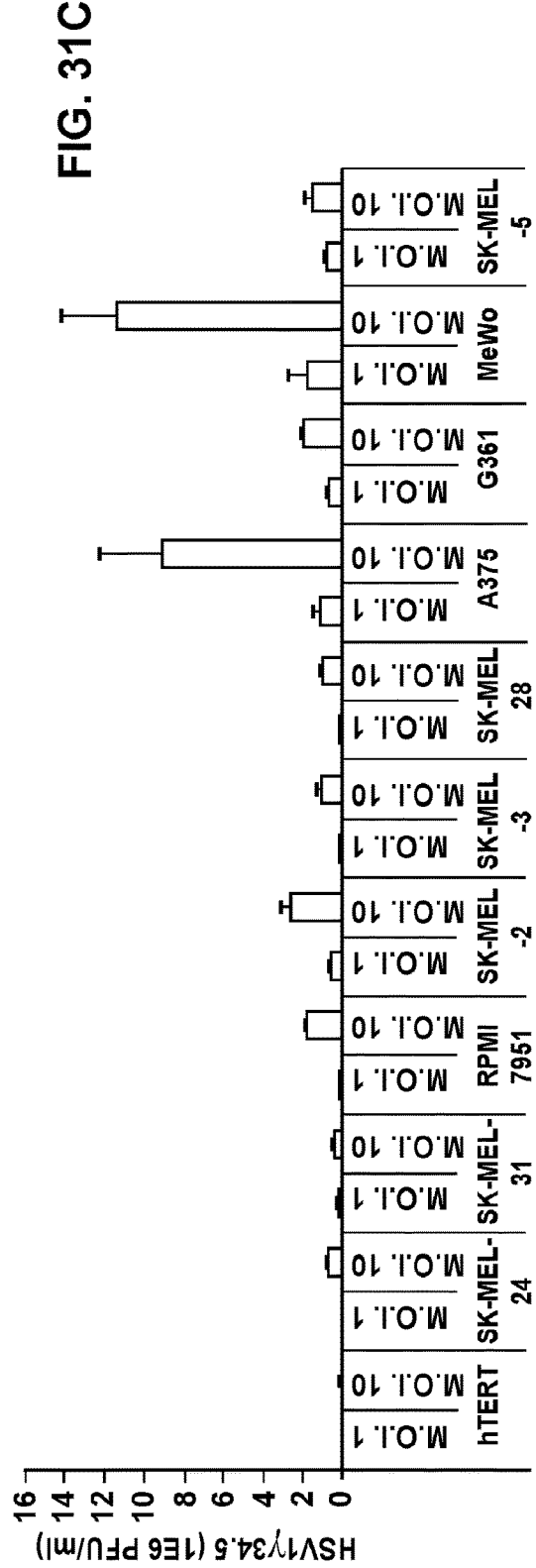
Figure 31D:
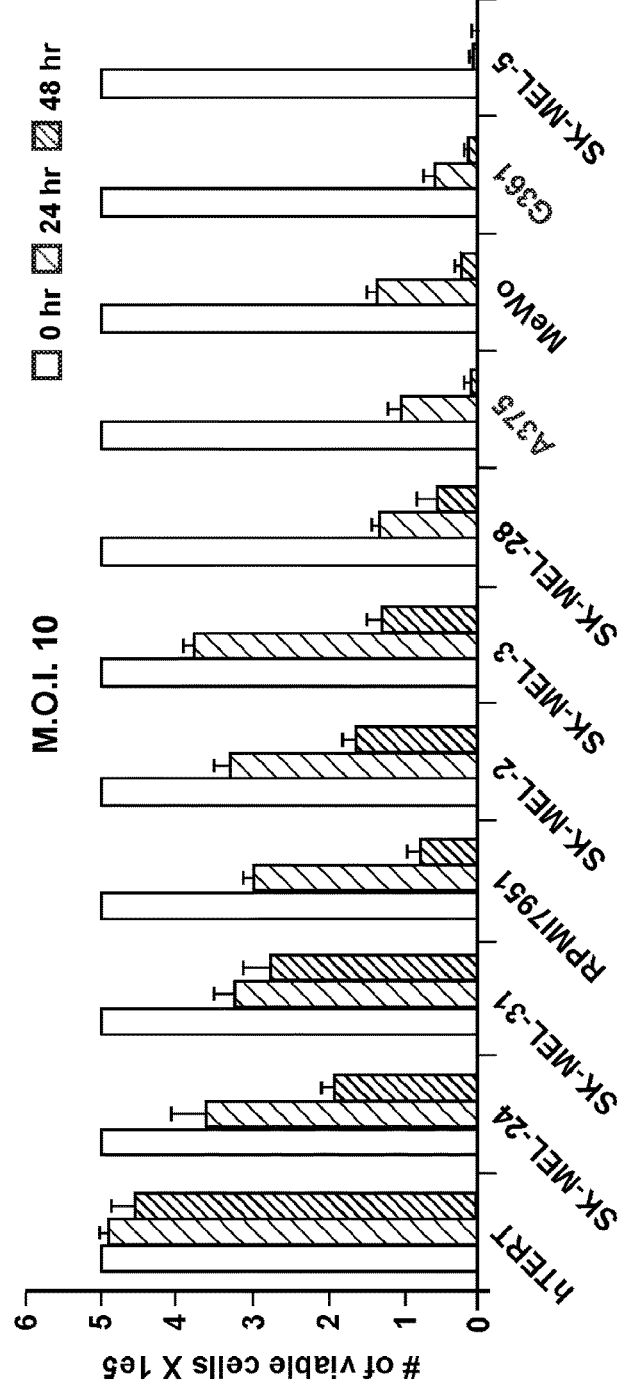

STING innate immune signaling plays a critical role in host defense responses to DNA viruses. For example, mice lacking STING are extremely sensitive to Herpes simplex virus (HSV) infection (Ishikawa et al., 2008, Ishikawa et al., 2009). A strain of HSV1 lacking the γ34.5 gene, referred to as talimogene laherparepvec (OncoVex, T-VEC) is presently being evaluated in clinical trials as a therapeutic agent for the treatment of cancer including melanoma (Andtbacka et al., 2015; Lawler et al., 2015; Kolodkin-Gal et al., 2009). However, the mechanisms of oncolysis remain to be fully determined and there is no evaluation, presently, for determining the likely efficacy of HSV-based antitumor treatment. Is was previously shown that STING activity is defective in numerous colon cancer cells which renders cells sensitive to DNA virus infection including HSV1. We postulated that lack of STING function in melanomas cells may correlate with an increased susceptibility to DNA virus infection and replication. Plausibly, the ability of STING to effectively signal may affect outcome to HSV-based oncoviral therapy. To start addressing this we infected the melanoma cells or control hTERT and HEMa with HSV1 lacking the γ34.5 gene similar to the strain presently being investigated as an oncolytic agent against human melanoma. The γ34.5 viral protein has been proposed to suppress host defense responses, although the mechanisms need to be fully clarified. Thus, without the robust repression of the host innate immune signaling, HSV1γ34.5 is able to potently trigger STING-dependent innate immune activation, including type I IFN production (Ishikawa et al., 2009). Similar to dsDNA treatment, HSV1γ34.5 induced robust production of IFNB and CXCl10 mRNAs in control hTERT and HEMa cells, as well as in SK-MEL-24 and SK-MEL-31 cells that retained partial STING signaling (FIG. 31A-B). However, little type I IFN production was observed in the remainder of the melanoma cells. Loss of the ability to induce type I IFN correlated with increased HSV1γ34.5 replication, likely due to the impaired anti-viral effects, especially in melanoma cells lacking STING/cGAS expression (A375, G361, MeWo and SK-MEL-5) (FIG. 31C). Furthermore, cells with defective STING signal underwent rapid cell death, likely due to robust viral replication whereas control cells and cells with partial STING function (SK-MEL-24 and SK-MEL-31) were significantly more resistant (FIG. 31D). This data confirmed that melanoma cells exhibiting defective STING-signaling enabled more HSV1 replication and lysis.

The ability of Vaccinia Virus (VV) to activate host innate immune signaling in the absence of STING function in melanoma cells was also examined. VV, a dsDNA virus with 190 kb genome that replicates in the cytoplasm of infected cells, is another candidate DNA virus that is currently under evaluation as an oncolytic therapeutic agent to treat cancer (Rowe et al., 2014). Similar to our observations using HSV1γ34.5, VV triggered type I IFN and CXCL10 production only in the control cells and melanoma cells with partial STING function but not in cells with loss of STING/cGAS expression (A375, G361, MeWo and SK-MEL-5). Our results indicate that melanoma cells with defective STING-signaling are highly susceptible to HSV1 and VV infection. Thus, it is plausible that melanoma lacking STING/cGAS expression are more sensitive to DNA virus oncolytic activity and being able to measure STING/cGAS expression in melanoma tissue may help predict the response of patients to selected viral oncolytic therapy.

In Vivo Analysis of Melanoma Cells to HSV1γ34.5 Therapy.

Figure 32A:
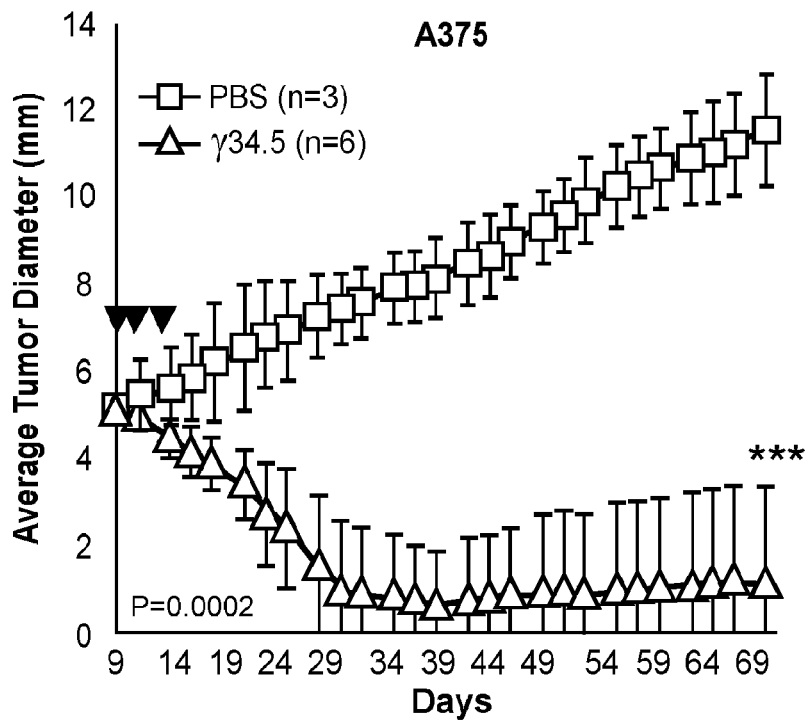
FIGS. 32A-32D show increased HSV1γ34.5 oncolytic effect was observed in melanoma xenografts with impaired STING signal in vivo.
Figure 32B:
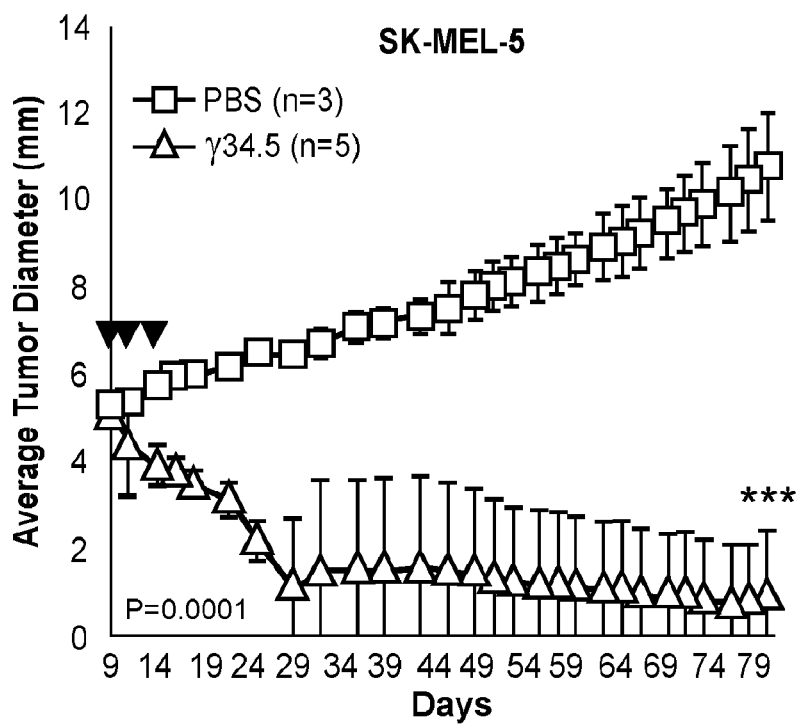
Figure 32C:
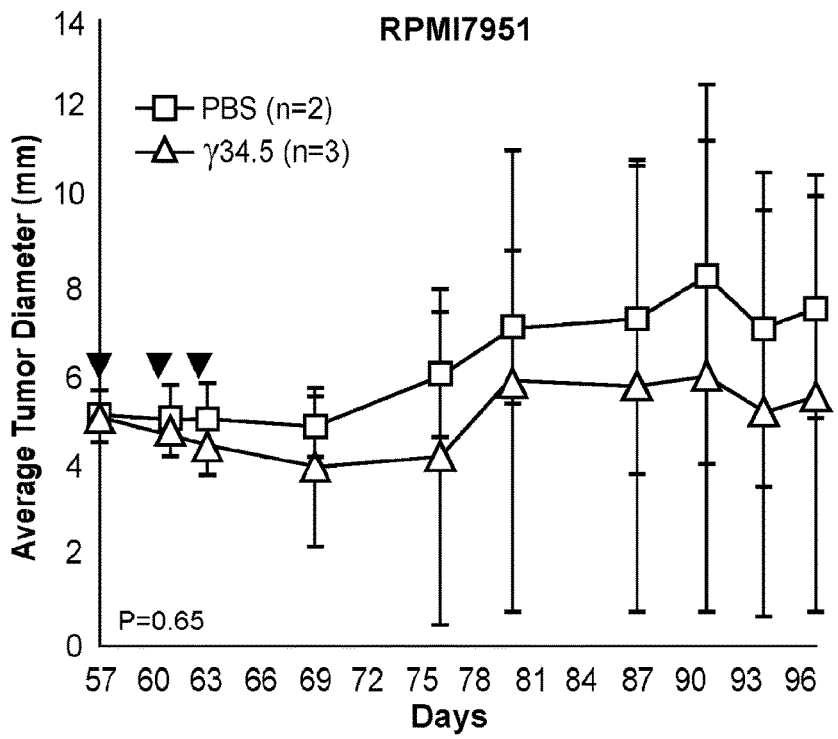
Figure 32D:
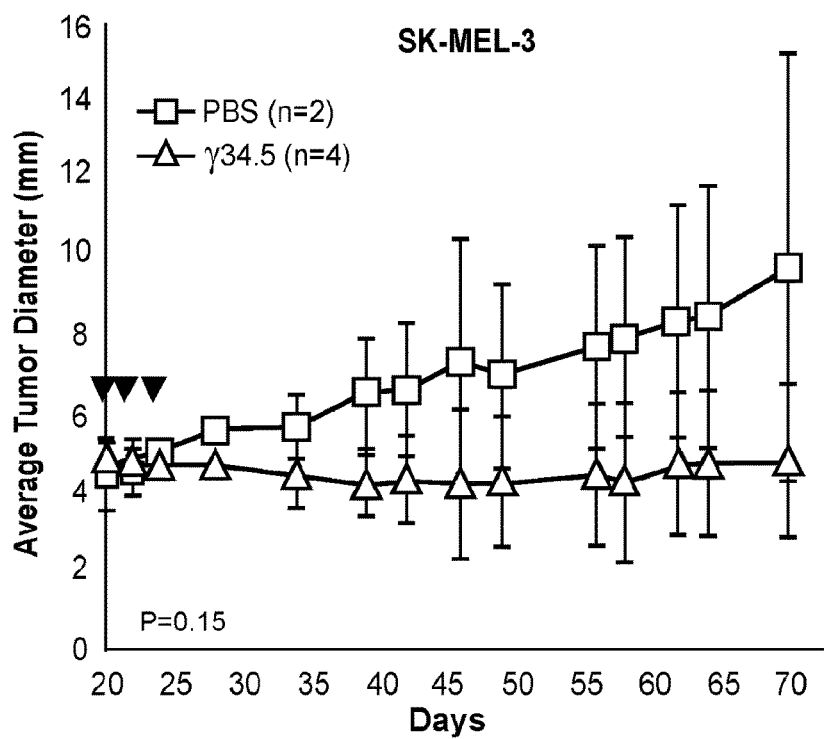

Our in vitro analysis indicated that loss of STING signaling may affect the outcome of select oncoviral therapy (FIG. 31A-D). To further evaluate this possibility, in vivo, melanoma xenografts were generated by subcutaneously inoculating nude mice with melanoma cells harboring partial (RPMI7951 and SK-MEL-3) or defective (A375, MeWo and SK-MEL-5) STING signaling. HSV1γ34.5 was then administered intratumorally and tumor growth monitored (FIG. 32). Results showed that tumors derived from melanoma cells with defective STING-signaling were extremely susceptible to HSV1γ34.5 treatment (FIG. 32A-B). Tumor size decreased rapidly after HSV1γ34.5 treatment. 4 out of 6 A375 tumors and 3 out of 5 SK-MEL-5 tumors diminished 2-3 weeks after treatment (FIG. 32A-B). In contrast tumors derived from melanoma cells exhibiting partial STING signaling (RPMI7951 and SK-MEL-3) were refractory to viral oncolytic treatment (FIG. 32C-D). While these tumors are slow growing in vivo, majority of mice did not respond to HSV1γ34.5 therapy at all and the animals were sacked after the tumor burden became significant. Therefore, our findings complement our previous studies and indicate that the ability of measure STING function in melanoma may predict the outcome of DNA virus-related oncolytic therapy against human melanoma and perhaps other type of cancers.

Discussion

As reported above, STING signaling is frequently suppressed in human colon cancer. As mentioned, loss of intrinsic STING signal may play a key role in preventing cancer development through inability to respond to DNA damage and alert the immune surveillance machinery (Chatzinikolaou et al., 2014, Kondo et al., 2013). To extend these studies, the expression and regulation of STING signaling in melanoma was analyzed and it was similarly found that STING-dependent cytokine production was frequently suppressed in human melanoma. Although no significant mutation or deletion events involving the STING or cGAS genes was observed, the inhibition of STING signaling was found to mainly occur through epigenetic suppression of STING and or cGAS expression. Cytosolic DNA mediated STING signaling was partially rescued by demethylating agent (5AZADC) treatment in some STING-defective melanoma cells, suggesting DNA hypermethylation is one of the mechanisms for STING/cGAS suppression. However, in other STING-defective melanoma cells, demethylation was not effective in being able to restore STING expression. STING and/or cGAS may selectively become targets for suppression at various stages of cancer development, the suppression of either being sufficient to impede STING function. It was also noticed in some melanoma cells, that although both STING/cGAS were expressed, the ability of STING to effectively activate the transcription factors NF-κB or IRF3 was impaired by molecular mechanisms that remain to be determined. Thus, STING function can be impaired at different steps along the signaling pathway, although epigenetic suppression of either STING/cGAS expression seems to be common. Collectively, it was observed that STING-dependent signaling was defective in numerous melanomas which indicated that inhibiting STING function maybe a key obligation for the development of melanoma, plausibly enabling such cells to evade the immune system.

Loss of STING may be common in tumors and may even predict outcomes to anti-cancer therapy. Accordingly, assays were developed herein to evaluate the expression levels of both STING and cGAS, loss of either of which will affect STING function. These assays were validated in melanoma and showed that both RNAish based and IHC based assays were able to measure STING and cGAS mRNA or protein expression in melanoma cells accurately and sensitively. Using IHC, a melanoma TMA was screened which showed loss of either STING or cGAS in over 50% malignant and over 60% metastatic melanomas. Loss of STING function may not be a key tumor onset factor. However, STING does appear to be important in the generation of cytokines in response to DNA damage (Ahn et al., 2015, Xia et al., 2016, Ahn et al., 2014). Loss of STING function is almost certainly important in later stages of cancer development to escape immunosurveillance and host anti-tumor immunity, especially beneficial in tumor metastasis. The assays described may be useful in predicting the effective response rates of cancers to select therapeutic interventions. Furthermore, recapitulating STING signal in tumors, via novel antitumor gene therapy approaches, may reactivate host antitumor immunity against escaped tumor cells.

Accordingly, it was noticed that loss of STING function in melanoma cells rendered cells highly sensitive to DNA-virus mediated oncolytic effect (such as HSV1). Oncolytic HSV1 is one viral therapeutic agent in clinical application. For example, talimogene laherparepvec (T-VEC) (Amgen) is a herpes simplex virus type 1 (HSV-1) based OV that has been engineered to express granulocyte-macrophage colony-stimulating factor (GM-CSF) to increase immune recognition. Although T-VEC has shown improved effect over traditional immune therapies for advanced melanoma, the overall response rate is still limited. This phenomena could be potentially due to diverse STING/cGAS expression status among melanoma cases. Oncolytic viruses may directly destroy the tumor cell by lysis as well as create a tumor antigen source for activation of anti-tumor immune response (Woo et al., 2015). STING may play key roles in both of these processes. Therefore, utilization of STING/cGAS as molecular biomarker may enable a more predictive response to the use of microbes for the treatment of cancer. Such assays may also shed insight into the efficacy of other STING-dependent anti-tumor therapies based on CDNs, or even DNA-adduct based chemotherapeutic regimes (Zitvogel et al., 2013). Further, gene therapies involving modification of the STING/cGAS status may provide advantages of utilizing host innate and adaptive defense mechanism to facilitate antitumor effects in combination with traditional anti-tumor therapies. Thus, further studies on STING signal in cancer development may provide insight into the molecular mechanisms of human carcinogenesis as well as provide novel anti-tumor therapeutic approaches.

Experimental Procedure

Materials.

All reagents were from ThermoFisher Scientific or Sigma unless specified.

Cell Culture.

Normal human melanocytes (HEMa) and human melanoma cell lines were purchased from ThermoFisher Scientific and ATCC respectively and cultured in their appropriate growth media according to the instructions. hTERT-BJ1 Telomerase Fibroblasts (hTERT) were originally purchased from Clontech and were cultured in 4:1 ratio of DMEM:Medium 199 supplement with 10% FBS, 4 mM L-Glutamine and 1 mM sodium pyruvate at 37° C. in a 5% $CO_2$-humidified atmosphere.

Immunoblot Analysis.

Equal amounts of proteins were resolved on sodium dodecyl sulfate (SDS)-Polyacrylamide gels and then transferred to polyvinylidene fluoride (PVDF) membranes (Millipore). After blocking with 5% Blocking Reagent, membranes were incubated with various primary antibodies (and appropriate secondary antibodies). The image was resolved using an enhanced chemiluminescence system ECL (Thermo Scientific) and detected by autoradiography (Kodak). Antibodies: rabbit polyclonal antibody against STING was developed in our laboratory as described previously in Ishikawa et al, 2008; other antibodies were obtained from following sources: β-actin (Sigma Aldrich), p-IRF3 (Cell Signaling), IRF3 (Santa Cruz Biotechnology), p-p65 (Cell Signaling), p65 (Cell Signaling), p-TBK1 (Cell Signaling), TBK1 (Abcam), cGAS (Cell Signaling).

Interferon β ELISA Analysis.

Interferon β Elisa was performed as above.

Immunofluorescence Microscopy. Cells were cultured and treated in their appropriate media on Lab-Tek II chamber slides. Cell were fixed with 4% paraformaldehyde for 15 minutes in at 37° C. and permeabilized with 0.05% Triton X-100 for 5 minutes at room temperature. Immunostaining was performed with rabbit-anti-STING polyclonal, rabbit-anti-IRF3 (Santa Cruz Biotechnology) or rabbit-anti-p65 (Cell Signaling) followed by fluorescence conjugated secondary antibodies (FITC-goat-anti-rabbit). Images were taken with Leika LSM confocal microscope at the Image Core Facility, University of Miami.

Quantitative Real-Time PCR (qPCR).

Total RNA was reverse-transcribed using QuantiTect Reverse Transcription Kit (Qiagen). Real-time PCR was performed with the TaqMan gene Expression Assay (Applied Biosystems).

Immunohistochemistry and Histological Analysis.

Tissue Microarray was purchased from Pantomics. Immunohistochemistry staining was performed with rabbit-anti-cGAS antibody or rabbit-anti-STING antibody following standard protocol.

Virus Amplification, Purification, Titration and Infection.

HSV-1 γ34.5 was kindly provided by Bernard Roizman. Vaccinia virus (vTF7-3) was kindly provided by John Rose. Virus was amplified in Vero cells and purified by sucrose gradient ultracentrifugation following standard protocol. Plague assay using serial diluted virus was performed in Vero cells following standard protocol. Cells were infected with virus at specific M.O.I. for 1 hour, washed and then incubated for designated period for specific assay examination.

RNA In Situ Hybridization.

STING and cGAS RNA probed was custom designed by ACD and RNA in situ Hybridization was performed using RNAscope® Multiplex Fluorescent Reagent Kit for cultured cells and 2-plex RNAscope® Reagent Kit for FFPE cells and tissue following the manufacturer's instruction.

Mouse Treatment.

Balb/C nu/nu mice were purchased from Charles River and maintained in the institutional Division of Veterinary Resources (DVR). All experiments were performed with institutional animal care and use committee (IACUC) approval and in compliance with IACUC guidelines. Tumor cells were introduced in the flanks of Balb/c nude mice by subcutaneous injection of 2E106 of the appropriate tumor cells and tumors allowed to develop to an average diameter of approximately 0.5 cm. HSV1γ34.5 was then be injected into the tumors every other day for a total of three times at 1E7 PFU. PBS was used as vehicle control. Effects on tumor growth were monitored. Mice were euthanized when tumor diameter exceeds 10 mm.

Genomic DNA Sequencing.

Genomic DNA was extracted from melanoma cells as well as normal cells using Qiagen DNeasy Kit and specific locus was sequenced by Polymorphic DNA Technologies.

Statistical Analysis.

All statistical analysis was performed by Student's t test unless specified. The data were considered to be significantly different when P<0.05.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a human subject with an oncolytic virus, wherein the human subject is suffering from one or more of colorectal cancer, colon cancer and melanoma cancer, the method comprising the steps of:
   a) determining whether the human subject has a defective functional activity of Stimulator of Interferon Genes (STING) by:
   isolating a sample from the human subject having cancer; and
   performing a PCR assay on the sample to determine if a cell population has a defective functional activity of STING;
   b) if the human subject has a defective functional activity of STING, then identifying a selected therapy, wherein the selected therapy is one or more oncolytic viruses having a double stranded (ds) deoxynucleic acid (DNA) (dsDNA) genome selected from the group consisting of herpes simplex virus, Varicella Zoster virus, and vaccinia virus; and
   c) internally treating the human subject with the selected therapy.

2. The method of claim 1, wherein the functional activity of STING is determined to be defective based on the amount of cyclic Guanosine Monophosphate (cGMP)-Adenosine Monophosphate (AMP) Synthase (cGAS) in the cell and cellular levels of one or more mRNA's selected from the group consisting of Interleukin-1 (IL-1), IL-3, IL-18 and IL-22.

3. The method of claim 1, further comprising determining the cellular level of interleukin-22 binding proteins in the cell.

4. The method of claim 3, further comprising determining the cellular level of interleukin-1, interleukin-18 and interleukin-22 in the cell.

5. The method of claim 2, wherein the cancer is colorectal adenocarcinoma and the selected therapy comprises administering to the subject the oncolytic virus HSV1k34.5.

6. The method of claim 5, wherein the oncolytic virus induced the production of interferons.

7. The method of claim 1, wherein the selected therapy is administration of 4 µg/ml of dsDNA and interferon-beta.

8. The method of claim 1, comprising
determining the functional activity of STING in a sample from the subject having the cancer; and
if the sample does not have defective STING activity, administering a cancer treatment to the subject that does not cause DNA mutation.

9. A method for treating cancer in a human subject, the method comprising the steps of:
a) determining whether a human subject having one or more of colorectal cancer, colon cancer and melanoma cancer has a defective functional activity of cyclic Guanosine Monophosphate (cGMP)-Adenosine Monophosphate (AMP) Synthase (cGAS) by;
isolating a sample from the human subject having cancer; and
performing a PCR assay on the sample to determine the cellular levels of one or more mRNA's selected from the group consisting of Interleukin-1 (IL-1), IL-3, IL-18 and IL-22 to determine if a cell population has a defective functional activity of cGAS;
b) if the human subject has a defective functional activity of cGAS, then selecting a therapy for the cancer, wherein the therapy involves administering one or more oncolytic viruses having a dsDNA genome selected from the group consisting of herpes simplex virus and vaccinia virus based on the functional activity of the cGAS in the sample, and
c) administering the selected therapy to the human subject.

10. A method for treating cancer in a human subject comprising:
a) determining whether a human subject having one or more of colorectal cancer, colon cancer and melanoma cancer that has failed at least one chemotherapy regimen has a defective functional activity of cyclic Guanosine Monophosphate (cGMP)-Adenosine Monophosphate (AMP) Synthase (cGAS) by:
isolating a first sample from the human subject having cancer; and
performing a PCR assay on the first sample to determine the cellular levels of one or more mRNA's selected from the group consisting of Interleukin-1 (IL-1), IL-3, IL-18 and IL-22 to determine if a cell population has a defective; cGAS activity
b) if the human subject has a defective cGAS activity, then performing a first oncolytic therapy of administering one or more oncolytic viruses selected from the group consisting of herpes simplex virus-1 $\gamma_1 34.5$ deletion and vaccinia virus vTF7-3;

c) determining whether the human subject continues to have a defective functional activity of cGAS by:
isolating a second sample from the human subject having cancer; and
performing a PCR assay on the second sample to determine the cellular levels of one or more mRNA's selected from the group consisting of Interleukin-1 (IL-1), IL-3, IL-18 and IL-22 to determine if a cell population continues to have a defective cGAS activity; and
d) i) if the human subject continues to have a defective cGAS activity, then performing a second oncolytic therapy of administering one or more oncolytic viruses selected from the group consisting of herpes simplex virus, Varicella Zoster virus, and vaccinia virus; or
ii) if the human subject has normal cellular levels of one or more mRNA's selected from the group consisting of Interleukin-1 (IL-1), IL-3, IL-18 and IL-22 then administering a second agent that can increase cGAS levels in the subject in order to improve the outcome of the viral oncolytic therapy.

11. The method of claim 10, wherein step d) i) the oncolytic virus is administered in conjunction with the second agent.

12. The method of claim 1, wherein the cancer is colitis-associated cancer.

13. The method of claim 1, wherein the sample is selected from the group consisting of a body fluid, a cell sample, a tissue sample, a biopsy sample, a tissue print, a skin sample, and a hair sample.

14. The method of claim 13, wherein the body fluid is blood, urine, plasma, saliva, or cerebrospinal fluid.

15. The method of claim 1, wherein an immune response in the cancer patient that has defective STING activity is enhanced by administration of an oncolytic virus selected from the group consisting of herpes simplex virus-1 $\gamma_1 34.5$ deletion and vaccinia virus vTF7-3.

16. The method of claim 15, wherein the immune response includes modulation of T cell activity, modulation of dendritic cell activity, or modulation of immune cytokines.

17. The method of claim 1, wherein the therapy results in increased tumor cell death and/or retarded tumor growth.

18. The method of claim 13, wherein the sample is a soluble fraction of a cell preparation, wherein the cells are grown in cell culture in vitro and the media from the cell culture is tested for functional activity of STING.

19. The method of claim 1, wherein the cancer patient has a defect in cyclic Guanosine Monophosphate (cGMP)-Adenosine Monophosphate (AMP) Synthase (cGAS) activity, and wherein the immune response in said cancer patient is enhanced by administration of an oncolytic virus selected from the group consisting of herpes simplex virus-1 $\gamma_1 34.5$ deletion and vaccinia virus vTF7-3.

20. The method of claim 19, wherein the immune response includes modulation of T cell activity, modulation of dendritic cell activity, or modulation of immune cytokines.

* * * * *